(12) United States Patent
Wilton et al.

(10) Patent No.: US 11,459,563 B2
(45) Date of Patent: Oct. 4, 2022

(54) TREATMENT FOR NEAT1 ASSOCIATED DISEASE

(71) Applicants: The University of Western Australia, Nedlands (AU); MURDOCH UNIVERSITY, Murdoch (AU)

(72) Inventors: Stephen Donald Wilton, Applecross (AU); Sue Fletcher, Bayswater (AU); Archa Fox, Wembley (AU); Ruohan Li, East Perth (AU)

(73) Assignees: The University of Western Australia, Nedlands (AU); MURDOCH UNIVERSITY, Murdoch (AU)

( * ) Notice: Subject to any disclaimer, the term of this patent is extended or adjusted under 35 U.S.C. 154(b) by 0 days.

(21) Appl. No.: 16/483,329

(22) PCT Filed: Feb. 5, 2018

(86) PCT No.: PCT/AU2018/050077
§ 371 (c)(1),
(2) Date: Aug. 2, 2019

(87) PCT Pub. No.: WO2018/141027
PCT Pub. Date: Aug. 9, 2018

(65) Prior Publication Data
US 2021/0355489 A1 Nov. 18, 2021

(51) Int. Cl.
*C12N 15/113* (2010.01)
*A61P 35/00* (2006.01)

(52) U.S. Cl.
CPC ............ *C12N 15/113* (2013.01); *A61P 35/00* (2018.01); *C12N 2310/113* (2013.01); *C12N 2310/314* (2013.01); *C12N 2310/3233* (2013.01); *C12N 2320/34* (2013.01)

(58) Field of Classification Search
CPC ........................ C12N 15/113; C12N 2310/113
See application file for complete search history.

(56) References Cited

U.S. PATENT DOCUMENTS

| | | |
|---|---|---|
| 4,458,066 A | 7/1984 | Caruthers et al. |
| 5,149,797 A | 9/1992 | Pederson et al. |
| 6,287,860 B1 | 9/2001 | Monia et al. |
| 6,683,173 B2 | 1/2004 | Dempcy et al. |
| 6,806,084 B1 | 10/2004 | Debs et al. |
| 6,887,906 B1 | 5/2005 | Teng et al. |
| 6,965,025 B2 | 11/2005 | Gaarde et al. |
| 6,969,400 B2 | 11/2005 | Rhee et al. |
| 2003/0027780 A1 | 2/2003 | Hardee et al. |
| 2004/0248833 A1 | 12/2004 | Emanuele et al. |
| 2010/0016215 A1 | 1/2010 | Moulton et al. |

FOREIGN PATENT DOCUMENTS

| | | | |
|---|---|---|---|
| WO | WO-9744450 A1 * | 11/1997 | ............ C12N 15/67 |
| WO | 2009/127230 A1 | 10/2009 | |
| WO | 2015/118156 A1 | 8/2015 | |
| WO | 2015/161189 A1 | 10/2015 | |

OTHER PUBLICATIONS

Supplementary European Search Report and Opinion from European Patent Application No. EP 18 74 8746 dated Oct. 20, 2020.
Vickers et al., Fully modified 2' MOE oligonucleotides redirect polyadenylation, Nucl. Acids Res., 29(6):1293-1299 (2001).
Zhou et al., Chapter 16, Targeting long noncoding RNA with antisense oligonucleotide technology as cancer therapeutics, Methods Mol. Biol., 1402:199-213 (2016).
An et al., ALS-linked FUS mutations confer loss and gain of function in the nucleus by promoting excessive formation of dysfunctional paraspeckles, Acta Neuropathologica Communications, 7:7-14 (2019).
Modic et al., Cross-Regulation between TDP-43 and Paraspeckles Promotes Pluripotency-Differentiation Transition, Molecular Cell, 74:951-965 (2019).
Shelkovnikova et al., Compromised paraspeckle formation as a pathogenic factor in FUSopathies, Human Molecular Genetics, 23(9):2298-2312 (2014).
Shelkovnikova et al., Protective paraspeckle hyper-assembly downstream of TDP-43 loss of function in amyotrophic lateral sclerosis, Molecular Neurodegeneration, 13:30 (2018).
Yamazaki et al., Functional Domains of NEAT1 Architectural lncRNA Induce Paraspeckle Assembly through Phase Separation, Molecular Cell, 70:1038-1053 (2018).
Wolff et al., Direct gene transfer into mouse muscle in vivo, Science, 247:1465-1468 (1990).
Wu et al., Nuclear-enriched Abundant Transcript 1 as a Diagnostic and Prognostic Biomarker in Colorectal Cancer, Mol. Cancer., 14(1):191 (2015).
Wu et al., Receptor-mediated gene delivery and expression in vivo, J. Biol. Chem., 263:14621-14624 (1988).
Xianguo et al., Promoting progression and clinicopathological significance of NEAT1 over-expression in bladder cancer, Oncotarget, (2016).
Anderson, Human gene therapy, Science, 256:808-813 (1992).
Barteau et al., Physicochemical parameters of non-viral vectors that govern transfection efficiency, Curr. Gene. Ther., 8(5):313-23 (2008).
Beaucage et al., Deoxynucleoside phosphoramidites—A new class of key intermediates for deoxypolynucleotide synthesis, Tetrahedron Letters, 22:1859-1862 (1981).
Brigham et al., In vivo transfection of murine lungs with a functioning prokaryotic gene using a liposome vehicle, Am. J. Med. Sci., 298:278-281 (1989).

(Continued)

*Primary Examiner* — Brian Whiteman
(74) *Attorney, Agent, or Firm* — Marshall, Gerstein & Borun LLP

(57) ABSTRACT

An isolated or purified antisense oligomer for modifying RNA cleavage and processing in the NEAT1 gene transcript or part thereof.

18 Claims, 21 Drawing Sheets

Specification includes a Sequence Listing.

(56) References Cited

OTHER PUBLICATIONS

Chai et al., HuR-regulated lncRNA NEAT1 Stability in tumorigenesis and progression of ovarian cancer, Cancer Med., 5(7):1588-1598 (2016).

Chakravarty et al., The oestrogen receptor alpha-regulated lncRNA NEAT1 is a critical modulator of prostate cancer, Nat. Commun., 5:5383 (2014).

Chen et al., Altered nuclear retention of mRNAs containing inverted repeats in human embryonic stem cells: functional role of a nuclear noncoding RNA, Mol Cell., 35(4): 467-478 (2009).

Choudhry et al., Tumor hypoxia induces nuclear paraspeckle formation through HIF-2(Alpha) dependent transcriptional activation of NEAT1 leading to cancer cell survival, Oncogene, 34(34):4482-90 (2015).

Clemson et al., An architectural role for a nuclear noncoding RNA: NEAT1 RNA is essential for the structure of paraspeckles, Mol Cell., 33:717-726 (2009).

Devereux et al., A comprehensive set of sequence analysis programs for the VAX, Nucleic Acids Res., 12:387-395 (1984).

Dokka et al., Novel non-endocytic delivery of antisense oligonucleotides, Adv. Drug. Deliv. Rev., 44:35-49 (2000).

Fox et al., Paraspeckles: a novel nuclear domain, Curr. Biol., 12(1):13-25 (2002).

Fraley et al., New generation liposomes: the engineering of an efficient vehicle for intracellular delivery of nucleic acids, Trends Biochem. Sci., 6:77-80 (1981).

Friedmann, Progress toward human gene therapy, Science, 244:1275-1281 (1989).

Fu et al., Long noncoding RNA NEAT1 is an unfavorable prognostic factor and regulates migration and invasion in gastric cancer, J. Cancer Res. Clin. Oncol., 142(7):1571-1579 (2016).

Gebski et al., Morpholino antisense oligonucleotide induced dystrophin exon 23 skipping in mdx mouse muscle, Hum. Mol. Genet., 12(15):1801-1811 (2003).

Hames et al., Nucleic acid hybridization, IRL Press, 107-108 (1985).

Hazinski et al., Localization and induced expression of fusion genes in the rat lung, Am. J. Resp. Cell Mol. Biol., 4:206-209 (1991).

Hirose et al., NEAT1 long noncoding RNA regulates transcription via protein sequestration within subnuclear bodies, Mol. Biol. Cell, 25(1):169-183 (2014).

Hutchinson et al., A screen for nuclear transcripts identifies two linked noncoding RNAs associated with SC35 splicing domains, BMC Genomics, 8:39-39 (2007).

Imamura et al., Long Noncoding RNA NEAT1-Dependent SFPQ Relocation from Promoter Region to Paraspeckle Mediates IL8 Expression upon Immune Stimuli, Mol. Cell, 53(3):393-406 (2014).

International Preliminary Report on Patentability for Corresponding International Application No. PCT/AU2018/050077 dated Aug. 15, 2019, 8 pages.

International Search Report and Written Opinion for Corresponding International Application No. PCT/AU2018/050077, dated Mar. 26, 2018, 11 pages.

Jearawiriyapaisarn et al., Sustained dystrophin expression induced by peptide-conjugated morpholino oligomers in the muscles of mdx mice, Mol. Ther., 16(9):1624-1629 (2008).

Li et al., Functional dissection of NEAT1 using genome editing reveals substantial localization of the NEAT1_1 isoform outside paraspeckles, RNA., 23(6):872-881 (2017).

Li et al., Gene therapy progress and prospects: non-viral gene therapy by systemic delivery, Gene Ther., 13(18):1313-9 ((2006).

Livak et al., Analysis of relative gene expression data using real-time quantitative PCR and the 2(-Delta Delta C(T)) Method, Methods, 25(4):402-408 (2001).

Ma et al., Enhanced expression of long non-coding RNA NEAT1 is associated with the progression of gastric adenocarcinomas, World J. Surg. Oncol., 14:41 (2016).

Mann et al., Antisense-induced exon skipping and synthesis of dystrophin in the mdx mouse, Proc. Natl. Acad. Science, 98(1):42-47 (2001).

Mannino et al., Liposome mediated gene transfer, Biotechniques, 6:682-90 (1988).

Mao et al., Direct visualization of the co-transcriptional assembly of a nuclear body by noncoding RNAs, Nat. Cell. Biol., 13(1):95-101 (2011).

Miyada et al., Oligonucleotide hybridization techniques, Methods Enzyrnol., 154:94-107 (1987).

Mueller et al., Gene therapy for cystic fibrosis, Clin. Rev. Allergy Immunol., 35(3):164-78 (2008).

Nabel et al., Site-specific gene expression in vivo by direct gene transfer into the arterial wall, Science, 249:11285-1288 (1990).

Naganuma et al., Alternative 3'-end Processing of Long Noncoding RNA Initiates Construction of Nuclear Paraspeckles, EMBO J., 31(20): 4020-4034 (2012).

Peacock et al., Nucleobase and ribose modifications control immunostimulation by a microRNA-122-mimetic RNA, J. Am. Chem. Soc., 133:19200-9203 (2011).

Prasanth et al., Regulating gene expression through RNA nuclear retention, Cell, 123(2):1249-263 (2005).

Remington's Pharmaceutical Sciences, 18th Ed. (1990 Mack Publishing Co., Easton, PA 18042) 1435-1712.

Rosenberg, Immunotherapy and gene therapy of cancer, Cancer Research, 51(18 suppl):5074S-5079S (1991).

Rosenfeld et al., Adenovirus-mediated transfer of a recombinant alpha 1-antitrypsin gene to the lung epithelium in vivo, Science, 252:1431-434 (1991).

Rosenfeld et al., In vivo transfer of the human cystic fibrosis transmembrane conductance regulator gene to the airway epithelium, Cell, 68:1143-155 (1992).

Sasaki et al., MENepsilon/beta noncoding RNAs are essential for structural integrity of nuclear paraspeckles, Proc. Natl. Acad. Sci., 106(8):12525-2530 (2009).

Simoes et al., Cationic liposomes for gene delivery, Expert Opin Drug Deliv., 2(2):237-54 (2005).

Summerton et al., Morpholino antisense oligomers: design, preparation, and properties, Antisense Nucleic Acid Drug Dev., 7:187-197 (1997).

Sun et al., Long non-coding RNA NEAT1 promotes non-small cell lung cancer progression through regulation of miR-377-3p-E2F3 pathway, Oncotarget, 7:51784-51814 (2016).

Sunwoo et al., MEN epsilon/beta nuclear-retained non-coding RNAs are up-regulated upon muscle differentiation and are essential components of paraspeckles, Genome. Res., 19(3):347-359 (2009).

U.S. patent application filed on May 20, 1999, U.S. Appl. No. 09/315,298.

Wang et al., Long noncoding RNA NEAT1 promotes laryngeal squamous cell cancer through regulating miR-107/CDK6 pathway, J. Exp. Clin. Cancer Res., 35:22 (2016).

Wang et al., pH-sensitive immunoliposomes mediate target-cell-specific delivery and controlled expression of a foreign gene in mouse, Proc. Natl. Acad. Sci., USA, 84:7851-7855 (1987).

West et al., Structural, super-resolution microscopy analysis of paraspeckle nuclear body organization, J. Cell Biol., 214:817-30 (2016).

\* cited by examiner

TREATMENT FOR NEAT1 ASSOCIATED DISEASE

CROSS-REFERENCE TO RELATED APPLICATIONS

This application is a U.S. National Phase Application under 35 USC § 371 of International Application No. PCT/AU2018/050077, filed Feb. 5, 2018, which claims priority benefit of Application No. 2017900341 filed on Feb. 3, 2017, in Australia.

INCORPORATION BY REFERENCE OF MATERIAL SUBMITTED ELECTRONICALLY

This application contains, as a separate part of disclosure, a sequence listing in computer-readable form (filename: 54630_SeqListing.txt; 9,792 bytes; created Aug. 9, 2019) which is incorporated by reference in its entirety.

TECHNICAL FIELD

The present invention relates to antisense oligomers to facilitate modification of isoform production in the nuclear paraspeckle assembly transcript 1 (NEAT1) gene. The invention further provides methods to treat, prevent or ameliorate the effects of a disease associated with abnormal expression of the NEAT1 gene by administration of antisense oligomers (ASO) and therapeutic compositions comprising antisense oligomers to the NEAT1 gene.

BACKGROUND ART

The following discussion of the background art is intended to facilitate an understanding of the present invention only. The discussion is not an acknowledgement or admission that any of the material referred to is or was part of the common general knowledge as at the priority date of the application.

Large scale transcriptomic and epigenetic analyses have systematically demonstrated regulatory potential for the majority of our genome. In particular, pervasive transcription occurring largely in the form of long noncoding RNAs (lncRNAs) with diverse and enigmatic functions. LncRNAs are non-coding RNAs that are longer than 200 nucleotides in length. Accumulating evidence has shown that lncRNAs are aberrantly expressed in cancer and play critical roles in tumourigenesis. In this connection, lncRNAs have been shown to regulate cellular processes that are pertinent to cancer development, including cell cycle progression, apoptosis and metastasis. Whilst the majority of lncRNAs are expressed at low levels with tissue-specific and developmental stage specific expression, the mammalian-specific lncRNA NEAT1 (nuclear paraspeckle assembly transcript 1) is ubiquitous and abundant, suggesting a more generic biological role.

NEAT1 transcription can be significantly influenced by p53 and is often upregulated by stresses, such as hypoxia, viral infection/products, and genotoxic agents. There is also a strong link between high NEAT1 expression and more aggressive forms of cancer (Chakravarty et al. 2014, The oestrogen receptor alpha-regulated lncRNA NEAT1 is a critical modulator of prostate cancer. *Nat Commun* 5: 5383; Chai et al. 2016, HuR-regulated lncRNA NEAT1 stability in tumorigenesis and progression of ovarian cancer. *Cancer Med* 5(7): 1588-1598; Chen et al. 2016, Promoting progression and clinicopathological significance of NEAT1 over-expression in bladder cancer. *Oncotarget*. doi: 10.18632/oncotarget.10084; Fu et al. 2016, Long noncoding RNA NEAT1 is an unfavorable prognostic factor and regulates migration and invasion in gastric cancer. *J Cancer Res Clin Oncol* 142(7): 1571-1579; Ma et al. 2016, Enhanced expression of long non-coding RNA NEAT1 is associated with the progression of gastric adenocarcinomas. *World J Surg Oncol* 14: 41; Sun et al. 2016, Long non-coding RNA NEAT1 promotes non-small cell lung cancer progression through regulation of miR-377-3p-E2F3 pathway. Oncotarget. doi: 10.18632/oncotarget.10108; Wang et al. 2016, Long non-coding RNA NEAT1 promotes laryngeal squamous cell cancer through regulating miR-107/CDK6 pathway. *J Exp Clin Cancer Res* 35: 22).

The NEAT1 gene is transcribed as two major isoforms that overlap completely at their 5' ends: the shorter, polyadenylated NEAT1_1 (also called MENepsilon, 3.7 kb in human) and the longer NEAT1_2 isoform (also called MENbeta, 23 kb in human) (Sasaki et al. 2009, MEN epsilon/beta noncoding RNAs are essential for structural integrity of nuclear paraspeckles. PNAS 106(8): 2525-2530; Sunwoo et al. 2009, MEN epsilon/beta nuclear-retained non-coding RNAs are up-regulated upon muscle differentiation and are essential components of paraspeckles. *Genome Res* 19(3): 347-359). The two isoforms are generated from a common promoter and are produced through the use of alternative transcription termination sites. This overlapping nature has caused great difficulties in differentiating the molecular binding targets of each. The majority of the studies involving NEAT1 have not differentiated between the two isoforms. Indeed, most studies have only focused on the common sequence between the short isoform NEAT1_1 and the 5' end of the longer isoform, NEAT1_2.

At the molecular level, NEAT1_2 is important for the formation of paraspeckles, a type of mammalian nuclear RNA-protein body found in close proximity to nuclear speckles (Fox et al. 2002; Hutchinson et al. 2007). Paraspeckles modulate gene expression by sequestrating mRNAs and transcription factors (Fox et al. 2002, Paraspeckles: A Novel Nuclear Domain. *Curr Biol* 12(1): 13-25; Hutchinson et al. 2007, A screen for nuclear transcripts identifies two linked noncoding RNAs associated with SC35 splicing domains. *BMC Genomics* 8: 39-39). NEAT1_2 lncRNAs are localised specifically to paraspeckles. Paraspeckles modulate gene expression by sequestrating mRNAs and transcription factors (Prasanth et al. 2005, Regulating Gene Expression through RNA Nuclear Retention. *Cell* 123(2): 249-263; Chen and Carmichael 2009, Altered Nuclear Retention of mRNAs Containing Inverted Repeats in Human Embryonic Stem Cells: Functional Role of a Nuclear Noncoding RNA. *Mol Cell* 35(4): 467-478; Naganuma et al. 2012, Alternative 3'-end processing of long noncoding RNA initiates construction of nuclear paraspeckles. *EMBO J* 31(20): 4020-4034; Choudhry et al. 2014, Tumor hypoxia induces nuclear paraspeckle formation through HIF-2a dependent transcriptional activation of NEAT1 leading to cancer cell survival. *Oncogene*: doi: 10.1038/onc.2014.1378; Hirose et al. 2014, NEAT1 long noncoding RNA regulates transcription via protein sequestration within subnuclear bodies. *Mol Biol Cell* 25(1): 169-183; Imamura et al. 2014, Long Noncoding RNA NEAT1-Dependent SFPQ Relocation from Promoter Region to Paraspeckle Mediates IL8 Expression upon Immune Stimuli. *Mol Cell* 53(3): 393-406; West et al. 2016, Structural, super-resolution microscopy analysis of paraspeckle nuclear body organization. *J Cell Biol. doi: 10.1083/jcb.201601071*, and their formation occurs when specific architectural proteins, including those of the DBHS (*Drosophila* behaviour/human splicing) family, bind to nascent NEAT1_2 transcripts. Other members of the DBHS protein family include mammalian SFPQ (splicing factor, proline- and glutamine-rich), NONO (Non-POU domain-containing octamer-binding protein) and PSPC1 (paraspeckle component 1), invertebrate NONA (Protein no-on-transient A) and Hrp65.

It has been established that only NEAT1_2 forms the essential RNA backbone for paraspeckle formation (Clemson et al. 2009; Sasaki et al. 2009; Sunwoo et al. 2009; Mao et al. 2011; Naganuma et al. 2012). The shorter isoform of NEAT1, NEAT1_1 is dispensable for paraspeckle formation and we have found that it localises in numerous non-paraspeckle foci we termed 'microspeckles' which may carry paraspeckle-independent functions (Li R, Harvey A R, Hodgetts S I, Fox A H. 2017. Functional dissection of NEAT1 using genome editing reveals substantial localization of the NEAT1_1 isoform outside paraspeckles. *RNA* 23(6): 872-881.).

Upregulation of NEAT1 is associated with a number of cancers, specifically with poor patient outcome and aggressive tumour types. The over-expression of NEAT1_1 in different experimental contexts has been shown to have a protective effect on cancer cell survival, indicating it is acting as an oncogene (Chakravarty et al. 2014, The oestrogen receptor alpha-regulated lncRNA NEAT1 is a critical modulator of prostate cancer. *Nat Commun* 5: 5383).

Many other protein and RNA factors localise to paraspeckles, some with potential roles in paraspeckle function and others not required for function, but potentially regulated by paraspeckle sequestration (Prasanth et al. 2005; Chen and Carmichael 2009; Naganuma et al. 2012; Choudhry et al. 2014). Currently, a working definition of a paraspeckle is a nuclear body in which NEAT1 RNA and DBHS proteins are co-localised (Naganuma et al. 2012).

To dissect the functional relationship between the two NEAT1 isoforms, cell models that selectively express each isoform individually would be required. However, due to the fact that the two NEAT1 isoforms overlap completely at the 5' end, transient specific knockdown of NEAT1_1 is impossible to achieve without perturbing NEAT1_2 levels. In addition, transient over-expression of the 23 kb NEAT1_2 is also very technically challenging (Mao et al. 2011; Naganuma et al. 2012).

The present invention seeks to provide a composition and method to reduce the effects of a disease associated with over-expression of NEAT1_1, and/or under-expression of NEAT12, such as a number of different solid cancers, or to provide the consumer with a useful or commercial choice.

SUMMARY OF INVENTION

The present invention is based on the surprising discovery that the different isoforms of the lncRNA NEAT1, the RNA binding proteins that bind them and the other transcripts modulated by these same proteins, all act together to regulate gene expression in different disease contexts.

Broadly, according to one aspect of the invention, there is provided an isolated or purified antisense oligomer (ASO) for modifying pre-RNA cleavage in the NEAT1 (nuclear paraspeckle assembly transcript 1) gene transcript or part thereof. Preferably, there is provided an isolated or purified antisense oligomer for reducing cleavage that results in production of the NEAT11 gene transcript or part thereof. The reduction in cleavage preferably changes the ration of short form NEAT1_1 and long form NEAT1_2, increasing the amount of long form NEAT1_2, and preferably decreasing the amount of short form NEAT1_1.

Preferably, the antisense oligomer is a phosphorodiamidate morpholino oligomer.

Preferably, the antisense oligomer is selected from the group comprising the sequences set forth in Table 1. Preferably, the antisense oligomer is selected from the list comprising: SEQ ID NO: 1-55. Preferably, the ASO used in the present invention is chosen from the list comprising: SEQ ID NO: 13 to 42, and 55; SEQ ID NO: 13, 22, 24, 26, 28, 30, 32, 34, 36, 38, 40, 42 or 55; or SEQ ID NO: 22, 32 or 55.

The invention extends, according to a still further aspect thereof, to cDNA or cloned copies of the antisense oligomer sequences of the invention, as well as to vectors containing the antisense oligomer sequences of the invention. The invention extends further also to cells containing such sequences and/or vectors.

There is also provided a method for manipulating cleavage factor binding in a NEAT1 gene transcript, the method including the step of:
providing one or more of the antisense oligomers as described herein and allowing the oligomer(s) to bind to a target nucleic acid site.

There is also provided a pharmaceutical, prophylactic, or therapeutic composition to treat, prevent or ameliorate the effects of a disease associated with over-expression of NEAT1_1 and/or under-expression of NEAT1_2 in a subject, the composition comprising:
one or more antisense oligomers as described herein and one or more pharmaceutically acceptable carriers and/or diluents.

Preferably, the disease associated with over-expression of NEAT1_1 and/or under-expression of NEAT1_2 is:
a cancer associated with over-expression of NEAT1_1, which is indicated by the expression of NEAT11 promoting the survival of cancer cells;
a cancer associated with the under-expression of NEAT1_2, which is indicated by the over-expression of NEAT1_1, or alternatively by observations that when NEAT1_2 expression is increased, the cancer's growth is reduced or inhibited;
a cancer associated with paraspeckle insufficiency or low numbers of paraspeckles;
a cancer associated with over-expression of NEAT1_1 and/or under-expression of NEAT1_2 chosen from the list comprising: neuroblastoma, lung cancer including non-small cell lung cancer, oesophageal squamous cell carcinoma, laryngeal squamous cell carcinoma, colorectal cancer, breast cancer, prostate cancer, endometrial endometrioid adenocarcinoma, gastric cancer, glioma, thyroid carcinoma, bladder cancer, osteosarcoma, ovarian cancer;
a cancer chosen from the list comprising: neuroblastoma, lung cancer including non-small cell lung cancer, breast cancer, bladder cancer, colorectal cancer, osteosarcoma, liver cancer, ovarian cancer;
a cancer dependent on high activity of the cholesterol synthesis pathway; and/or
a cancer associated with over-expression of NEAT1_1 and/or under-expression of NEAT1_2 that is also dependent on high activity of the cholesterol synthesis pathway chosen from the list comprising: neuroblastoma, osteosarcoma, or colorectal or non-small cell lung cancer.

The subject with the disease associated with over-expression of NEAT1_1 and/or under-expression of NEAT1_2 may be a mammal, including a human.

There is also provided a method to treat, prevent or ameliorate the effects of a disease associated with over-expression of NEAT1_1 and/or under-expression of NEAT1_2, comprising the step of:

administering to the subject an effective amount of one or more antisense oligomers or pharmaceutical composition comprising one or more antisense oligomers as described herein.

There is also provided the use of purified and isolated antisense oligomers as described herein, for the manufacture of a medicament to treat, prevent or ameliorate the effects of a disease associated with over-expression of NEAT1_1 and/or under-expression of NEAT1_2.

There is also provided a kit to treat, prevent or ameliorate the effects of a disease associated with over-expression of NEAT1_1 and/or under-expression of NEAT1_2 in a subject, which kit comprises at least an antisense oligomer as described herein and combinations or cocktails thereof, packaged in a suitable container, together with instructions for its use.

Further aspects of the invention will now be described with reference to the accompanying non-limiting Examples and Drawings.

BRIEF DESCRIPTION OF THE DRAWINGS

Further features of the present invention are more fully described in the following description of several non-limiting embodiments thereof. This description is included solely for the purposes of exemplifying the present invention. It should not be understood as a restriction on the broad summary, disclosure or description of the invention as set out above. The description will be made with reference to the accompanying drawings in which:

FIG. 6A shows RT-qPCR of NEAT1_2 levels from RNA purified from untreated SKNAS cell line, or untreated Kelly cell line. FIG. 6B shows fluorescence micrographs of representative SKNAS or Kelly cells stained with immunofluorescence for paraspeckles with NONO antibody (green) overlaid on a nuclear dye, DAPI (blue). Arrows indicate paraspeckles.

FIG. 9A shows a fluorescence micrograph of Kelly cells transfected with 2' O methyl ASOs, either control or −19+5 sequence (Boost PS ASO), then stained for paraspeckles 48 h later with FISH against NEAT1. The cell nuclei are illuminated, and the paraspeckles are indicated with an arrow. FIG. 9B is a graph of 200 cells counted for each condition showing that the average number of paraspeckles has increased with the −19+5 ASO (average of 3.6 paraspeckles per cell) compared to control (average of 1.4 paraspeckles per cell).

DESCRIPTION OF INVENTION

Detailed Description of the Invention

Antisense Oligomers

Figure 1:
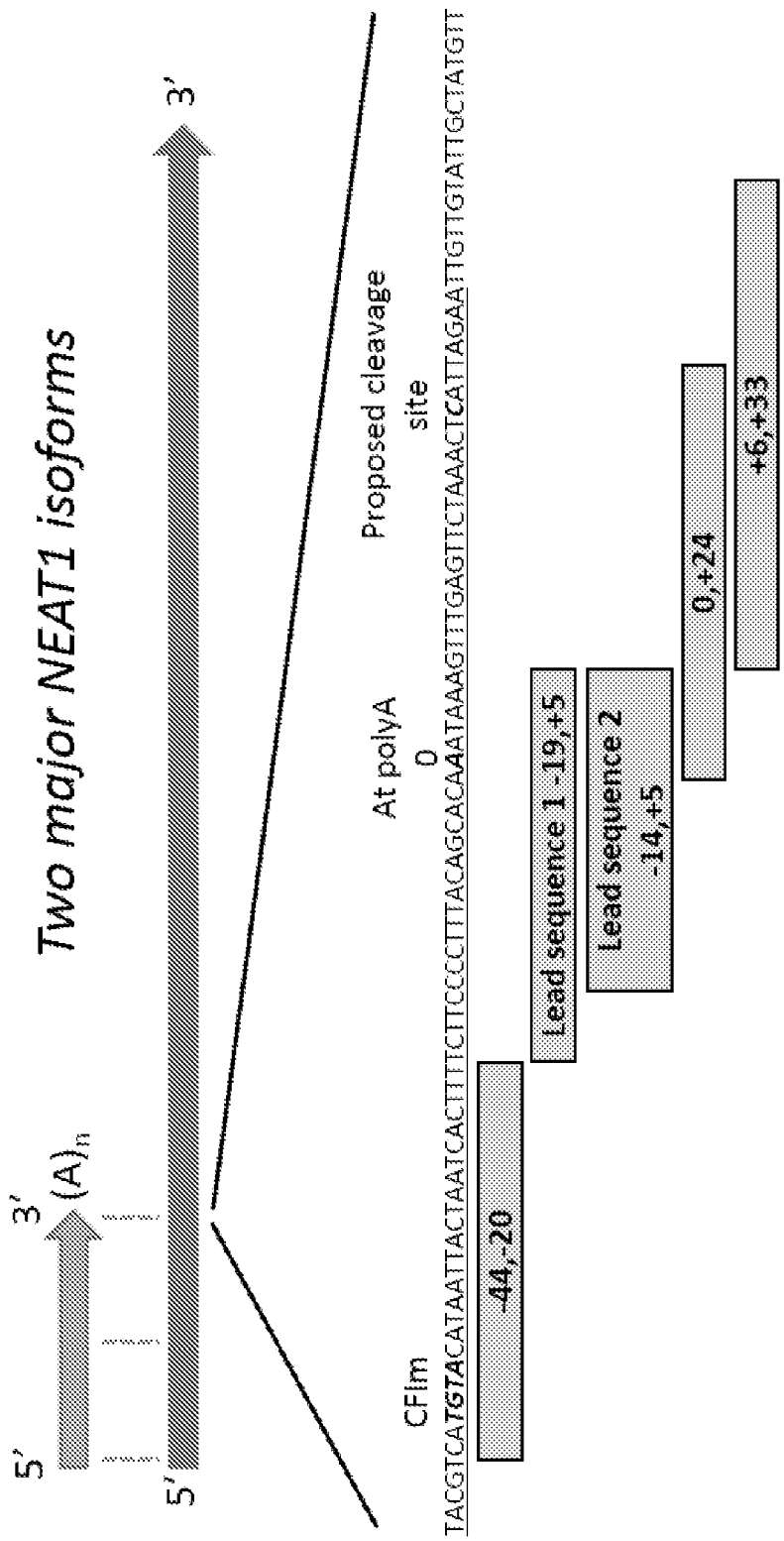
FIG. 1 is a representative figure of the two isoforms of NEAT1, and the DNA sequence (SEQ ID NO: 64) of the end of the NEAT1_1 isoform and start of the unique part of the NEAT1_2 isoform. The numbering is all relative to the first base of the poly A site. 'CFIm' are the sites recognised by the pre-messenger RNA cleavage factor I (CFIm) protein. If cleavage and polyadenylation of the NEAT1_1 isoform fails to happen, then the longer NEAT1_2 isoform is more favourably produced. The potential binding sites for the CFIm cleavage factors are indicated in bold italicised font. The first base of the polyadenylation motif is indicated in bold italicised font. The location of several relevant sequences has also been indicated.
Figure 2:
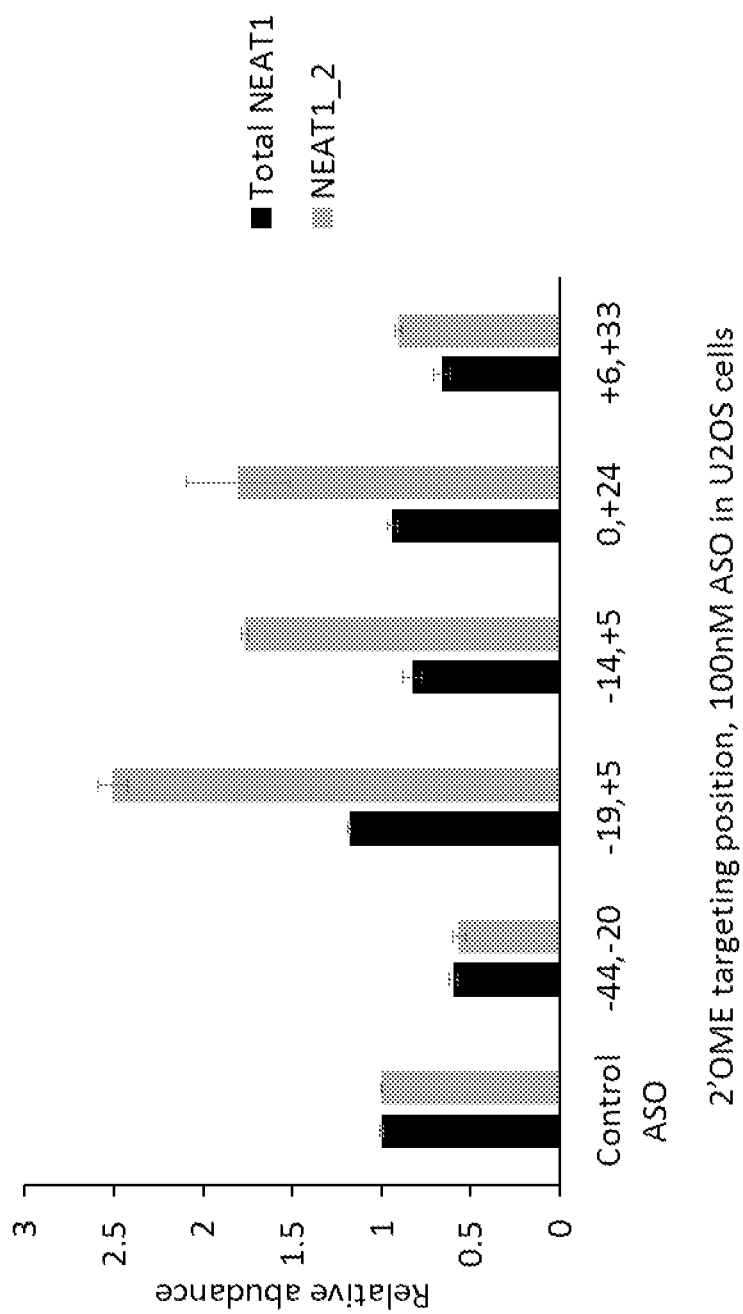
FIG. 2 is a graph of the relative abundance of total NEAT1 and NEAT1_2 RNA when U2OS osteosarcoma cells are exposed to various different ASOs, as measured by RT-qPCR. The U2OS osteosarcoma cells were transfected with 2'O-methyl modified ASOs of the sequences shown at a final concentration of 100 nM. 48 h later, RNA was isolated, reverse transcribed and qPCR carried out to detect the relative abundance of either total NEAT1 (using primers that amplify a region common to both isoforms), or NEAT12 (using primers unique to NEAT1_2).
Figure 3:
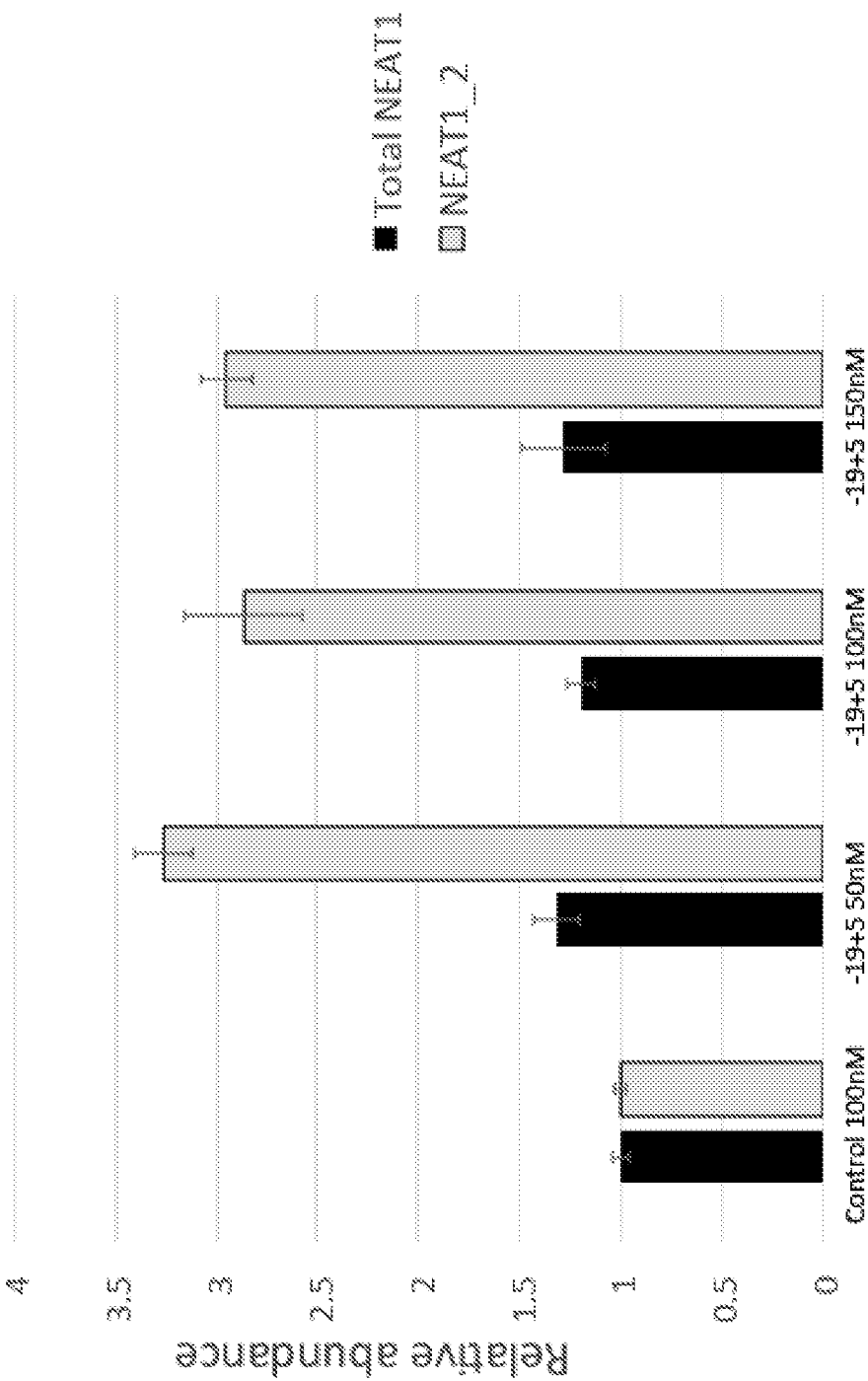
FIG. 3 is a graph of the relative abundance of total NEAT1 and NEAT1_2 RNA when U2OS osteosarcoma cells are exposed to various amounts of the −19+5 ASO, compared to control ASO. The U2OS osteosarcoma cells were transfected with 2'O-methyl modified ASOs of the sequences shown at final concentrations as indicated. 48 h later, RNA was isolated, reverse transcribed and qPCR carried out to detect the relative abundance of either total NEAT1 (using primers that amplify a region common to both isoforms), or NEAT12 (using primers unique to NEAT1_2).
Figure 4A:
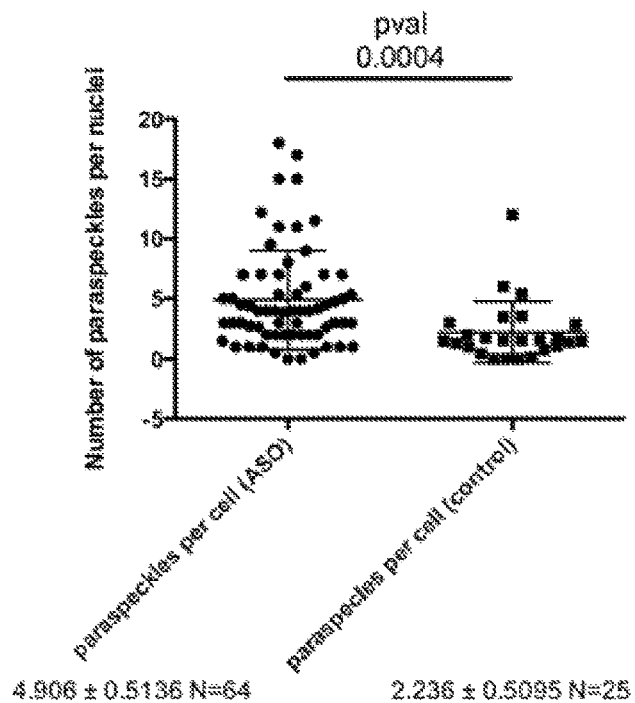
FIGS. 4A and 4B are graphs of the number and area of paraspeckles produced when U2OS cells are exposed to the −19+5 ASO, or control ASO. The −19+5 ASO sequence causes U2OS cells to increase paraspeckle numbers and size. U2OS osteosarcoma cells were transfected with 2' O methyl ASOs, either control sequence, or −19+5 sequence. 48 h later, cells were fixed and paraspeckle staining by NEAT1 FISH was performed. Paraspeckle counting (A) and area calculations (B) were carried out with Softworx software (GE Health).
Figure 4B:
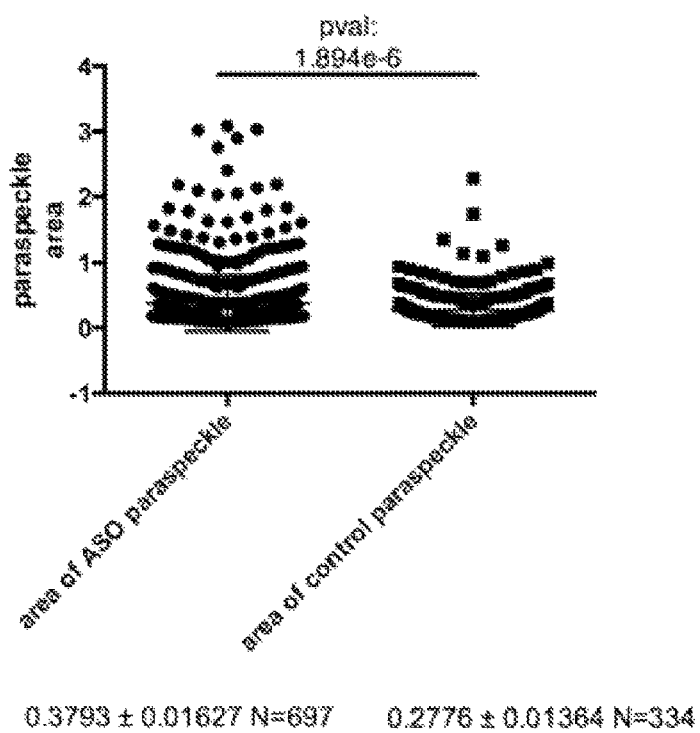
Figure 5:
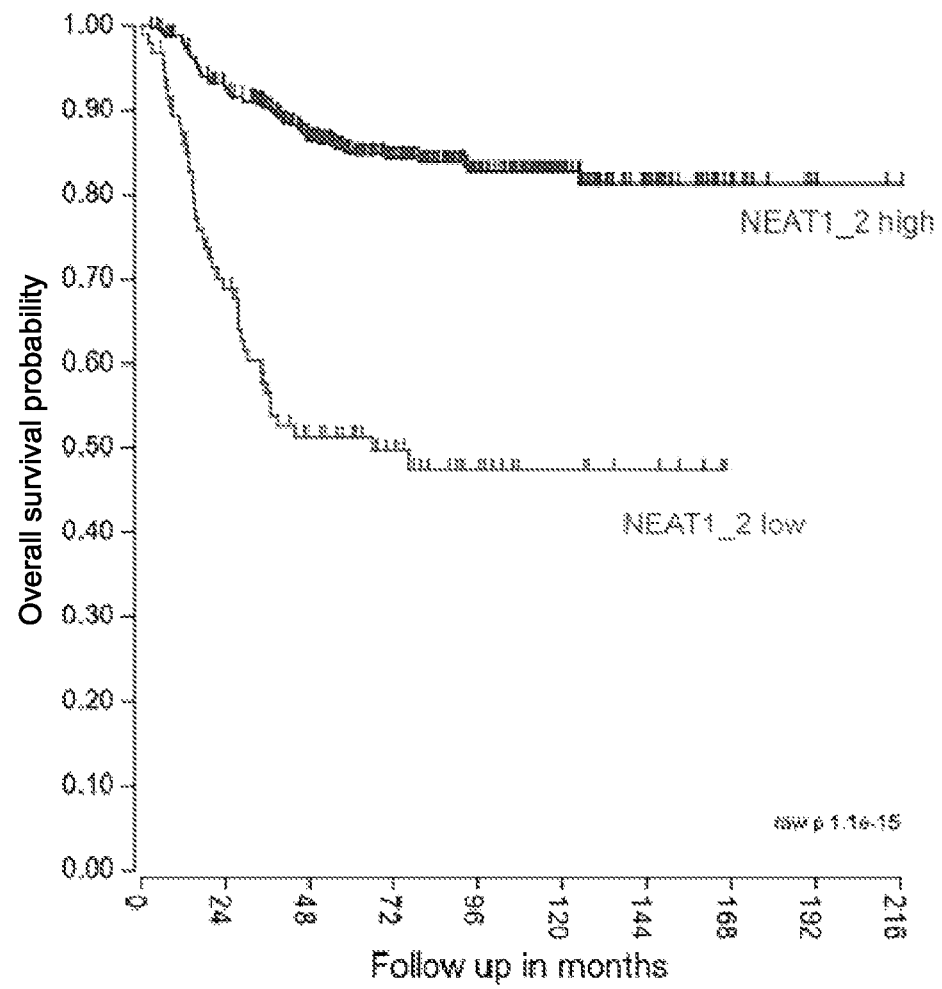
FIG. 5 is a Kaplan Meier survival curve of NEAT1_2 microarray data obtained from RNA isolated from neuroblastoma tumours indicating that higher NEAT1_2 levels are correlated with survival of subjects. High NEAT1_2 levels are associated with better outcome in neuroblastoma. The Kaplan Meier graph, obtained using the R2: Genomics analysis and visualisation platform, shows gene expression (Microarray) data of the indicated NEAT1_2 levels, as detected by probe UKv4_Hs457851.5, from tumours of 498 neuroblastoma subjects. The survival data for the subjects was used to generate this Kaplan Meier graph. The complete dataset is deposited in the microarray database with GEO ID GSE62564.
Figure 6A:
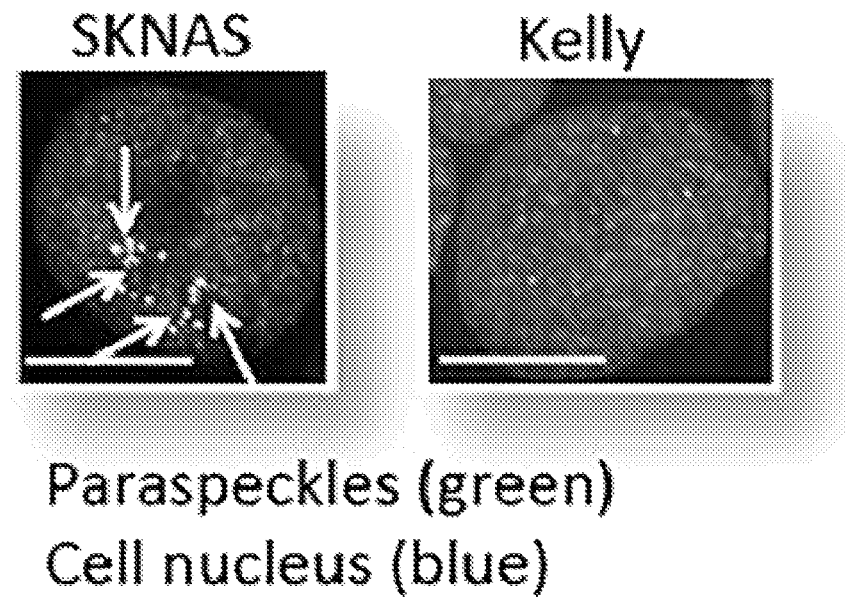
FIG. 6A is micrograph and FIG. 6B is a graph of the relative abundance of NEAT1_2 and paraspeckles in two neuroblastoma cell lines: one cell line of the aggressive MYCN-amplified sub-type (Kelly) and the other the milder non-amplified subtype (SKNAS) indicating that NEAT1_2 levels/paraspeckles are higher in the milder neuroblastoma subtype cells. The neuroblastoma cell line (Kelly) of the aggressive MYCN-amplified subtype has lower NEAT1_2 levels and fewer paraspeckles than a cell line of the milder, non-MYCN amplified neuroblastoma subtype.
Figure 6B:
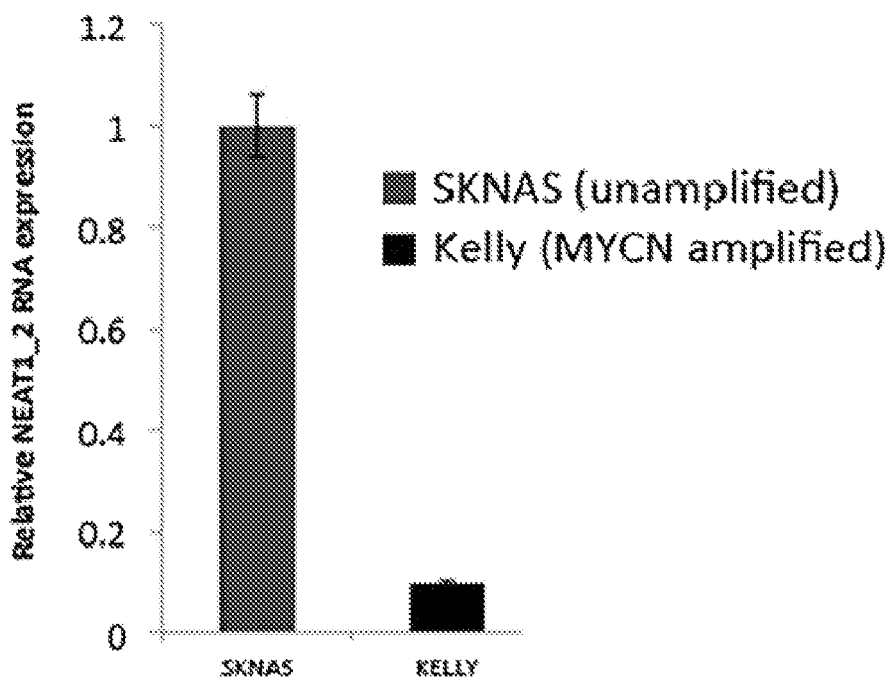
Figure 7A:
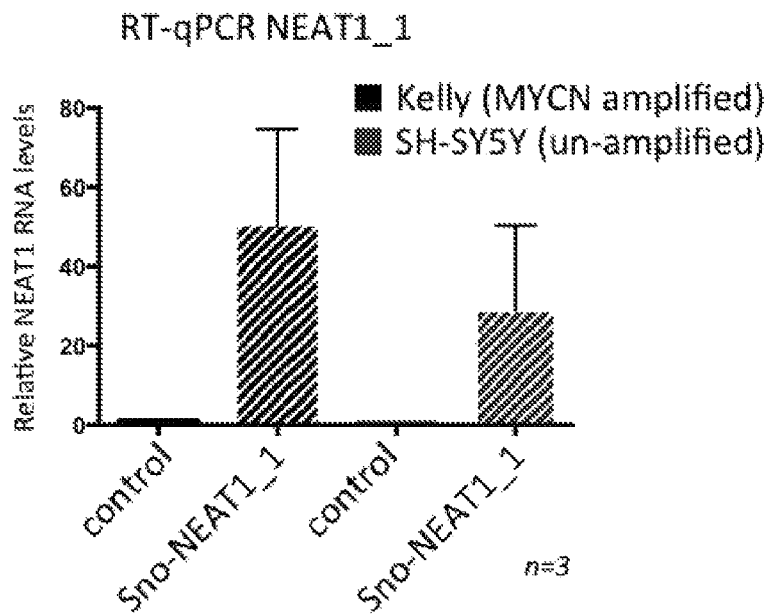
FIGS. 7A and 7B are graphs showing that over-expression of NEAT1_1 in neuroblastoma cell lines is effective at increasing NEAT1_1 levels, but has no effect on cell viability. It can be seen that over-expression of NEAT1_1 does not have an effect on cell viability in neuroblastoma. Left panel shows RT-qPCR of NEAT1_1 RNA in cells transfected with an expression plasmid encoding NEAT1_1, or an empty vector equivalent transfection. Both cell lines, Kelly and SH-SY5Y, show between 30 and 40 fold increase in NEAT1_1 levels. Right panel shows corresponding cell viability assay for the transfected cells with the same identity as the left panel.
Figure 7B:
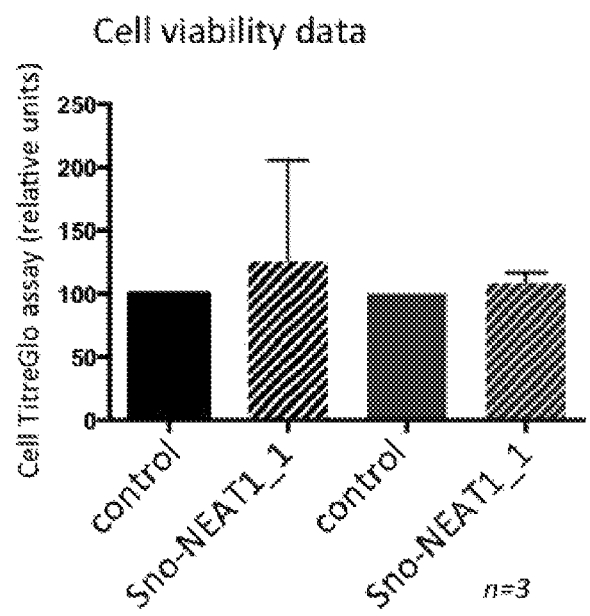
Figure 8:
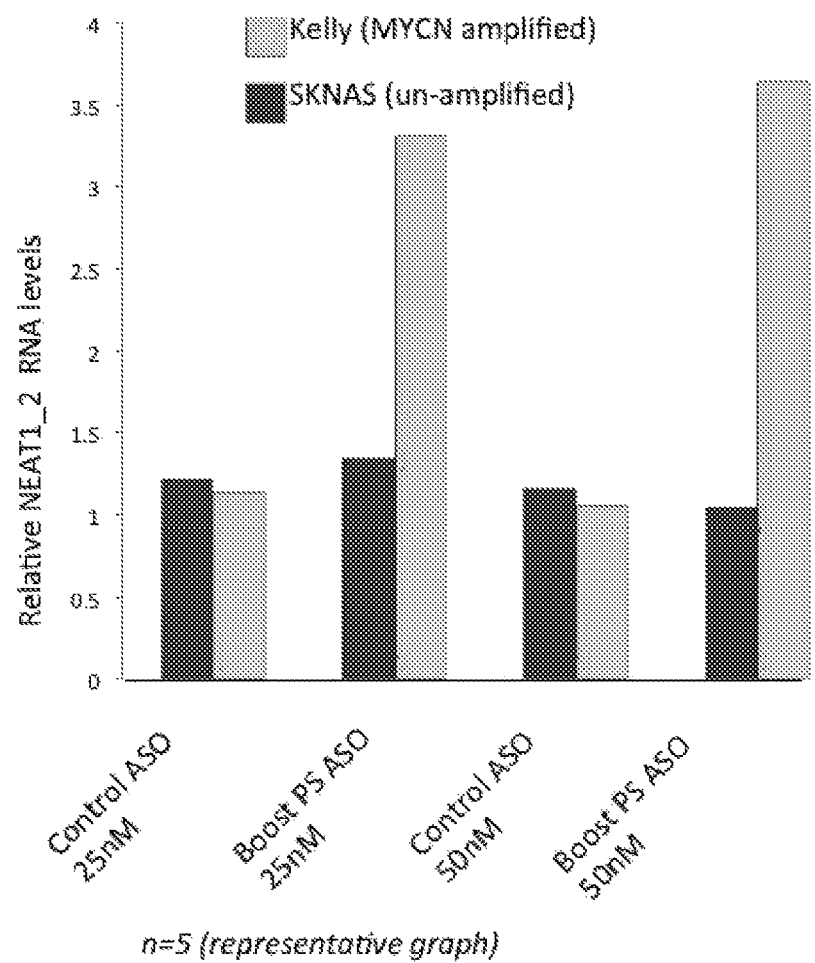
FIG. 8 is a graph of the relative abundance of NEAT1_2 in Kelly and SKNAS cell lines that have been transfected with the −19+5 ASO, or control ASO, indicating that the −19+5 ASO is capable of increasing NEAT1_2 levels in Kelly cells. The presence of −19+5 2'O methyl ASO increases NEAT1_2 levels in MYCN amplified neuroblastoma (Kelly) cell line. Kelly or SKNAS neuroblastoma cells were transfected with 2'O-methyl modified ASOs of the sequences shown (where Boost PS ASO is −19+5) at a final concentration of 25 nM, or 50 nM as indicated. 48 h later, RNA was isolated, reverse transcribed and qPCR carried out to detect the relative abundance of NEAT1_2.
Figure 9A:
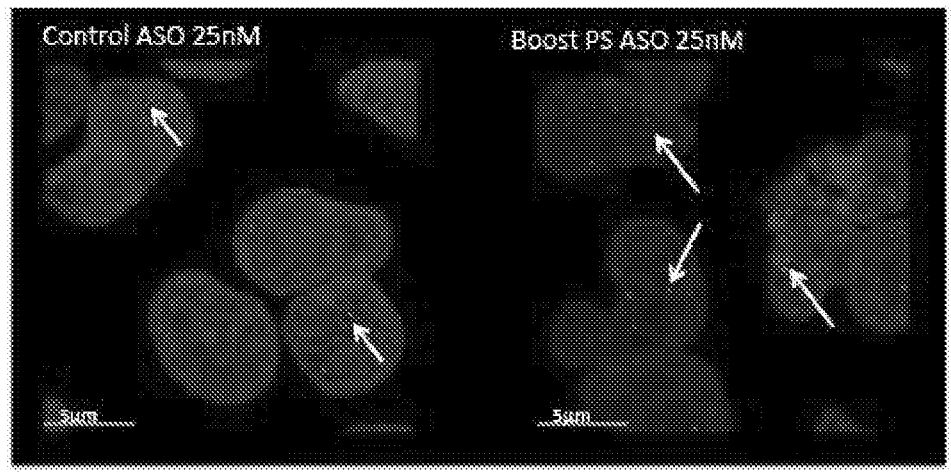
FIG. 9A is fluorescence micrograph and FIG. 9B is a graph showing that Kelly cells transfected with the −19+5 ASO (Boost PS) have more numerous paraspeckles than control ASO transfected Kelly cells. Boost PS ASO increases paraspeckles in MYCN amplified neuroblastoma (Kelly) cell line.
Figure 9B:
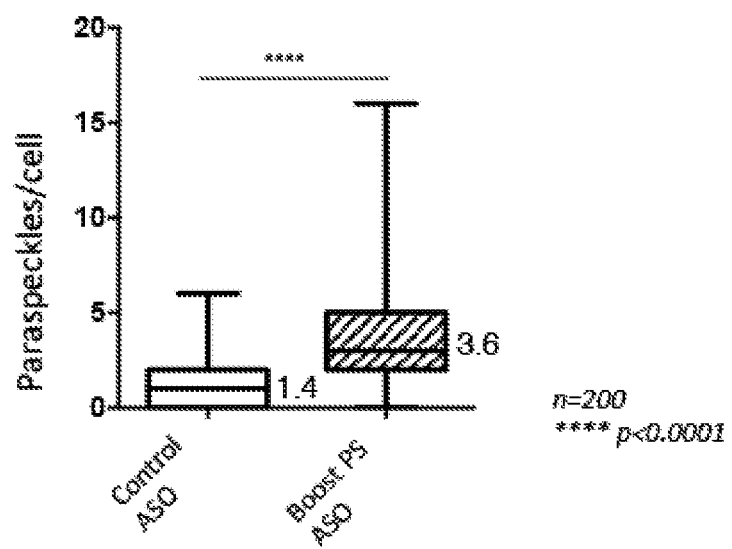
Figure 10:
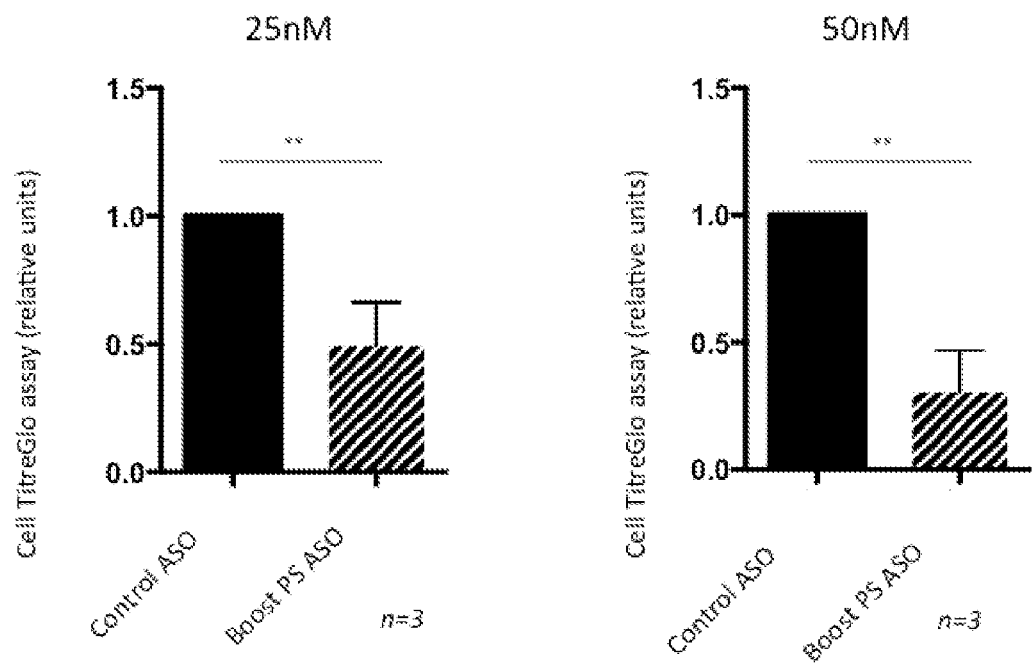
FIG. 10 is graphs of cell viability of Kelly cells transfected with different concentrations of −19+5 ASO compared to control ASO, indicating reduced cell viability in the −19+5 ASO transfected cells. The presence of −19+5 2' O methyl ASO's reduce cell viability in MYCN-amplified neuroblastoma (Kelly) cell line. Kelly cells were transfected with the indicated ASOs (where Boost PS ASO is the −19+5 sequence) at the concentrations as shown. 7 days later transfected cells were subject to the Cell titre glo cell viability assay.
Figure 11A:
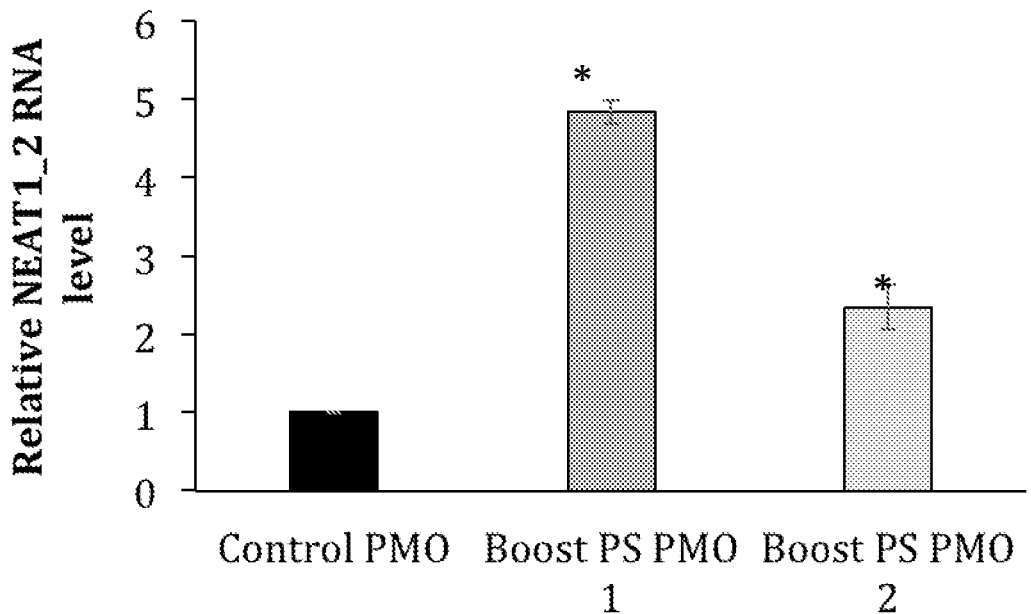
FIGS. 11A-11D are graphs showing that the same increase in NEAT1_2 levels (A) and decrease in cell viability (B) is observed in Kelly cells transfected with the −19+5 (Boost PS PMO 1), and −14+5 morpholino (Boost PS PMO 2) compared to control morpholino (Control PMO). Kelly cells were transfected with 50 nM of each morpholino sequence. 48 h later, RNA was extracted and NEAT1_2 levels assessed by RT-qPCR (A), and parallel transfected cells were assayed for cell viability with the Cell titre glo assay 7 days after transfection (B). The number of paraspeckles per nucleus (C) and sizes (D) were also measured using fluorescent microscopy. P-values shows two-tailed student t-test, equal variance. *<0.05, ***<0.001, n.s=not significant. RNA data is from one representative experiment and viability data is from three biological replicates. Statistics of paraspeckle number and sizes were generated from a minimum of 100 nuclei.
Figure 11B:
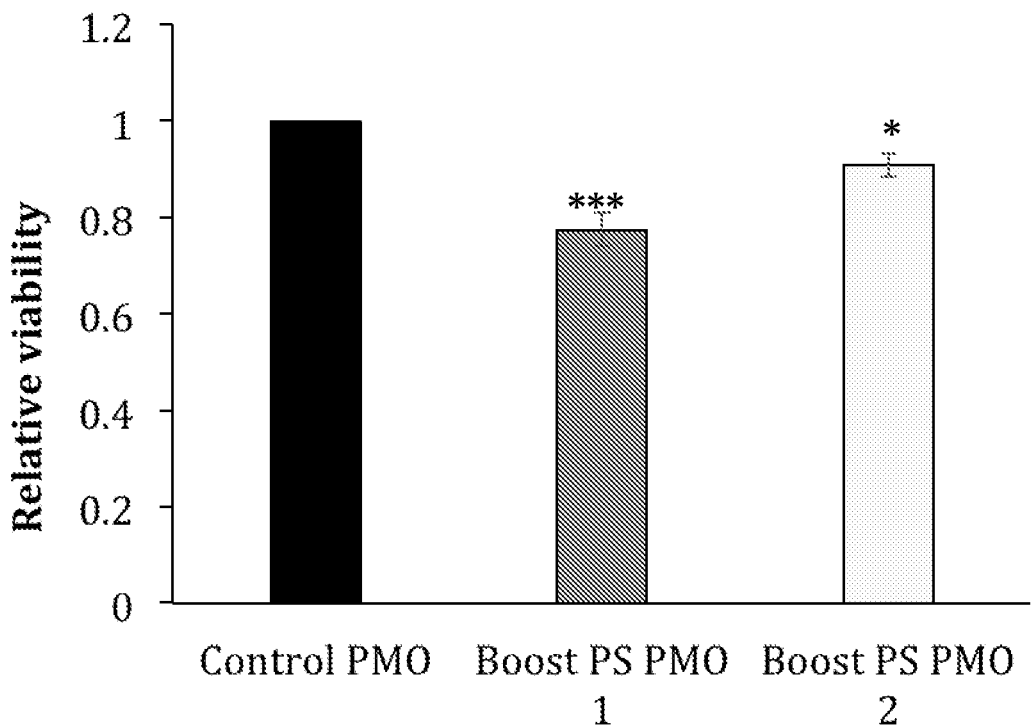
Figure 11C:
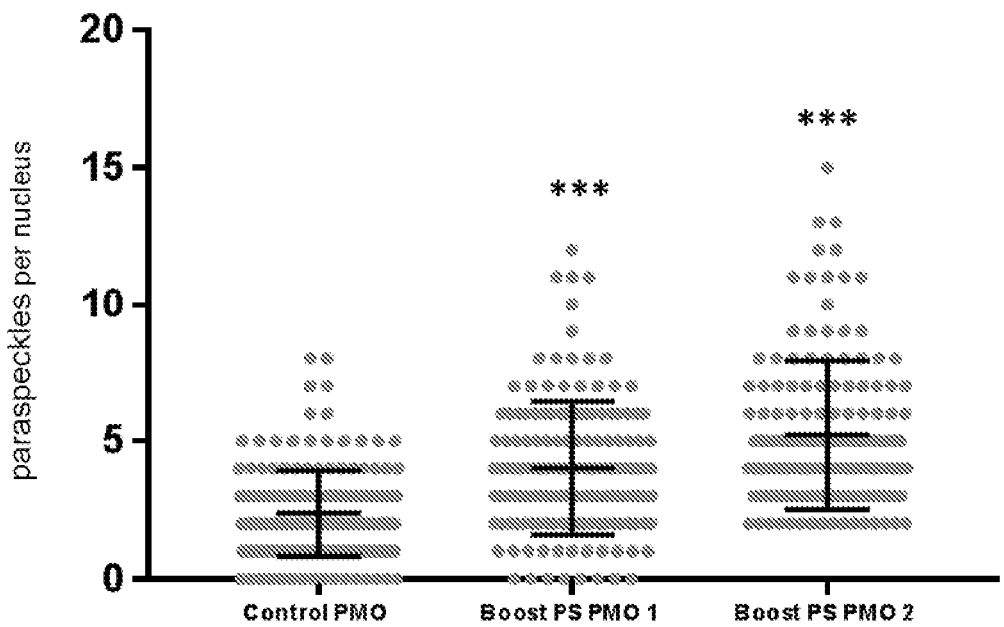
Figure 11D:
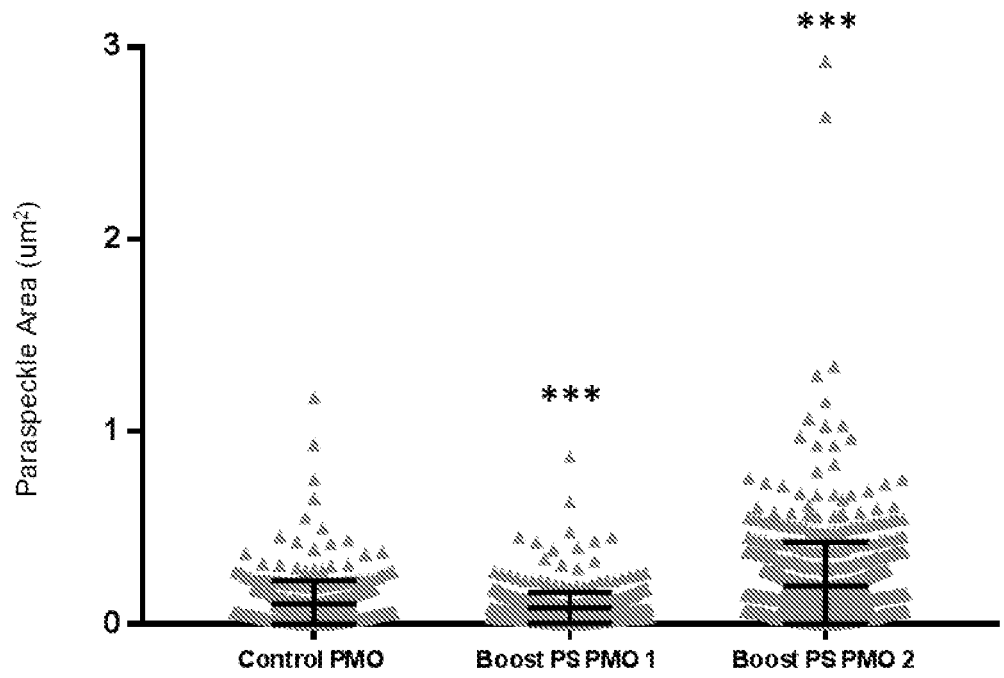
Figure 12:
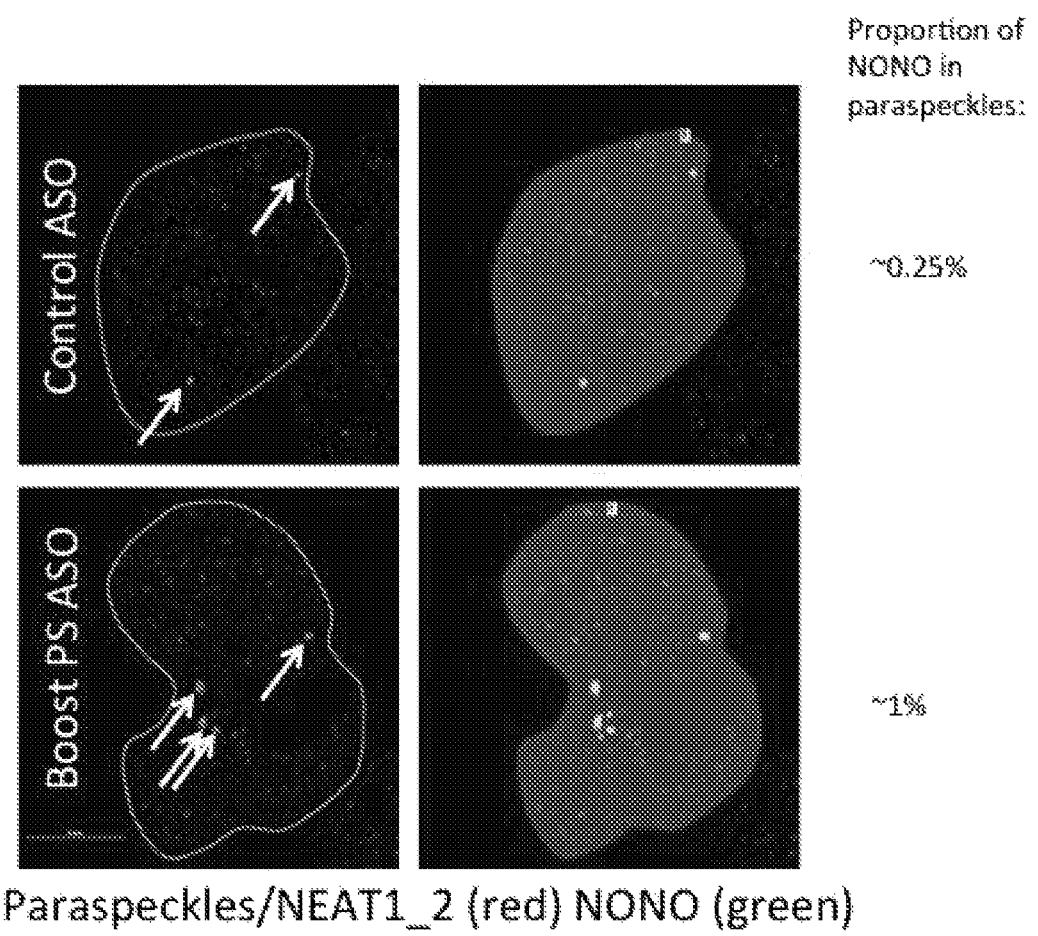
FIG. 12 is fluorescence micrograph, showing that NONO sequestration into paraspeckles is increased in Kelly cells transfected with −19+5 ASO compared to controls. Kelly cells were transfected with 2' O Methyl ASOs as indicated and 48 h later fixed and stained for paraspeckles (NEAT1 FISH, red) and NONO (immunofluorescence, green). Fluorescence micrographs of representative Kelly cells transfected with control ASO (top) or −19+5 ASO (bottom). Quantitation by thresholding paraspeckles (red NEAT1 signal) within each nucleus was carried out. For each paraspeckle, the sum of the NONO (green) fluorescence intensity for each pixel was combined and expressed as a percentage of total nuclear NONO fluorescence intensity.
Figure 13A:
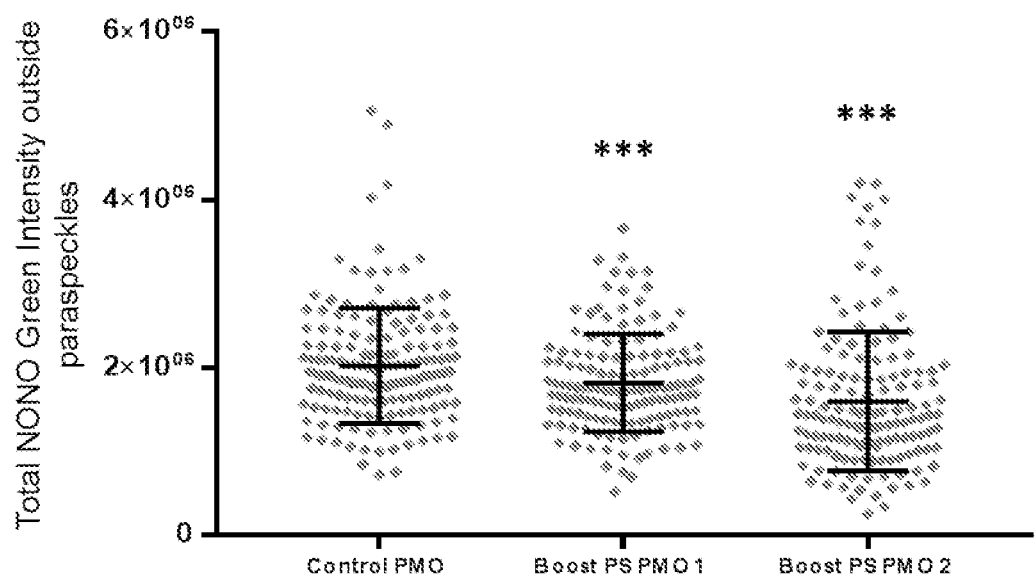
FIG. 13A and FIG. 13B are graphs of the fluorescent microscopy measurements of NONO signals in the nucleus of KELLY cells shows (A) significant reduction of free NONO in the nucleoplasm after oligo transfection (−19+5 as Boost PS PMO 1, −14+5 as Boost PS PMO 2), alongside with (B) an increased NONO in paraspeckles. Error bar shows mean±s.d. P-values shows two-tailed student t-test, equal variance. *<0.05, ***<0.001, n.s=not significant.
Figure 13B:
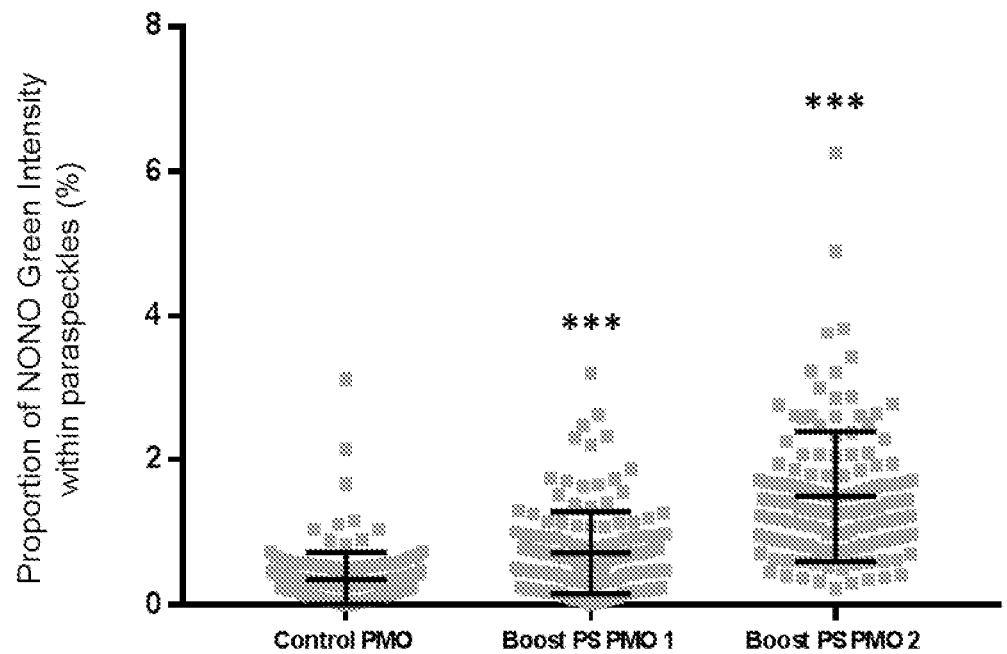
Figure 14:
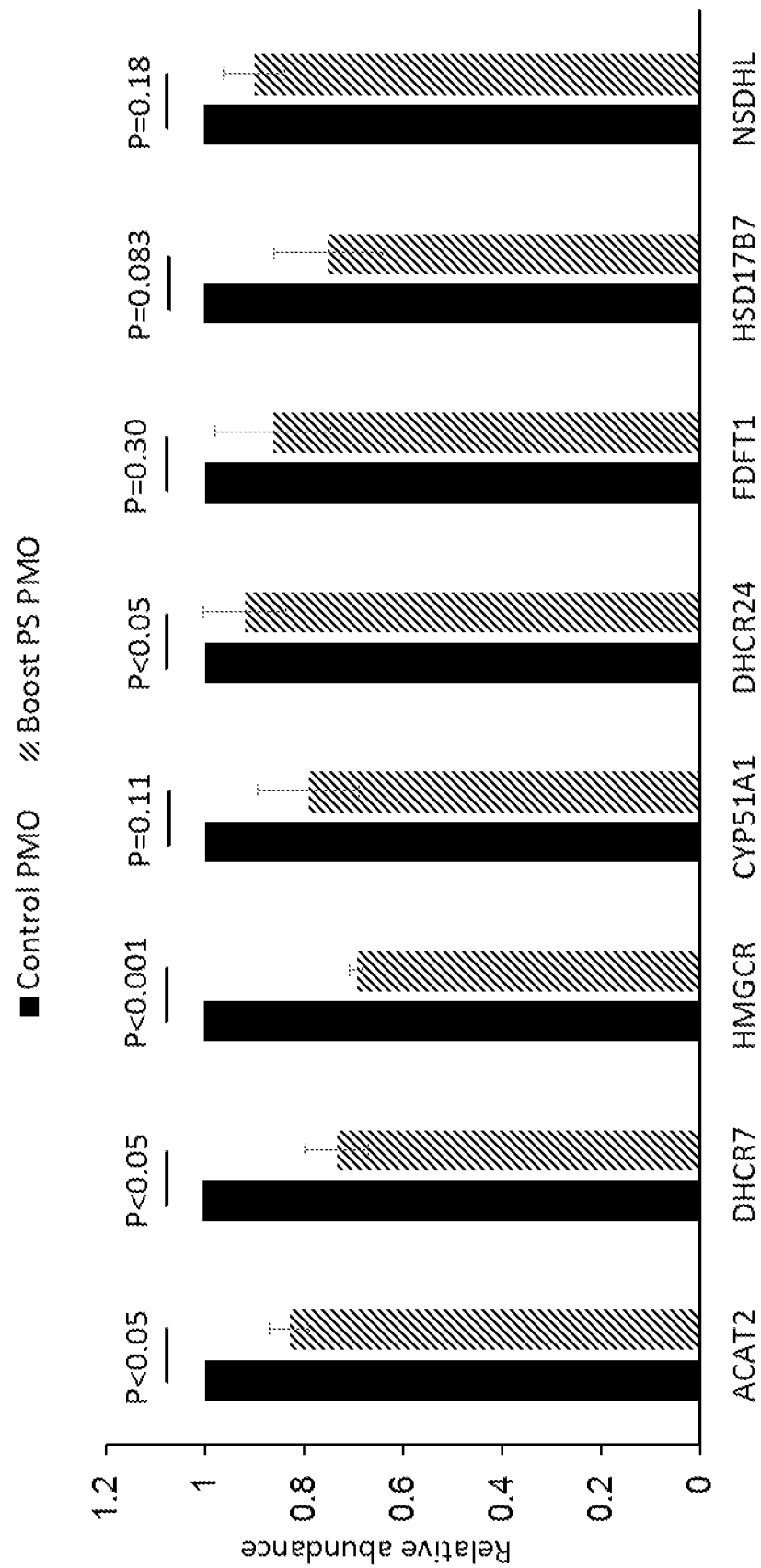
FIG. 14 is a graph of RT-qPCR measurement shows lead oligo (−19+5 as Boost PS PMO) reduces expression of several SREBP1A regulated genes in KELLY cells at 72 hours post-transfection. Reference gene: B2M. Mean±s.e.m. N=3. P-values show two-tailed student t-test, equal variance.
Figure 15:
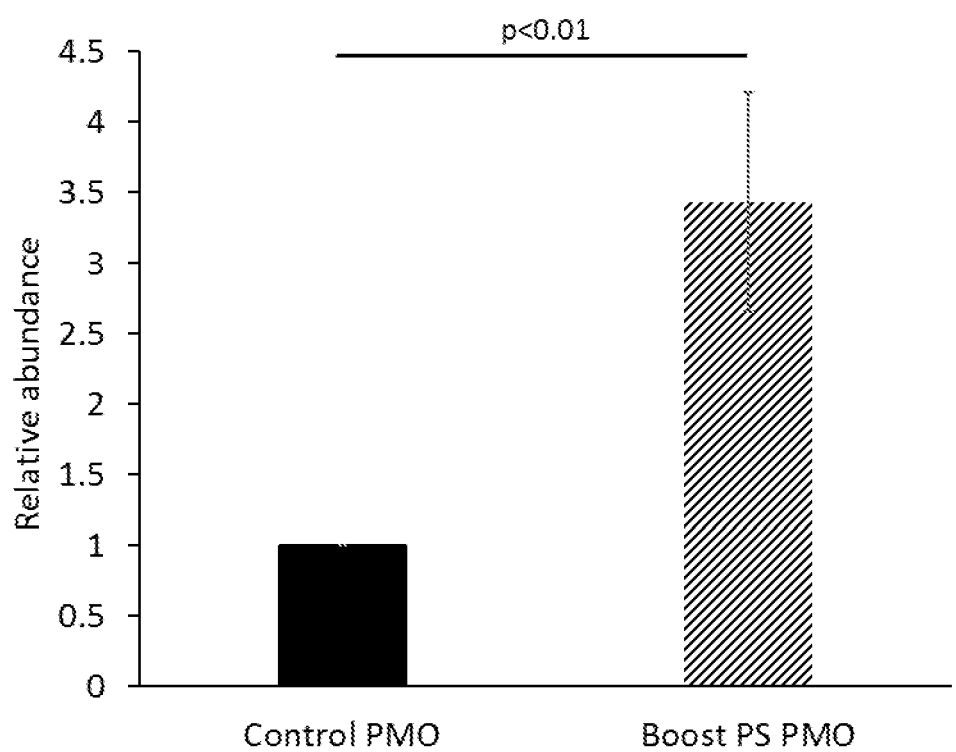
FIG. 15 is a graph of RT-qPCR measurement shows lead oligo (−19+5 as Boost PS PMO) induces NEAT1_2 level in HCT116 cells at 72 hours post-transfection. Reference gene: B2M. Mean±s.d. N=3. P-value shows two-tailed student t-test, equal variance.
Figure 16A:
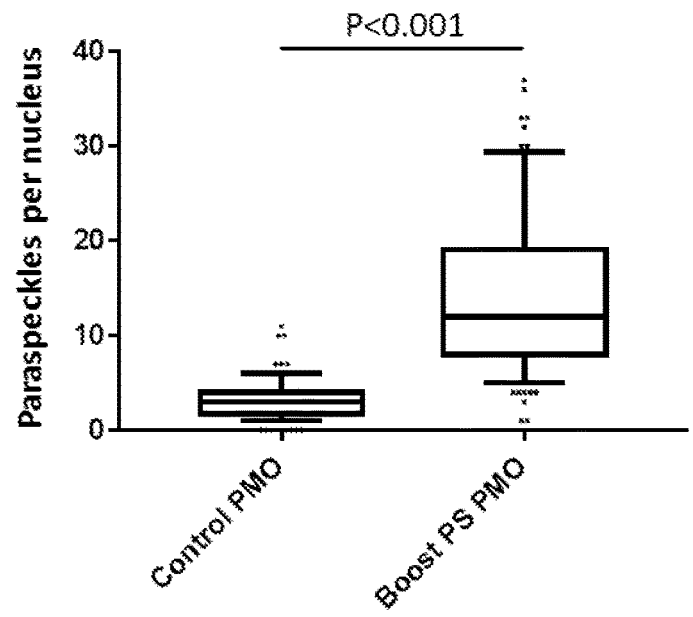
FIGS. 16A and 16B are graphs of Fluorescent microscopic measurements shows the lead oligo (−19+5 as Boost PS PMO) significantly increased both (A) number of paraspeckles per nucleus and (B) their size in HCT116 cells. RNA-FISH for NEAT12 was performed 72 hours post-transfection. Box plots represent median, 1st and 3rd quartile and 90% CI. Aligned scatter plots represent mean±s.d. P-values shows student t-test, two-tailed, equal variance.
Figure 16B:
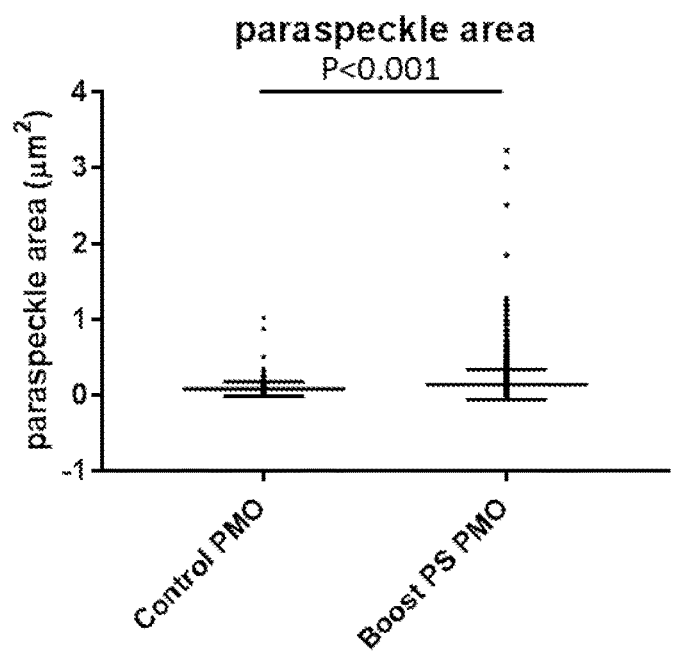
Figure 17:
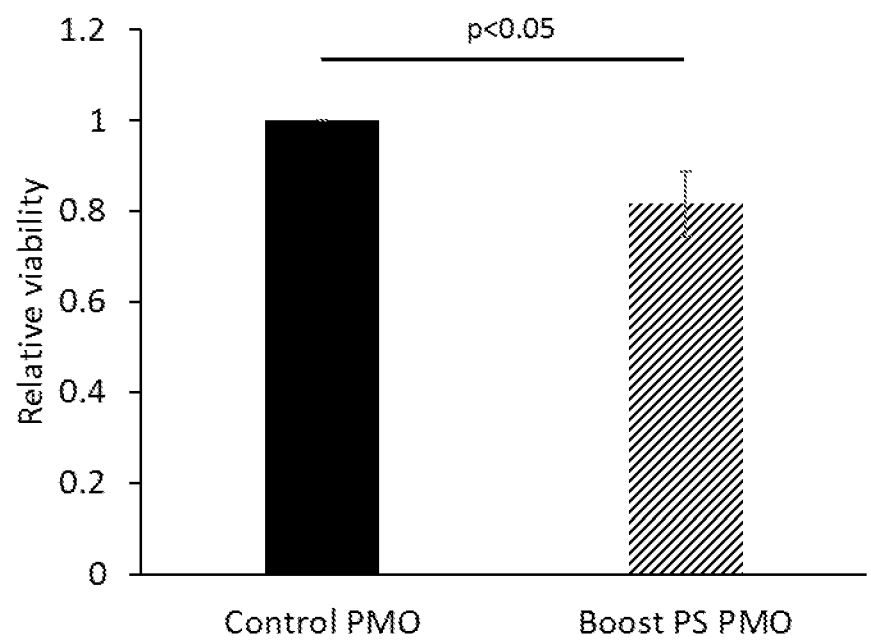
FIG. 17 is a graph of Cell relative viability measured as the confluence of cells in tissue culture plate shows less viable HCT116 cells at 72 hours post-transfection. (−19+5 as Boost PS PMO). Mean±s.e.m. N=3. P-value shows one-tailed student t-test, equal variance.
Figure 18:
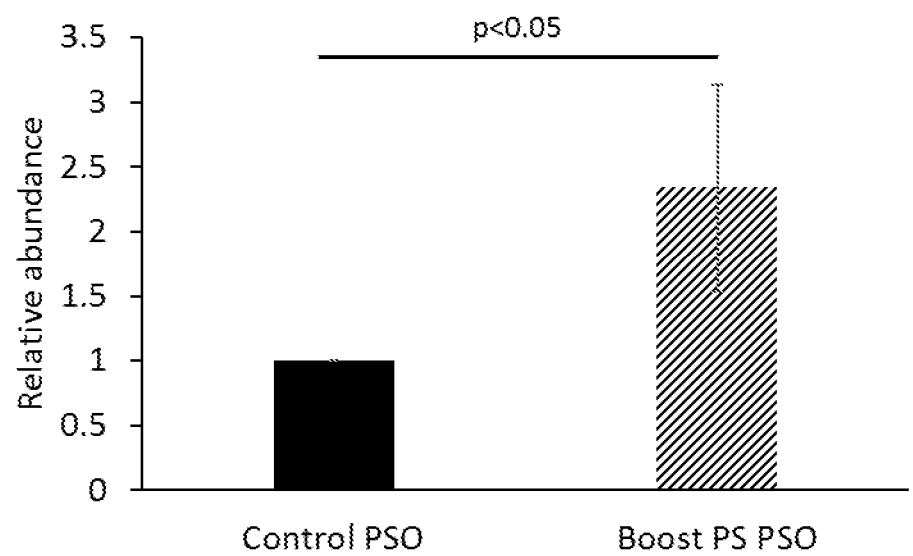
FIG. 18 is a graph of RT-qPCR measurement shows lead oligo induces NEAT1_2 level in A549 cells at 72 hours post-transfection. (−19+5 as Boost PS PMO). Reference gene: B2M. Mean±s.d. N=3. P-value shows two-tailed student t-test, equal variance.
Figure 19:
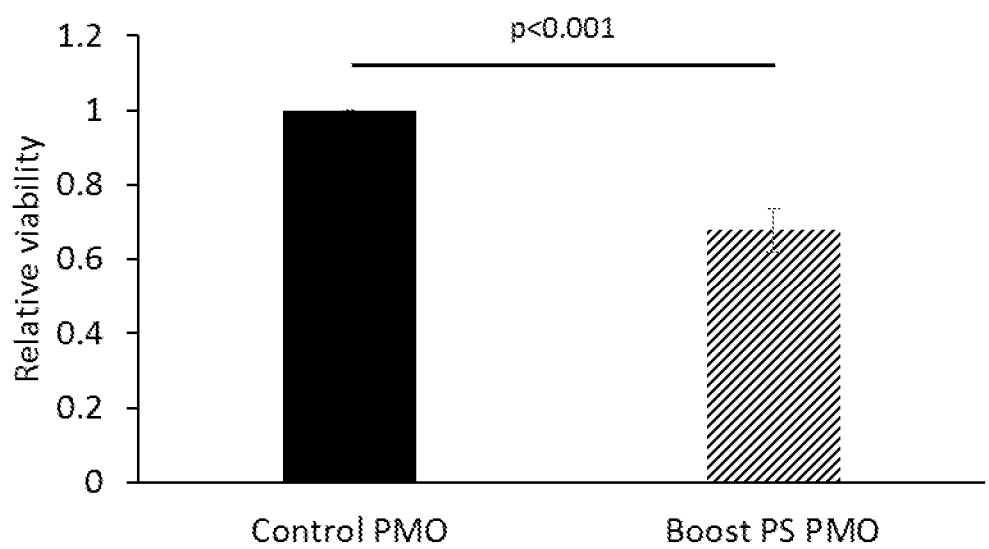
FIG. 19 is a graph of Cell relative viability as the confluence of cells in tissue culture plate shows reduced A549 cells at 72 hours post-transfection. (−19+5 as Boost PS PMO). Mean±s.e.m. N=4. P-value shows one-tailed student t-test, equal variance.
Figure 20:
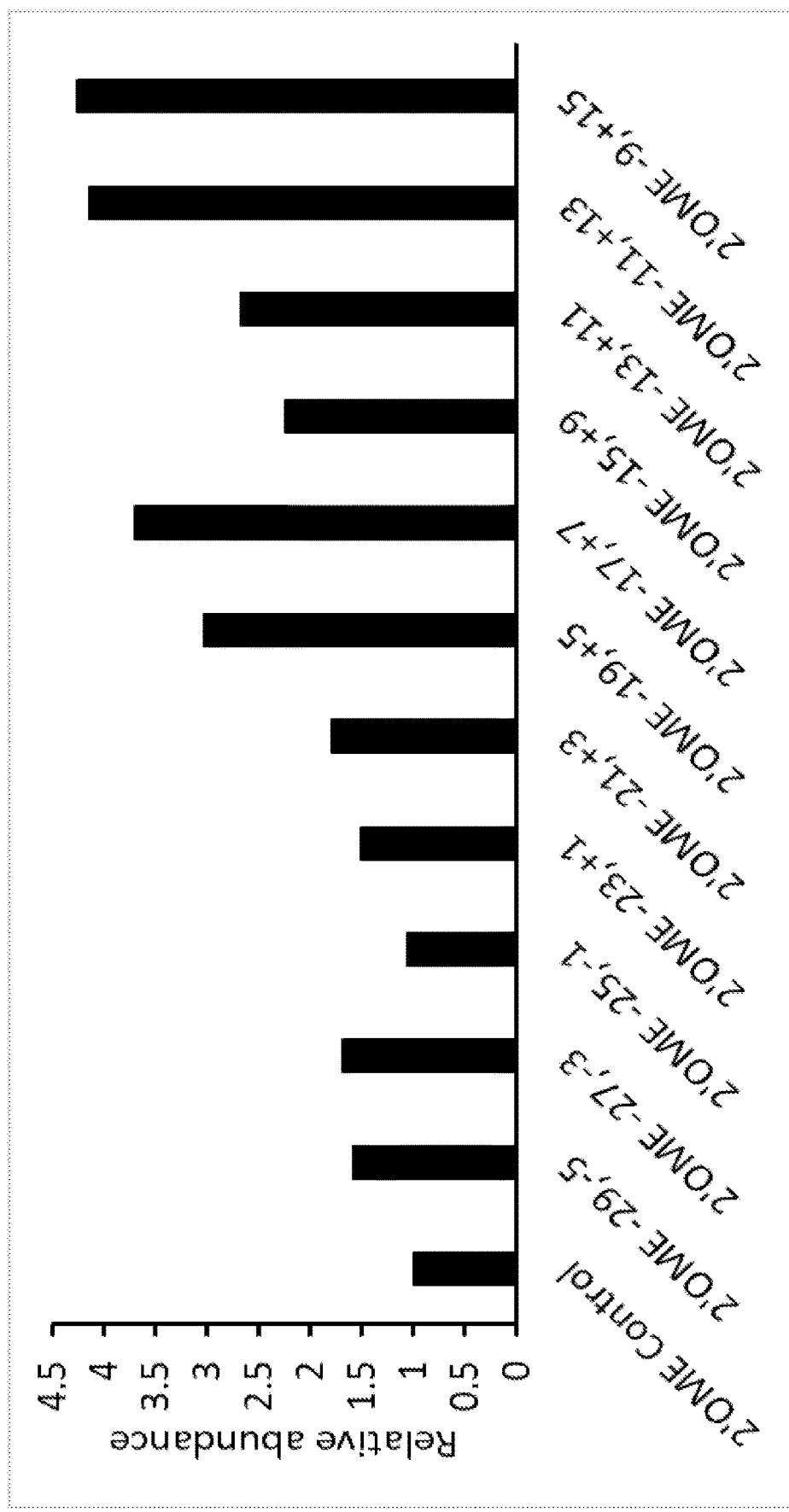
FIG. 20 is a graph of a sequence walking experiment, measured using RT-qPCR. Shows NEAT1_2 level in HCT116 cells at 72 hours post-transfection. (−19+5 as Boost PS PMO). Reference gene: B2M. Mean±s.d. N=3. P-value shows two-tailed student t-test, equal variance. Experiments were performed using a 2'OME oligo backbone

The present invention is based on the surprising discovery that the different isoforms of the lncRNA NEAT1, the RNA binding proteins that bind them and the other transcripts modulated by these same proteins, all act together to regulate gene expression in different disease contexts.

Without being held to any theory, the present invention is based on the understanding that:
  up-regulating the NEAT1_2 RNA isoform of NEAT1 RNA leads to increased sequestration of DBHS (*Drosophila* behaviour/human splicing) proteins, through the binding together of the DBHS protein and the NEAT1_2 RNA to form paraspeckle bodies;
  post-transcriptionally up-regulating the NEAT1_2 RNA isoform leads to a decrease in the amount of the NEAT1_1 RNA isoform, which has been associated with a number of cancers;
  changing the ratio of NEAT1_1:NEAT1_2 specifically by increasing the relative abundance of NEAT1_2 can have positive effects on the treatment of cancers.

DBHS proteins are known to bind to RNA and/or DNA, affecting functions such as modulating pre-mRNA splicing, activation of transcription, termination of transcription and DNA unwinding and pairing. Some transcripts are more attracted to binding with DBHS than others, and it is noted that oncogenic transcripts are particularly attractive to DBHS—they are known as "super binders".

As provided in the present invention, a paraspeckle is a nuclear body in which NEAT1_2 RNA and DBHS proteins are co-localised. Thus, the presence of increased paraspeckles indicates that increased DBHS protein is being sequestered, and less downstream activity related to oncogenic DBHS activity is occurring.

Preferably, the present invention provides antisense oligomers capable of binding to a selected target on a NEAT1 gene transcript to increase the presence of paraspeckles in a cell. This increase in the presence of paraspeckles is preferably as a result of an increase in the amount of NEAT12, leading to more sequestration of DBHS.

Free DBHS proteins (including NONO) bind to the RNA and/or DNA of oncogenic cells, such as the pre-mRNA of oncogenic gene regulatory transcripts, and affect their activity. As the presence of more NEAT1_2 leads to less free DBHS protein due to increased paraspeckle formation, the increased sequestering of DBHS proteins leads to less interaction with the oncogenic RNA/DNA and a reduction in the activity of the oncogenic pre-mRNA transcripts. As a result, the activity of the oncogenic RNA and DNA is reduced, and the growth of the oncogenic cells is reduced or stopped, preferably leading to cell death.

The DBHS protein, NONO, has many functions. One function of NONO is as a regulator of the SREB-controlled cholesterol biosynthesis pathway. Increased levels of free NONO outside paraspeckles leads to higher pathway activity. The cholesterol biosynthesis pathway may be inhibited by the present invention.

Due to this mechanism, cancers that are dependent on high activity of the cholesterol synthesis pathway, as well as cancers associated with paraspeckle insufficiency or low numbers of paraspeckles, should benefit from application of the present invention.

A number of cancers have been associated with NEAT1 expression. Preferably, the cancer to be treated or prevented by the antisense oligomers of the present invention is chosen from the list comprising: neuroblastoma, lung cancer including non-small cell lung cancer, oesophageal squamous cell carcinoma, laryngeal squamous cell carcinoma, breast cancer, prostate cancer, endometrial endometrioid adenocarcinoma, gastric cancer, glioma, thyroid carcinoma, bladder cancer, colorectal cancer, osteosarcoma, ovarian cancer.

Without being held to any theory, it is proposed that the involvement of NEAT1 in the cancers listed above may be due to over-expression of NEAT1_1; however, currently tests to distinguish the effects of NEAT1_1 from NEAT1_2 have been hampered by the similarity of their sequence. It has also been found that NEAT1_2 may act as a tumour suppressor in cancers such as neuroblastoma and colorectal cancer.

For the present invention, a cancer associated with over-expression of NEAT1_1 is a cancer that when, NEAT11 expression is reduced, the cancer's growth is reduced or inhibited. Alternatively, a cancer associated with over-expression of NEAT1_1 is a cancer where, when expression of NEAT1_1 is increased, the cancer's growth is boosted.

For the present invention, a cancer associated with under-expression of NEAT1_2 is a cancer that when, NEAT1_2 expression is increased, the cancer's growth is reduced or inhibited.

Preferably, the disease or condition treated or prevented by the antisense oligomers of the present invention is a cancer that is: (i) associated with over-expression of NEAT1_1 and/or under-expression of NEAT1_2 in a subject; and (ii) dependent on high activity of the cholesterol synthesis pathway. For example, the cancer treated by the present invention may be selected from the following cancers associated with increased cholesterol synthesis and dependency: neuroblastoma, osteosarcoma, colorectal cancer and non-small cell lung cancer.

It is possible that not all cancers associated with abnormal levels of NEAT1 are also dependent on high activity of the cholesterol synthesis pathway. Furthermore, it is possible that not all cancers dependent on high activity of the cholesterol synthesis pathway are associated with abnormal levels of NEAT1. However, if a cancer has both these features, it may be especially treatable by the present invention.

Preferably the disease associated with over-expression of NEAT1_1 and/or under-expression of NEAT1_2 in a subject is a neuroblastoma, osteosarcoma, or colorectal or non-small cell lung cancer.

In contrast to previous NEAT1 therapies, the present invention does not specifically seek to affect the overall expression of NEAT1, for example by blocking or removing all NEAT1 transcripts. Rather, it seeks to increase the production of the NEAT1_2 RNA isoform at the expense of production of the NEAT1_1 RNA isoform. The overall production of NEAT1 RNA molecules may not change significantly (although some change may occur). Alternatively, the overall amount of NEAT1 may increase, as the production of both NEAT1_1 and NEAT1_2 is increased, but in such cases the relative amount of NEAT1_2 is increased relative to NEAT1_1.

In contrast to other antisense oligomer based therapies, the present invention does not induce increased degradation of RNA via recruitment of RNase H, wherein the RNase H preferentially binds and degraded RNA bound in duplex to DNA of the NEAT1 gene. Nor does it rely on hybridization of the antisense oligomer to the NEAT1 genomic DNA or the binding of antisense oligomers to mRNA to modulate the amount of NEAT1 protein produced by interfering with normal functions such as replication, transcription, translocation and translation (as NEAT1 is non-coding).

Rather, the antisense oligomers are used to modify the binding of cleavage factors, such as CFIm proteins, to the polyadenylation site of the NEAT1 gene, wherein cleavage of the RNA at that site would result in the shorter NEAT1_1 isoform.

The binding of the ASO of the present invention to the NEAT1 RNA serves to "cover" the polyadenylation site or surrounding sequence, preventing or at least reducing the ability of cleavage factors to bind to the cleavage site and cleave the RNA to result in the NEAT11 isoform.

The target site may also include some flanking sequences around the polyadenylation site. The target site may also be near, but not overlapping the polyadenylation site, i.e. it may instead cover sequences upstream or downstream of the polyadenylation site and in these instances the ASO may not specifically cover the polyadenylation site. Localisation to near the polyadenylation site may be sufficient to disrupt the ability of cleavage factors to bind the polyadenylation site.

According to a first aspect of the invention, there is provided antisense oligomers capable of binding to a selected target on a NEAT1 gene transcript to modify pre-mRNA cleavage in a NEAT1 gene transcript or part thereof.

For example, in one aspect of the invention, there is provided an antisense oligomer of 10 to 50 nucleotides comprising a targeting sequence complementary to a region near or within the polyadenylation site of the NEAT11 pre-RNA.

The terms "antisense oligomer" and "antisense compound" and "antisense oligonucleotide" are used interchangeably and refer to a sequence of cyclic subunits, each bearing a base-pairing moiety, linked by intersubunit linkages that allow the base-pairing moieties to hybridize to a target sequence in a nucleic acid (typically an RNA) by Watson-Crick base pairing, to form a nucleic acid:oligomer heteroduplex within the target sequence. The cyclic subunits are based on ribose or another pentose sugar or, in a preferred embodiment, a morpholino group (see description of morpholino oligomers below). The oligomer may have exact or near sequence complementarity to the target sequence; variations in sequence near the termini of an oligomer are generally preferable to variations in the interior.

By "isolated" is meant material that is substantially or essentially free from components that normally accompany it in its native state. For example, an "isolated polynucleotide" or "isolated oligonucleotide," as used herein, may refer to a polynucleotide that has been purified or removed from the sequences that flank it in a naturally-occurring state, e.g., a DNA fragment that is removed from the sequences that are adjacent to the fragment in the genome. The term "isolating" as it relates to cells refers to the purification of cells (e.g., fibroblasts, lymphoblasts) from a source subject (e.g., a subject with a polynucleotide repeat disease). In the context of mRNA or protein, "isolating" refers to the recovery of mRNA or protein from a source, e.g., cells.

An antisense oligomer can be said to be "directed to" or "targeted against" a target sequence with which it hybridizes. In certain embodiments, the target sequence includes a region including the polyadenylation site and surrounding regions. The target sequence is typically a region including an AUG start codon of an mRNA, a Translation Suppressing Oligomer, or splice site of a pre-processed mRNA, a Splice Suppressing Oligomer (SSO). The target sequence for a splice site may include an mRNA sequence having its 5' end 1 to about 25 base pairs downstream of a normal splice acceptor junction in a pre-processed mRNA. A preferred target sequence is any region of a pre-processed mRNA that includes a splice site or is contained entirely within an exon coding sequence or spans a splice acceptor or donor site. An oligomer is more generally said to be "targeted against" a biologically relevant target, such as a protein, virus, or bacteria, when it is targeted against the nucleic acid of the target in the manner described above.

As used herein, "sufficient length" refers to an antisense oligonucleotide that is complementary to at least 8, more typically 8-30, contiguous nucleobases in a target NEAT pre-mRNA. In some embodiments, an antisense of sufficient length includes at least 8, 9, 10, 11, 12, 13, 14, or 15 contiguous nucleobases in the target NEAT pre-mRNA. In other embodiments an antisense of sufficient length includes at least 16, 17, 18, 19, 20, 21, 22, 23, 24, or 25 contiguous nucleobases in the target NEAT pre-mRNA. An antisense oligonucleotide of sufficient length has at least a minimal number of nucleotides to be capable of specifically hybridizing to exon 53. Preferably an oligonucleotide of sufficient length is from about 10 to about 50 nucleotides in length, including oligonucleotides of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and 40 or more nucleotides. In one embodiment, an oligonucleotide of sufficient length is from 10 to about 30 nucleotides in length. In another embodiment, an oligonucleotide of sufficient length is from 15 to about 25 nucleotides in length. In yet another embodiment, an oligonucleotide of sufficient length is from 20 to 30, or 20 to 50, nucleotides in length. In yet another embodiment, an oligonucleotide of sufficient length is from 22 to 28, 25 to 28, 24 to 29 or 25 to 30 nucleotides in length.

In certain embodiments, the antisense oligomer has sufficient sequence complementarity to a target RNA (i.e., the RNA for which cleavage factor binding site selection is modulated) to block a region of a target RNA (e.g., pre-mRNA) in an effective manner. In exemplary embodiments, such blocking of NEAT1 pre-RNA serves to reduce cleavage, either by masking a binding site for a native protein that would otherwise modulate cleavage and/or by altering the structure of the targeted RNA. In some embodiments, the target RNA is target pre-RNA (e.g., NEAT1 gene pre-RNA).

An antisense oligomer having a sufficient sequence complementarity to a target RNA sequence to modulate cleavage factor binding of the target RNA means that the antisense oligomer has a sequence sufficient to trigger the masking of a binding site for a native protein that would otherwise cause cleavage to the shorter NEAT1 isoform and/or alters the three-dimensional structure of the targeted RNA.

Selected antisense oligomers can be made shorter, e.g., about 12 bases, or longer, e.g., about 50 bases, and include a small number of mismatches, as long as the sequence is sufficiently complementary to effect cleavage factor binding modulation upon hybridization to the target sequence, and optionally forms with the RNA ASO heteroduplex having a Tm of 45° C. or greater.

Preferably, the antisense oligomer is selected from the group comprising the sequences set forth in Table 1.

In certain embodiments, the degree of complementarity between the target sequence and antisense oligomer is sufficient to form a stable duplex. The region of complementarity of the antisense oligomers with the target RNA sequence may be as short as 8-11 bases, but can be 12-15 bases or more, e.g., 10-50 bases, 10-40 bases, 12-30 bases, 12-25 bases, 15-25 bases, 12-20 bases, or 15-20 bases, including all integers in between these ranges. An antisense oligomer of about 16-17 bases is generally long enough to have a unique complementary sequence. In certain embodiments, a minimum length of complementary bases may be required to achieve the requisite binding Tm, as discussed herein.

In certain embodiments, oligonucleotides as long as 50 bases may be suitable, where at least a minimum number of bases, e.g., 10-12 bases, are complementary to the target sequence. In general, however, facilitated or active uptake in cells is optimized at oligonucleotide lengths of less than about 30 bases. For phosphorodiamidate morpholino oligomer (PMO) antisense oligomers described further herein, an optimum balance of binding stability and uptake generally occurs at lengths of 18-25 bases. Included are antisense oligomers (e.g., PMOs, PMO-X, PNAs, LNAs, 2'-OMe) that consist of about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 bases.

In certain embodiments, antisense oligomers may be 100% complementary to the target sequence, or may include mismatches, e.g., to accommodate variants, as long as a heteroduplex formed between the oligonucleotide and target sequence is sufficiently stable to withstand the action of cellular nucleases and other modes of degradation which may occur in vivo. Hence, certain oligonucleotides may have about or at least about 70% sequence complementarity, e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence complementarity, between the oligonucleotide and the target sequence.

Mismatches, if present, are typically less destabilizing toward the end regions of the hybrid duplex than in the middle. The number of mismatches allowed will depend on the length of the oligonucleotide, the percentage of G:C base pairs in the duplex, and the position of the mismatch(es) in the duplex, according to well understood principles of duplex stability. Although such an antisense oligomer is not necessarily 100% complementary to the target sequence, it is effective to stably and specifically bind to the target sequence, such that cleavage factor binding to the target pre-RNA is modulated.

The stability of the duplex formed between an antisense oligomer and a target sequence is a function of the binding Tm and the susceptibility of the duplex to cellular enzymatic cleavage. The Tm of an oligonucleotide with respect to complementary-sequence RNA may be measured by conventional methods, such as those described by Hames et al., Nucleic Acid Hybridization, IRL Press, 1985, pp. 107-108 or as described in Miyada C. G. and Wallace R. B., 1987, Oligonucleotide Hybridization Techniques, Methods Enzymol. Vol. 154 pp. 94-107. In certain embodiments, antisense oligomers may have a binding Tm, with respect to a complementary-sequence RNA, of greater than body temperature and preferably greater than about 45° C. or 50° C. Tm's in the range 60-80° C. or greater are also included.

Additional examples of variants include antisense oligomers having about or at least about 70% sequence identity or homology, e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity or homology, over the entire length of any of SEQ ID NOS: 1-55.

More specifically, there is provided an antisense oligomer capable of binding to a selected target site to reduce or eliminate cleavage in a NEAT1 gene transcript or part thereof. The antisense oligomer is preferably selected from those provided in Table 1.

The modification of pre-mRNA cleavage factor binding preferably reduces cleavage of the NEAT1 RNA into the shorter NEAT1_1 isoform, and/or increases the production of the NEAT1_2 isoform of the RNA.

The antisense oligomer induced cleavage factor blockage of the present invention need not completely or even substantially reduce the amount of NEAT1_1 produced. However, preferably it at least increases the amount of NEAT1_2 produced.

TABLE 1

SEQ ID listing of antisense oligomers modifying cleavage of NEAT1.

| SEQIDNO | Co-ordinates | Sequence |
|---|---|---|
| 1 | NEAT1(+12+36) | ACAACAATTCTAATGAGTTTAGAAC |
| 2 | NEAT1(+11+35) | CAACAATTCTAATGAGTTTAGAACT |
| 3 | NEAT1(+10+34) | AACAATTCTAATGAGTTTAGAACTC |
| 4 | NEAT1(+9+33) | ACAATTCTAATGAGTTTAGAACTCA |
| 5 | NEAT1(+8+32) | CAATTCTAATGAGTTTAGAACTCAA |
| 6 | NEAT1(+7+31) | AATTCTAATGAGTTTAGAACTCAAA |
| 7 | NEAT1(+6+30) | ATTCTAATGAGTTTAGAACTCAAAC |
| 8 | NEAT1(+5+29) | TTCTAATGAGTTTAGAACTCAAAC*T* |
| 9 | NEAT1(+4+28) | TCTAATGAGTTTAGAACTCAAAC*TT* |
| 10 | NEAT1(+3+27) | CTAATGAGTTTAGAACTCAAAC*TTT* |
| 11 | NEAT1(+2+26) | TAATGAGTTTAGAACTCAAAC*TTT* |
| 12 | NEAT1(+1+25) | AATGAGTTTAGAACTCAAAC*TTT T* |
| 13 | NEAT1(0+24) | ATGAGTTTAGAACTCAAAC*TTT TT* |
| 14 | NEAT1(-1+23) | TGAGTTTAGAACTCAAAC*TTT TTT* |
| 15 | NEAT1(-2+22) | GAGTTTAGAACTCAAAC*TTT TTTG* |
| 16 | NEAT1(-3+21) | AGTTTAGAACTCAAAC*TTT TTTGT* |
| 17 | NEAT1(-4+20) | GTTTAGAACTCAAAC*TTT TTTGTG* |
| 18 | NEAT1(-5+19) | TTTAGAACTCAAAC*TTT TTTGTGC* |
| 19 | NEAT1(-6+18) | TTAGAACTCAAAC*TTT TTTGTGCT* |
| 20 | NEAT1(-7+17) | TAGAACTCAAAC*TTT TTTGTGCTG* |
| 21 | NEAT1(-8+16) | AGAACTCAAAC*TTT TTTGTGCTGT* |
| 22 | NEAT1(-9+15) | GAACTCAAAC*TTT TTTGTGCTGTA* |
| 23 | NEAT1(-10+14) | AACTCAAAC*TTT T TGTGCTGTAA* |
| 24 | NEAT1(-11+13) | ACTCAAAC*TTT TTTGTGCTGTAAA* |
| 25 | NEAT1(-12+12) | CTCAAAC*TTT TTTGTGCTGTAAAG* |
| 26 | NEAT1(-13+11) | TCAAAC*TTT TTTGTGCTGTAAAGG* |
| 27 | NEAT1(-14+10) | CAAAC*TTT TTTGTGCTGTAAAGGG* |
| 28 | NEAT1(-15+9) | AAAC*TTT TTTGTGCTGTAAAGGGG* |
| 29 | NEAT1(-16+8) | AAC*TTT TTTGTGCTGTAAAGGGGA* |
| 30 | NEAT1(-17+7) | AC*TTT TTTGTGCTGTAAAGGGGAA* |
| 31 | NEAT1(-18+6) | C*TTT TTTGTGCTGTAAAGGGGAAG* |
| 32 | NEAT1(-19+5) | *TTT TTTGTGCTGTAAAGGGGAAGA* |
| 33 | NEAT1(-20+4) | *TT TTTGTGCTGTAAAGGGGAAGA* |
| 34 | NEAT1(-21+3) | *T TTTGTGCTGTAAAGGGGAAGA*AA |
| 35 | NEAT1(-22+2) | *TTTGTGCTGTAAAGGGGAAGA*AAA |
| 36 | NEAT1(-23+1) | *TTTGTGCTGTAAAGGGGAAGA*AAAG |
| 37 | NEAT1(-24+0) | *TTGTGCTGTAAAGGGGAAGA*AAAAGT |
| 38 | NEAT1(-25-1) | *TGTGCTGTAAAGGGGAAGA*AAAGTG |
| 39 | NEAT1(-26-2) | *GTGCTGTAAAGGGGAAGA*AAAGTGA |
| 40 | NEAT1(-27-3) | *TGCTGTAAAGGGGAAGA*AAAGTGAT |
| 41 | NEAT1(-28-4) | *GCTGTAAAGGGGAAGA*AAAGTGATT |
| 42 | NEAT1(-29-5) | *CTGTAAAGGGGAAGA*AAAGTGATTA |

TABLE 1-continued

SEQ ID listing of antisense oligomers modifying cleavage of NEAT1.

| SEQIDNO | Co-ordinates | Sequence |
|---|---|---|
| 43 | NEAT1(-30-6) | *TGTAAAGGGGAAGA*AAAGTGATTAG |
| 44 | NEAT1(-31-7) | *GTAAAGGGGAAGA*AAAAGTGATTAGT |
| 45 | AO-E1 | AGCAACATACCAGTACTTTCAACCA |
| 46 | AO-E2 | CATACAGAGCAACATACCAGTACTT |
| 47 | AO-E3 | GTAACAGAATTAGTTCTTACCATAC |
| 48 | AO-E4 | TTAGTAATTATGTACATGACGTAAC |
| 49 | AO-E5 | GAGAAATGTAACATAGCAATACAAC |
| 50 | AO-E6 | AAGGCAATGTGATAGGGGTCGAGAA |
| 51 | AO-E7 | ATACATCCAAAGTCGTTATGAAGGC |
| 52 | AO-E8 | ATGAAGTATCATCCAAAGTCGAATT |
| 53 | Mismatch1 (-19+5) | TTTẠTTTGTGCTGTAAAGGGAAGA |
| 54 | Mismatch2 (-19+5) | TTTẠTTTGTGCTGTAAAGGTGAAGA |
| 55 | NEAT1(-14+5) | *TTTẠTTTGTGCTGTAAAGGG* |

Reverse complement sequence shown 5-3'.
The reference point (0) set at first base of polyadenylation signal; hence "+" refers to sequences downstream of A⁰ATAAA and "-" indicates sequences upstream More preferably, the ASO used in the present invention is chosen from the list comprising SEQ ID NO: 13 to 42, and 55 or SEQ ID NO: 13, 22, 24, 26, 28, 30, 32, 34, 36, 38, 40, 42 or 55. More preferably, the ASO used in the present invention is SEQ ID NO: 22, 32 or 55.

Method of Use

The invention further provides a method for manipulating cleavage factor binding in a NEAT1 gene transcript, the method including the step of:
 a) providing one or more of the antisense oligomers as described herein and allowing the oligomer(s) to bind to a target nucleic acid site.

According to yet another aspect of the invention, there is provided a cleavage factor binding modification target nucleic acid sequence for NEAT1 comprising the DNA equivalents of the nucleic acid sequences selected from the group consisting of SEQ ID NOs: 1-55, and sequences complementary thereto.

Designing antisense oligomers to completely mask the polyadenylation site may not be necessary to generate a change in the proportion of cleaved RNA. Furthermore, the inventors have discovered that size or length of the antisense oligomer itself is not always a primary factor when designing antisense oligomers. With some targets, antisense oligomers as short as 20 bases were able to induce cleavage modification, in certain cases more efficiently than other longer (eg 25 bases) oligomers directed to the same region.

More specifically, the antisense oligomer may be selected from those set forth in Table 1. The sequences are preferably selected from the group consisting of any one or more of any one or more of SEQ ID NOs: 1-55, and combinations or cocktails thereof. This includes sequences which can hybridise to such sequences under stringent hybridisation conditions, sequences complementary thereto, sequences containing modified bases, modified backbones, and functional truncations or extensions thereof which possess or modulate RNA processing activity in a NEAT1 gene transcript.

Preferably, the ASO used in the present invention is chosen from the list comprising SEQ ID NO: 22 or 32 to 55; or more preferably SEQ ID NO: 22, 32 or 55.

The oligomer and the DNA, cDNA or RNA are complementary to each other when a sufficient number of corresponding positions in each molecule are occupied by nucleotides which can hydrogen bond with each other. Thus, "specifically hybridisable" and "complementary" are terms which are used to indicate a sufficient degree of complementarity or pairing such that stable and specific binding occurs between the oligomer and the DNA, cDNA or RNA target. It is understood in the art that the sequence of an antisense oligomer need not be 100% complementary to that of its target sequence to be specifically hybridisable. An antisense oligomer is specifically hybridisable when binding of the compound to the target DNA or RNA molecule interferes with the normal function of the target DNA or RNA product, and there is a sufficient degree of complementarity to avoid non-specific binding of the antisense oligomer to non-target sequences under conditions in which specific binding is desired, i.e., under physiological conditions in the case of in vivo assays or therapeutic treatment, and in the case of in vitro assays, under conditions in which the assays are performed.

Selective hybridisation may be under low, moderate or high stringency conditions, but is preferably under high stringency. Those skilled in the art will recognise that the stringency of hybridisation will be affected by such conditions as salt concentration, temperature, or organic solvents, in addition to the base composition, length of the complementary strands and the number of nucleotide base mismatches between the hybridising nucleic acids. Stringent temperature conditions will generally include temperatures in excess of 30° C., typically in excess of 37° C., and preferably in excess of 45° C., preferably at least 50° C., and typically 60° C.-80° C. or higher. Stringent salt conditions will ordinarily be less than 1000 mM, typically less than 500 mM, and preferably less than 200 mM. However, the combination of parameters is much more important than the measure of any single parameter. An example of stringent hybridisation conditions is 65° C. and 0.1×SSC (1×SSC=0.15 M NaCl, 0.015 M sodium citrate pH 7.0). Thus, the antisense oligomers of the present invention may include oligomers that selectively hybridise to the sequences provided in Table 1, or SEQ ID NOs: 1-55.

At a given ionic strength and pH, the Tm is the temperature at which 50% of a target sequence hybridizes to a complementary polynucleotide. Such hybridization may occur with "near" or "substantial" complementarity of the antisense oligomer to the target sequence, as well as with exact complementarity.

Typically, selective hybridisation will occur when there is at least about 55% identity over a stretch of at least about 14 nucleotides, preferably at least about 65%, more preferably at least about 75% and most preferably at least about 90%, 95%, 98% or 99% identity with the nucleotides of the antisense oligomer. The length of homology comparison, as described, may be over longer stretches and in certain embodiments will often be over a stretch of at least about nine nucleotides, usually at least about 12 nucleotides, more usually at least about 20, often at least about 21, 22, 23 or 24 nucleotides, at least about 25, 26, 27 or 28 nucleotides, at least about 29, 30, 31 or 32 nucleotides, at least about 36 or more nucleotides.

Thus, the antisense oligomer sequences of the invention preferably have at least 75%, more preferably at least 85%, more preferably at least 86, 87, 88, 89 or 90% homology to the sequences shown in the sequence listings herein. More preferably there is at least 91, 92, 93 94, or 95%, more preferably at least 96, 97, 98% or 99%, homology. Generally, the shorter the length of the antisense oligomer, the greater the homology required to obtain selective hybridisation. Consequently, where an antisense oligomer of the invention consists of less than about 30 nucleotides, it is preferred that the percentage identity is greater than 75%, preferably greater than 85, 86, 87, 88, 89, 90, 91, 92, 93, 94, 95%, 96, 97, 98% or 99% compared with the antisense oligomers set out in the sequence listings herein. Nucleotide homology comparisons may be conducted by sequence comparison programs such as the GCG Wisconsin Bestfit program or GAP (Deveraux et al., 1984, Nucleic Acids Research 12, 387-395). In this way sequences of a similar or substantially different length to those cited herein could be compared by insertion of gaps into the alignment, such gaps being determined, for example, by the comparison algorithm used by GAP.

The antisense oligomer of the present invention may have regions of reduced homology, and regions of exact homology with the target sequence. It is not necessary for an oligomer to have exact homology for its entire length. For example, the oligomer may have continuous stretches of at least 4 or 5 bases that are identical to the target sequence, preferably continuous stretches of at least 6 or 7 bases that are identical to the target sequence, more preferably continuous stretches of at least 8 or 9 bases that are identical to the target sequence. The oligomer may have stretches of at least 10, 11, 12, 13, 14, 15, 16, 17, 18, 19, 20, 21, 22, 23, 24, 25 or 26 bases that are identical to the target sequence. The remaining stretches of oligomer sequence may be intermittently identical with the target sequence; for example, the remaining sequence may have an identical base, followed by a non-identical base, followed by an identical base. Alternatively (or as well) the oligomer sequence may have several stretches of identical sequence (for example 3, 4, 5 or 6 bases) interspersed with stretches of less than perfect homology. Such sequence mismatches will preferably have no or very little loss of cleavage modifying activity.

The term "modulate" or "modulates" includes to "increase" or "decrease" one or more quantifiable parameters, optionally by a defined and/or statistically significant amount. The terms "increase" or "increasing," "enhance" or "enhancing," or "stimulate" or "stimulating" refer generally to the ability of one or antisense oligomers or compositions to produce or cause a greater physiological response (i.e., downstream effects) in a cell or a subject relative to the response caused by either no antisense oligomer or a control compound.

By "enhance" or "enhancing," or "increase" or "increasing," or "stimulate" or "stimulating," refers generally to the ability of one or antisense compounds or compositions to produce or cause a greater physiological response (i.e., downstream effects) in a cell or a subject, as compared to the response caused by either no antisense compound or a control compound. A measurable physiological response may include increased expression of a functional form of a NEAT1 protein, among other responses apparent from the understanding in the art and the description herein. An "increased" or "enhanced" amount is typically a "statistically significant" amount, and may include an increase that is 1.1, 1.2, 2, 3, 4, 5, 6, 7, 8, 9, 10, 15, 20, 30, 40, 50 or more times (e.g., 500, 1000 times) (including all integers and decimal points in between and above 1), e.g., 1.5, 1.6, 1.7, 1.8, etc.) the amount produced by no antisense compound (the absence of an agent) or a control compound.

The terms "decreasing" or "decrease" refer generally to the ability of one or antisense oligomers or compositions to produce or cause a reduced physiological response (i.e., downstream effects) in a cell or a subject relative to the response caused by either no antisense oligomer or a control compound. The term "reduce" or "inhibit" may relate generally to the ability of one or more antisense compounds of the invention to "decrease" a relevant physiological or cellular response, such as a symptom of a disease or condition described herein, as measured according to routine techniques in the diagnostic art. Relevant physiological or cellular responses (in vivo or in vitro) will be apparent to persons skilled in the art, and may include reductions in the symptoms or pathology of a NEAT1 related condition. A "decrease" in a response may be statistically significant as compared to the response produced by no antisense compound or a control composition, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%. 55%. 60%. 65%, 70%, 75%, 80%, 85%, 90%, 95%, or 100% decrease, including all integers in between.

Relevant physiological or cellular responses (in vivo or in vitro) will be apparent to persons skilled in the art, and may include increases in the presence of NEAT1_2 RNA isoform, decreases in the amount of NEAT1_1 isoform, alteration of the ration of NEAT1_2:NEAT1_1, increases in the amount of paraspeckles, decreases in the amount of free DBHS proteins. An "increased" or "enhanced" amount is typically a statistically significant amount, and may include an increase that is 1.1, 1.2, 2, 3, 4, 5, 6, 7, 8, 9, 10, 15, 20, 30, 40, 50 or more times (e.g., 500, 1000 times) (including all integers and decimal points in between and above 1, e.g., 1.5, 1.6, 1.7. 1.8) the amount produced by no antisense oligomer (the absence of an agent) or a control compound. The term "reduce" or "inhibit" may relate generally to the ability of one or more antisense oligomers or compositions to "decrease" a relevant physiological or cellular response, such as a symptom of a disease or condition described herein, as measured according to routine techniques in the diagnostic art. Relevant physiological or cellular responses (in vivo or in vitro) will be apparent to persons skilled in the art, and may include reductions in the symptoms or pathology of a disease associated with paraspeckles, such as neuroblastoma. A "decrease" in a response may be statistically significant as compared to the response produced by no antisense oligomer or a control composition, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease, including all integers in between.

The length of an antisense oligomer may vary, as long as it is capable of binding selectively to the intended location within the pre-RNA molecule. The length of such sequences can be determined in accordance with selection procedures described herein. Generally, the antisense oligomer will be from about 10 nucleotides in length, up to about 50 nucleotides in length. It will be appreciated, however, that any length of nucleotides within this range may be used in the method. Preferably, the length of the antisense oligomer is between 10 and 40, 10 and 35, 15 to 30 nucleotides in length or 20 to 30 nucleotides in length, most preferably about 25 to 30 nucleotides in length. For example, the oligomer may be 20, 21, 22, 23, 24, 25, 26, 27, 28, 29 or 30 nucleotides in length.

As used herein, an "antisense oligomer" or "ASO" refers to a linear sequence of nucleotides, or nucleotide analogs, that allows the nucleobase to hybridize to a target sequence in an RNA by Watson-Crick base pairing, to form an oligonucleotide:RNA heteroduplex within the target sequence. The terms "antisense oligomer", "antisense oligonucleotide", "oligomer" and "antisense compound" may be used interchangeably to refer to an oligonucleotide. The cyclic subunits may be based on ribose or another pentose sugar or, in certain embodiments, a morpholino group (see description of morpholino oligonucleotides below). Also contemplated are peptide nucleic acids (PNAs), locked nucleic acids (LNAs), and 2'-O-Methyl oligonucleotides, among other antisense agents known in the art.

In some embodiments, the antisense oligonucleotides have the chemical composition of a naturally occurring nucleic acid molecule, i.e., the antisense oligonucleotides do not include a modified or substituted base, sugar, or inter-subunit linkage.

In a preferred embodiment, the antisense oligonucleotides of the present invention are non-naturally occurring nucleic acid molecules, or "oligonucleotide analogs". For example, non-naturally occurring nucleic acids can include one or more non-natural base, sugar, and/or inter-subunit linkage, e.g., a base, sugar, and/or linkage that has been modified or substituted with respect to that found in a naturally occurring nucleic acid molecule. Exemplary modifications are described below. In some embodiments, non-naturally occurring nucleic acids include more than one type of modification, e.g. sugar and base modifications, sugar and linkage modifications, base and linkage modifications, or base, sugar, and linkage modifications. For example, in some embodiments, the antisense oligonucleotides contain a non-natural (e.g. modified or substituted) base. In some embodiments, the antisense oligonucleotides contain a non-natural (e.g. modified or substituted) sugar. In some embodiments, the antisense oligonucleotides contain a non-natural (e.g. modified or substituted) inter-subunit linkage. In some embodiments, the antisense oligonucleotides contain more than one type of modification or substitution, e.g. a non-natural base and/or a non-natural sugar, and/or a non-natural inter-subunit linkage.

Thus included are non-naturally-occurring antisense oligomershaving (i) a modified backbone structure, e.g., a backbone other than the standard phosphodiester linkage found in naturally-occurring oligo- and polynucleotides, and/or (ii) modified sugar moieties, e.g., morpholino moieties rather than ribose or deoxyribose moieties. Oligonucleotide analogs support bases capable of hydrogen bonding by Watson-Crick base pairing to standard polynucleotide bases, where the analog backbone presents the bases in a manner to permit such hydrogen bonding in a sequence-specific fashion between the oligonucleotide analog molecule and bases in a standard polynucleotide (e.g., single-stranded RNA or single-stranded DNA). Preferred analogs are those having a substantially uncharged, phosphorus containing backbone.

One method for producing antisense oligomers is the methylation of the 2' hydroxyribose position and the incorporation of a phosphorothioate backbone produces molecules that superficially resemble RNA but that are much more resistant to nuclease degradation, although persons skilled in the art of the invention will be aware of other forms of suitable backbones that may be useable in the objectives of the invention.

To avoid degradation of pre-RNA during duplex formation with the antisense oligomers, the antisense oligomers used in the method may be adapted to minimise or prevent cleavage by endogenous RNase H. Antisense molecules that do not activate RNase H can be made in accordance with known techniques (see, e.g., U.S. Pat. No. 5,149,797). Such antisense molecules, which may be deoxyribonucleotide or ribonucleotide sequences, simply contain any structural modification which sterically hinders or prevents binding of RNase H to a duplex molecule containing the oligonucleotide as one member thereof, which structural modification does not substantially hinder or disrupt duplex formation. Because the portions of the oligonucleotide involved in duplex formation are substantially different from those portions involved in RNase H binding thereto, numerous antisense molecules that do not activate RNase H are available. This property is highly preferred, as the treatment of the RNA with the unmethylated oligomers, either intracellular or in crude extracts that contain RNase H, leads to degradation of the pre-mRNA:antisense oligomer duplexes. Any form of modified antisense oligomers that is capable of by-passing or not inducing such degradation may be used in the present method. The nuclease resistance may be achieved by modifying the antisense oligomers of the invention so that it comprises partially unsaturated aliphatic hydrocarbon chain and one or more polar or charged groups including carboxylic acid groups, ester groups, and alcohol groups.

An example of antisense oligomers which when duplexed with RNA are not cleaved by cellular RNase H is 2'-O-methyl derivatives. Such 2'-O-methyl-oligoribonucleotides are stable in a cellular environment and in animal tissues, and their duplexes with RNA have higher Tm values than their ribo- or deoxyribo-counterparts. Alternatively, the nuclease resistant antisense oligomers of the invention may have at least one of the last 3'-terminus nucleotides fluoridated. Still alternatively, the nuclease resistant antisense oligomers of the invention have phosphorothioate bonds linking between at least two of the last 3-terminus nucleotide bases, preferably having phosphorothioate bonds linking between the last four 3'-terminal nucleotide bases.

Decreased RNA cleavage may also be achieved with alternative oligonucleotide chemistry (see, e.g., U.S. Pat. No. 5,149,797). For example, the antisense oligomer may be chosen from the list comprising: phosphoramidate or phosphorodiamidate morpholino oligomer (PMO); PMO-X; PPMO; peptide nucleic acid (PNA); a locked nucleic acid (LNA) and derivatives including alpha-L-LNA, 2'-amino LNA, 4'-methyl LNA and 4'-O-methyl LNA; ethylene bridged nucleic acids (ENA) and their derivatives; phosphorothioate oligomer; tricyclo-DNA oligomer (tcDNA); tricyclophosphorothioate oligomer; 2'O-Methyl-modified oligomer (2'-OMe); 2'-O-methoxy ethyl (2'-MOE); 2'-fluoro, 2'-fluroarabino (FANA); unlocked nucleic acid (UNA); hexitol nucleic acid (HNA); cyclohexenyl nucleic acid (CeNA); 2'-amino (2'-NH2); 2'-O-ethyleneamine or any combination of the foregoing as mixmers or as gapmers.

To further improve the delivery efficacy, the abovementioned modified nucleotides are often conjugated with fatty acids/lipid/cholesterol/amino acids/carbohydrates/polysaccharides/nanoparticles etc. to the sugar or nucleobase moieties. These conjugated nucleotide derivatives can also be used to construct antisense oligomers to modify cleavage factor binding. Antisense oligomer-induced cleavage factor binding modification of the human NEAT1 gene transcripts have generally used either oligoribonucleotides, PNAs, 2OMe or MOE modified bases on a phosphorothioate backbone. Although 2OMeASOs are used for oligo design, due to their efficient uptake in vitro when delivered as cationic lipoplexes, these compounds are susceptible to nuclease degradation and are not considered ideal for in vivo or clinical applications. When alternative chemistries are used to generate the antisense oligomers of the present invention, the uracil (U) of the sequences provided herein may be replaced by a thymine (T).

For example, such antisense molecules may be oligonucleotides wherein at least one, or all, of the inter-nucleotide bridging phosphate residues are modified phosphates, such as methyl phosphonates, methyl phosphorothioates, phosphoromorpholidates, phosphoropiperazidates and phosphor amidates. For example, every other one of the inter-nucleotide bridging phosphate residues may be modified as described. In another non-limiting example, such antisense molecules are molecules wherein at least one, or all, of the nucleotides contain a 2' lower alkyl moiety (e.g., Ci-C4, linear or branched, saturated or unsaturated alkyl, such as methyl, ethyl, ethenyl, propyl, 1-propenyl, 2-propenyl, and isopropyl). For example, every other one of the nucleotides may be modified as described.

Specific examples of antisense oligonucleotides useful in this invention include oligonucleotides containing modified backbones or non-natural intersubunit linkages.

Oligonucleotides having modified backbones include those that retain a phosphorus atom in the backbone and those that do not have a phosphorus atom in the backbone. Modified oligonucleotides that do not have a phosphorus atom in their inter-nucleoside backbone can also be considered to be oligonucleosides.

In other antisense molecules, both the sugar and the inter-nucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleo-bases are retained and are bound directly or indirectly to aza nitrogen atoms of the amide portion of the backbone.

Modified oligonucleotides may also contain one or more substituted sugar moieties. Oligonucleotides may also include nucleobase (often referred to in the art simply as "base") modifications or substitutions. Oligonucleotides containing a modified or substituted base include oligonucleotides in which one or more purine or pyrimidine bases most commonly found in nucleic acids are replaced with less common or non-natural bases.

Purine bases comprise a pyrimidine ring fused to an imidazole ring; adenine and guanine are the two purine nucleobases most commonly found in nucleic acids. These may be substituted with other naturally-occurring purines, including but not limited to $N_6$-methyladenine, $N_2$-methylguanine, hypoxanthine, and 7-methylguanine.

Pyrimidine bases comprise a six-membered pyrimidine ring; cytosine, uracil, and thymine are the pyrimidine bases most commonly found in nucleic acids. These may be substituted with other naturally-occurring pyrimidines, including but not limited to 5-methylcytosine, 5-hydroxymethylcytosine, pseudouracil, and 4-thiouracil. In one embodiment, the oligonucleotides described herein contain thymine bases in place of uracil.

Other modified or substituted bases include, but are not limited to, 2,6-diaminopurine, orotic acid, agmatidine, lysidine, 2-thiopyrimidine (e.g. 2-thiouracil, 2-thiothymine), G-clamp and its derivatives, 5-substituted pyrimidine (e.g. 5-halouracil, 5-propynyluracil, 5-propynylcytosine, 5-aminomethyluracil, 5-hydroxymethyluracil, 5-aminomethylcytosine, 5-hydroxymethylcytosine, Super T), 7-deazaguanine, 7-deazaadenine, 7-aza-2,6-diaminopurine, 8-aza-7-deazaguanine, 8-aza-7-deazaadenine, 8-aza-7-deaza-2,6-diaminopurine, Super G, Super A, and N4-ethylcytosine, or derivatives thereof; $N_2$-cyclopentylguanine (cPent-G), $N_2$-cyclopentyl-2-aminopurine (cPent-AP), and $N_2$-propyl-2-aminopurine (Pr-AP), pseudouracil or derivatives thereof; and degenerate or universal bases, like 2,6-difluorotoluene or absent bases like abasic sites (e.g. 1-deoxyribose, 1,2-dideoxyribose, 1-deoxy-2-O-methylribose; or pyrrolidine derivatives in which the ring oxygen has been replaced with nitrogen (azaribose)). Examples of derivatives of Super A, Super G and Super T can be found in U.S. Pat. No. 6,683,173 (Epoch Biosciences). cPent-G, cPent-AP and Pr-AP were shown to reduce immunostimulatory effects when incorporated in siRNA (Peacock H. et al. J. Am. Chem. Soc. 2011, 133, 9200). Pseudouracil is a naturally occurring isomerized version of uracil, with a C-glycoside rather than the regular N-glycoside as in uridine. Pseudouridine-containing synthetic mRNA may have an improved safety profile compared to uridine-containing mPvNA (see WO 2009127230).

Certain modified or substituted nucleo-bases are particularly useful for increasing the binding affinity of the antisense oligonucleotides of the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. and are presently preferred base substitutions, even more particularly when combined with 2'-O-methoxyethyl sugar modifications.

In some embodiments, modified or substituted nucleobases are useful for facilitating purification of antisense oligonucleotides. For example, in certain embodiments, antisense oligonucleotides may contain three or more (e.g., 3, 4, 5, 6 or more) consecutive guanine bases. In certain antisense oligonucleotides, a string of three or more consecutive guanine bases can result in aggregation of the oligonucleotides, complicating purification. In such antisense oligonucleotides, one or more of the consecutive guanines can be substituted with inosine. The substitution of inosine for one or more guanines in a string of three or more consecutive guanine bases can reduce aggregation of the antisense oligonucleotide, thereby facilitating purification.

In one embodiment, another modification of the antisense oligonucleotides involves chemically linking to the oligonucleotide one or more moieties or conjugates that enhance the activity, cellular distribution or cellular uptake of the oligonucleotide. Such moieties include but are not limited to lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety.

It is not necessary for all positions in a given compound to be uniformly modified, and in fact more than one of the aforementioned modifications may be incorporated in a single compound or even at a single nucleoside within an oligonucleotide. The present invention also includes antisense oligonucleotides that are chimeric compounds. "Chimeric" antisense compounds or "chimeras," in the context of this invention, are antisense molecules, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the increased resistance to nuclease degradation, increased cellular uptake, and an additional region for increased binding affinity for the target nucleic acid.

The antisense molecules used in accordance with this invention may be conveniently and routinely made through the well-known technique of solid phase synthesis. Equipment for such synthesis is sold by several vendors including, for example, Applied Biosystems (Foster City, Calif.). One method for synthesising oligonucleotides on a modified solid support is described in U.S. Pat. No. 4,458,066.

In another non-limiting example, such antisense oligomers are molecules wherein at least one, or all, of the nucleotides contain a 2' lower alkyl moiety (such as, for example, $C_1$-$C_4$, linear or branched, saturated or unsaturated alkyl, such as methyl, ethyl, ethenyl, propyl, 1-propenyl, 2-propenyl, and isopropyl). For example, every other one of the nucleotides may be modified as described.

While the antisense oligomers described above are a preferred form of the antisense oligomers of the present invention, the present invention includes other oligomeric antisense molecules, including but not limited to oligomer mimetics such as are described below.

Another preferred chemistry is the phosphorodiamidate morpholino oligomer (PMO) oligomeric compounds, which are not degraded by any known nuclease or protease. These compounds are uncharged, do not activate RNase H activity when bound to a RNA strand and have been shown to exert sustained cleavage factor binding modulation after in vivo administration (Summerton and Weller, Antisense Nucleic Acid Drug Development, 7, 187-197).

Modified oligomers may also contain one or more substituted sugar moieties. Oligomers may also include nucleobase (often referred to in the art simply as "base") modifications or substitutions. Certain nucleobases are particularly useful for increasing the binding affinity of the oligomeric compounds of the invention. These include 5-substituted pyrimidines, 6-azapyrimidines, and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C., even more particularly when combined with 2'-O-methoxyethyl sugar modifications. In one embodiment, at least one pyrimidine base of the oligonucleotide comprises a 5-substituted pyrimidine base, wherein the pyrimidine base is selected from the group consisting of cytosine, thymine and uracil. In one embodiment, the 5-substituted pyrimidine base is 5-methylcytosine. In another embodiment, at least one purine base of the oligonucleotide comprises an N-2, N-6 substituted purine base. In one embodiment, the N-2, N-6 substituted purine base is 2, 6-diaminopurine.

In one embodiment, the antisense oligonucleotide includes one or more 5-methylcytosine substitutions alone or in combination with another modification, such as 2'-O-methoxyethyl sugar modifications. In yet another embodiment, the antisense oligonucleotide includes one or more 2, 6-diaminopurine substitutions alone or in combination with another modification.

In some embodiments, the antisense oligonucleotide is chemically linked to one or more moieties, such as a polyethylene glycol moiety, or conjugates, such as a arginine-rich cell penetrating peptide that enhance the activity, cellular distribution, or cellular uptake of the antisense oligonucleotide. In one exemplary embodiment, the arginine-rich polypeptide is covalently coupled at its N-terminal or C-terminal residue to the 3' or 5' end of the antisense compound. Also in an exemplary embodiment, the antisense compound is composed of morpholino subunits and phosphorus-containing inter-subunit linkages joining a morpholino nitrogen of one subunit to a 5' exocyclic carbon of an adjacent subunit.

In another aspect, the invention provides expression vectors that incorporate the antisense oligonucleotides described above, e.g., the antisense oligonucleotides of SEQ ID NOs: 1-54. In some embodiments, the expression vector is a modified retrovirus or non-retroviral vector, such as a adeno-associated viral vector.

Another modification of the oligomers of the invention involves chemically linking to the oligomer one or more moieties or conjugates that enhance the activity, cellular distribution or cellular uptake of the oligomer. Such moieties include but are not limited to lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, myristyl, or an octadecylamine or hexylamino-carbonyl-oxycholesterol moiety.

Cell penetrating peptides have been added to phosphorodiamidate morpholino oligomers to enhance cellular uptake and nuclear localization. Different peptide tags have been shown to influence efficiency of uptake and target tissue specificity, as shown in Jearawiriyapaisarn et al. (2008), Mol. Ther. 16 9, 1624-1629. The terms "cell penetrating peptide" and "CPP" are used interchangeably and refer to cationic cell penetrating peptides, also called transport peptides, carrier peptides, or peptide transduction domains. The peptides, as shown herein, have the capability of inducing cell penetration within 100% of cells of a given cell culture population and allow macromolecular translocation within multiple tissues in vivo upon systemic administration.

It is not necessary for all positions in a given compound to be uniformly modified, and in fact more than one of the aforementioned modifications may be incorporated in a single compound or even at a single nucleoside within an oligomer. The present invention also includes antisense oligomers that are chimeric compounds. "Chimeric" antisense oligomers or "chimeras," in the context of this invention, are antisense oligomers, particularly oligomers, which contain two or more chemically distinct regions, each made up of at least one monomer unit, i.e., a nucleotide in the case of an oligomer compound. These oligomers typically contain at least one region wherein the oligomer is modified so as to confer upon the oligomer or antisense oligomer increased resistance to nuclease degradation, increased cellular uptake, and an additional region for increased binding affinity for the target nucleic acid.

The activity of antisense oligomers and variants thereof can be assayed according to routine techniques in the art. For example, isoform forms and expression levels of surveyed RNAs and proteins may be assessed by any of a wide variety of well-known methods for detecting isoforms and/or expression of a transcribed nucleic acid or protein. Non-limiting examples of such methods include RT-PCR of isoforms of RNA followed by size separation of PCR products, nucleic acid hybridization methods e.g., Northern blots and/or use of nucleic acid arrays; fluorescent in situ hybridization to detect RNA transcripts inside cells; nucleic acid amplification methods; immunological methods for detection of proteins; protein purification methods; and protein function or activity assays.

RNA expression levels can be assessed by preparing RNA/cDNA (i.e., a transcribed polynucleotide) from a cell, tissue or organism, and by hybridizing the RNA/cDNA with a reference polynucleotide, which is a complement of the assayed nucleic acid, or a fragment thereof. cDNA can, optionally, be amplified using any of a variety of polymerase chain reaction or in vitro transcription methods prior to hybridization with the complementary polynucleotide; preferably, it is not amplified. Expression of one or more transcripts can also be detected using quantitative PCR to assess the level of expression of the transcripT1 (s).

The present invention provides antisense oligomer modified cleavage factor binding of the NEAT1 gene transcript, clinically relevant oligomer chemistries and delivery systems to direct NEAT1 cleavage manipulation to therapeutic levels. Substantial increases in the amount of NEAT1_2 RNA are achieved by:
1) oligomer refinement in vitro using cell lines, through experimental assessment of (i) modification of cleavage factor binding target motifs, (ii) antisense oligomer length and development of oligomer cocktails, (iii) choice of chemistry, and (iv) the addition of cell-penetrating peptides (CPP) to enhance oligomer delivery; and
2) detailed evaluation of a novel approach to increase NEAT1_2 transcripts.

As such, it is demonstrated herein that processing of NEAT1 RNA can be manipulated with specific antisense oligomers. In this way functionally significant increases in the amount of the NEAT1_2 isoform can be obtained, thereby reducing the pathology of a disease associated with over-expression of NEAT1_1 and/or under-expression of NEAT1_2.

Preferably, the disease associated with over-expression of NEAT1_1 and/or under-expression of NEAT1_2 is:
a cancer associated with over-expression of NEAT1_1, which is indicated by the expression of NEAT11 promoting the survival of cancer cells;
a cancer associated with the under-expression of NEAT1_2, which is indicated by the over-expression of NEAT1_1, or alternatively by observations that when NEAT1_2 expression is increased, the cancer's growth is reduced or inhibited;
a cancer associated with paraspeckle insufficiency or low numbers of paraspeckles;
a cancer associated with over-expression of NEAT1_1 and/or under-expression of NEAT1_2 chosen from the list comprising: neuroblastoma, lung cancer including non-small cell lung cancer, oesophageal squamous cell carcinoma, laryngeal squamous cell carcinoma, colorectal cancer, breast cancer, prostate cancer, endometrial endometrioid adenocarcinoma, gastric cancer, glioma, thyroid carcinoma, bladder cancer, osteosarcoma, ovarian cancer;
a cancer chosen from the list comprising: neuroblastoma, lung cancer including non-small cell lung cancer, colorectal cancer, breast cancer, bladder cancer, osteosarcoma, liver cancer, ovarian cancer;
a cancer dependent on high activity of the cholesterol synthesis pathway; and/or
a cancer associated with over-expression of NEAT1_1 and/or under-expression of NEAT1_2 that is also dependent on high activity of the cholesterol synthesis pathway chosen from the list comprising: neuroblastoma, osteosarcoma, or colorectal or non-small cell lung cancer.

The antisense oligomers used in accordance with this invention may be conveniently made through the well-known technique of solid phase synthesis. Equipment for such synthesis is sold by several vendors including, for example, Applied Biosystems (Foster City, Calif.). One method for synthesising oligomers on a modified solid support is described in U.S. Pat. No. 4,458,066.

Any other means for such synthesis known in the art may additionally or alternatively be employed. It is well known to use similar techniques to prepare oligomers such as the phosphorothioates and alkylated derivatives. In one such automated embodiment, diethyl-phosphoramidites are used as starting materials and may be synthesized as described by Beaucage, et al., (1981) Tetrahedron Letters, 22:1859-1862.

The antisense oligomers of the invention are synthesised in vitro and do not include antisense compositions of biological origin, or genetic vector constructs designed to direct the in vivo synthesis of antisense oligomers. The molecules of the invention may also be mixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption.

Also included are vector delivery systems that are capable of expressing the oligomeric, NEAT1-targeting sequences of the present invention, such as vectors that express a polynucleotide sequence comprising any one or more of SEQ ID NOs: 1-55, as described herein. By "vector" or "nucleic acid construct" is meant a polynucleotide molecule, preferably a DNA molecule derived, for example, from a plasmid, bacteriophage, yeast or virus, into which a polynucleotide can be inserted or cloned. A vector preferably contains one or more unique restriction sites and can be capable of autonomous replication in a defined host cell including a target cell or tissue or a progenitor cell or tissue thereof, or be integrable with the genome of the defined host such that the cloned sequence is reproducible. Accordingly, the vector can be an autonomously replicating vector, i.e., a vector that exists as an extra-chromosomal entity, the replication of which is independent of chromosomal replication, e.g., a linear or closed circular plasmid, an extra-chromosomal element, a mini-chromosome, or an artificial chromosome. The vector can contain any means for assuring self-replication. Alternatively, the vector can be one which, when introduced into the host cell, is integrated into the genome and replicated together with the chromosome(s) into which it has been integrated.

Method of Treatment

The antisense oligomers of the present invention also can be used as a prophylactic or therapeutic, which may be utilised for the purpose of treatment of a disease. Accordingly, in one embodiment the present invention provides antisense oligomers that bind to a selected target in the NEAT1 RNA to modify cleavage of the RNA as described herein, in a therapeutically effective amount, admixed with a pharmaceutically acceptable carrier, diluent, or excipient.

An "effective amount" or "therapeutically effective amount" refers to an amount of therapeutic compound, such as an antisense oligomer, administered to a mammalian subject, either as a single dose or as part of a series of doses, which is effective to produce a desired therapeutic effect.

The invention therefore provides a pharmaceutical, prophylactic, or therapeutic composition to treat, prevent or ameliorate the effects of a disease associated with over-expression of NEAT1_1 and/or under-expression of NEAT1_2 in a subject, the composition comprising:
 a) one or more antisense oligomers as described herein, and
 b) one or more pharmaceutically acceptable carriers and/or diluents.

Preferably, the disease associated with over-expression of NEAT1_1 and/or under-expression of NEAT1_2 is:
 a cancer associated with over-expression of NEAT1_1, which is indicated by the expression of NEAT11 promoting the survival of cancer cells;
 a cancer associated with the under-expression of NEAT1_2, which is indicated by the over-expression of NEAT1_1, or alternatively by observations that when NEAT1_2 expression is increased, the cancer's growth is reduced or inhibited;
 a cancer associated with paraspeckle insufficiency or low numbers of paraspeckles;
 a cancer associated with over-expression of NEAT1_1 and/or under-expression of NEAT1_2 chosen from the list comprising: neuroblastoma, lung cancer including non-small cell lung cancer, oesophageal squamous cell carcinoma, laryngeal squamous cell carcinoma, colorectal cancer, breast cancer, prostate cancer, endometrial endometrioid adenocarcinoma, gastric cancer, glioma, thyroid carcinoma, bladder cancer, osteosarcoma, ovarian cancer;
 a cancer chosen from the list comprising: neuroblastoma, lung cancer including non-small cell lung cancer, breast cancer, bladder cancer, colorectal cancer, osteosarcoma, liver cancer, ovarian cancer;
 a cancer dependent on high activity of the cholesterol synthesis pathway; and/or
 a cancer associated with over-expression of NEAT1_1 and/or under-expression of NEAT1_2 that is also dependent on high activity of the cholesterol synthesis pathway chosen from the list comprising: neuroblastoma, osteosarcoma, or colorectal or non-small cell lung cancer.

Preferably, the ASO used in the present invention is chosen from the list comprising:
 Table 1;
 SEQ ID NO: 13 to 42 and 55;
 SEQ ID NO: 13, 22, 24, 26, 28, 30, 32, 34, 36, 38, 40, 42 or 55; or
 SEQ ID NO: 22, 32 or 55.

The composition may comprise about 1 nM to 1000 nM of each of the desired antisense oligomer(s) of the invention. Preferably, the composition may comprise about 1 nM to 500 nM, 10 nM to 500 nM, 50 nM to 750 nM, 10 nM to 500 nM, 1 nM to 100 nM, 1 nM to 50 nM, 1 nM to 40 nM, 1 nM to 30 nM, 1 nM to 20 nM, most preferably between 1 nM and 10 nM of each of the antisense oligomer(s) of the invention.

The composition may comprise about 1 nm, 2 nm, 3 nm, 4 nm, 5 nm, 6 nm, 7 nm, 8 nm, 9 nm, 10 nm, 20 nm, 50 nm, 75 nm, 100 nm, 150 nm, 200 nm, 250 nm, 300 nm, 350 nm, 400 nm, 450 nm, 500 nm, 550 nm, 600 nm, 650 nm, 700 nm, 750 nm, 800 nm, 850 nm, 900 nm, 950 nm or 1000 nm of each of the desired antisense oligomer(s) of the invention.

The present invention further provides one or more antisense oligomers adapted to aid in the prophylactic or therapeutic treatment, prevention or amelioration of symptoms of a disease or pathology associated with over-expression of NEAT1_1 and/or under-expression of NEAT1_2 in a form suitable for delivery to a subject.

The phrase "pharmaceutically acceptable" refers to molecular entities and compositions that are physiologically tolerable and do not typically produce an allergic or similarly untoward reaction, such as gastric upset and the like, when administered to a subject. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or saline solutions and aqueous dextrose and glycerol solutions are preferably employed as carriers, particularly for injectable solutions. Suitable pharmaceutical carriers are described in Martin, *Remington's Pharmaceutical Sciences*, 18th Ed., Mack Publishing Co., Easton, Pa., (1990).

Pharmaceutical Compositions

In a form of the invention there are provided pharmaceutical compositions comprising therapeutically effective amounts of one or more antisense oligomers of the invention together with pharmaceutically acceptable diluents, preservatives, solubilizers, emulsifiers, adjuvants, and/or carriers. Such compositions include diluents of various buffer content (e.g. Tris-HCl, acetate, phosphate), pH and ionic strength and additives such as detergents and solubilizing agents (e.g. Tween 80, Polysorbate 80), anti-oxidants (e.g., ascorbic acid, sodium metabisulfite), preservatives (e.g. Thimersol, benzyl alcohol) and bulking substances (e.g., lactose, mannitol). The material may be incorporated into particulate preparations of polymeric compounds such as polylactic acid, polyglycolic acid, etc. or into liposomes. Hylauronic acid may also be used. Such compositions may influence the physical state, stability, rate of in vivo release, and rate of in vivo clearance of the present proteins and derivatives. See, for example, Martin, Remington's Pharmaceutical Sciences, 18th Ed. (1990, Mack Publishing Co., Easton, Pa. 18042) pages 1435-1712 that are herein incorporated by reference. The compositions may be prepared in liquid form, or may be in dried powder, such as a lyophilised form.

It will be appreciated that pharmaceutical compositions provided according to the present invention may be administered by any means known in the art. Preferably, the pharmaceutical compositions for administration are administered by injection, orally, topically or by the pulmonary or nasal route. The antisense oligomers are more preferably delivered by intravenous, intra-arterial, intraperitoneal, intramuscular or subcutaneous routes of administration. The appropriate route may be determined by one of skill in the art, as appropriate to the condition of the subject under treatment. Vascular or extravascular circulation, the blood or lymph system, and the cerebrospinal fluid are some non-limiting sites where the antisense oligomer may be introduced. Direct CNS delivery may be employed, for instance, intracerebral ventribular or intrathecal administration may be used as routes of administration.

Formulations for topical administration include those in which the oligomers of the disclosure are in admixture with a topical delivery agent such as lipids, liposomes, fatty acids, fatty acid esters, steroids, chelating agents and surfactants.

Lipids and liposomes include neutral (e.g. dioeoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA). For topical or other administration, oligomers of the disclosure may be encapsulated within liposomes or may form complexes thereto, in particular to cationic liposomes. Alternatively, oligomers may be complexed to lipids, in particular to cationic lipids. Fatty acids and esters, pharmaceutically acceptable salts thereof, and their uses are further described in U.S. Pat. No. 6,287,860 and/or U.S. patent application Ser. No. 09/315,298 filed on May 20, 1999.

In certain embodiments, the antisense oligomers of the disclosure can be delivered by transdermal methods (e.g., via incorporation of the antisense oligomers into, e.g., emulsions, with such antisense oligomers optionally packaged into liposomes). Such transdermal and emulsion/liposome-mediated methods of delivery are described for delivery of antisense oligomers in the art, e.g., in U.S. Pat. No. 6,965,025.

The antisense oligomers described herein may also be delivered via an implantable device. Design of such a device is an art-recognized process, with, e.g., synthetic implant design described in, e.g., U.S. Pat. No. 6,969,400.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Oral formulations are those in which oligomers of the disclosure are administered in conjunction with one or more penetration enhancers surfactants and chelators. Surfactants include fatty acids and/or esters or salts thereof, bile acids and/or salts thereof. Bile acids/salts and fatty acids and their uses are further described in U.S. Pat. No. 6,287,860. In some embodiments, the present disclosure provides combinations of penetration enhancers, for example, fatty acids/salts in combination with bile acids/salts. An exemplary combination is the sodium salt of lauric acid, capric acid and UDCA. Further penetration enhancers include polyoxyethylene-9-lauryl ether, polyoxyethylene-20-cetyl ether. Oligomers of the disclosure may be delivered orally, in granular form including sprayed dried particles, or complexed to form micro or nanoparticles. Oligomer complexing agents and their uses are further described in U.S. Pat. No. 6,287,860. Oral formulations for oligomers and their preparation are described in detail in U.S. Pat. No. 6,887,906, Ser. No. 09/315,298 filed May 20, 1999 and/or US20030027780.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

The delivery of a therapeutically useful amount of antisense oligomers may be achieved by methods previously published. For example, intracellular delivery of the antisense oligomer may be via a composition comprising an admixture of the antisense oligomer and an effective amount of a block copolymer. An example of this method is described in US patent application US20040248833. Other methods of delivery of antisense oligomers to the nucleus are described in Mann C J et al. (2001) Proc, Natl. Acad. Science, 98(1) 42-47, and in Gebski et al. (2003) Human Molecular Genetics, 12(15): 1801-1811. A method for introducing a nucleic acid molecule into a cell by way of an expression vector either as naked DNA or complexed to lipid carriers, is described in U.S. Pat. No. 6,806,084.

In certain embodiments, the antisense oligomers of the invention and therapeutic compositions comprising the same can be delivered by transdermal methods (e.g., via incorporation of the antisense oligomers into, e.g., emulsions, with such antisense oligomers optionally packaged into liposomes). Such transdermal and emulsion/liposome-mediated methods of delivery are described for delivery of antisense oligomers in the art, e.g., in U.S. Pat. No. 6,965,025.

It may be desirable to deliver the antisense oligomer in a colloidal dispersion system. Colloidal dispersion systems include macromolecule complexes, nanocapsules, microspheres, beads, and lipid-based systems including oil-in-water emulsions, micelles, mixed micelles, and liposomes or liposome formulations. These colloidal dispersion systems can be used in the manufacture of therapeutic pharmaceutical compositions.

Liposomes are artificial membrane vesicles, which are useful as delivery vehicles in vitro and in vivo. These formulations may have net cationic, anionic, or neutral charge characteristics and have useful characteristics for in vitro, in vivo and ex vivo delivery methods. It has been shown that large unilamellar vesicles can encapsulate a substantial percentage of an aqueous buffer containing large macromolecules. RNA and DNA can be encapsulated within the aqueous interior and be delivered to cells in a biologically active form (Fraley, et al., Trends Biochem. Sci. 6:77, 1981).

In order for a liposome to be an efficient gene transfer vehicle, the following characteristics should be present: (1) encapsulation of the antisense oligomer of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., Biotechniques, 6:682, 1988). The composition of the liposome is usually a combination of phospholipids, particularly high phase-transition-temperature phospholipids, usually in combination with steroids, especially cholesterol. Other phospholipids or other lipids may also be used. The physical characteristics of liposomes depend on pH, ionic strength, and the presence of divalent cations. Cationic liposomes are positively charged liposomes which are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860.

The antisense oligomers described herein may also be delivered via an implantable device. Design of such a device is an art-recognized process, with, e.g., synthetic implant design described in, e.g., U.S. Pat. No. 6,969,400, the contents of which are incorporated in their entirety by reference herein.

Antisense oligomers can be introduced into cells using art-recognized techniques (e.g., transfection, electroporation, fusion, liposomes, colloidal polymeric particles and viral and non-viral vectors as well as other means known in the art). The method of delivery selected will depend at least on the cells to be treated and the location of the cells and will be apparent to the skilled artisan. For instance, localization can be achieved by liposomes with specific markers on the surface to direct the liposome, direct injection into tissue containing target cells, specific receptor-mediated uptake, or the like.

As known in the art, antisense oligomers may be delivered using, for example, methods involving liposome-mediated uptake, lipid conjugates, polylysine-mediated uptake, nanoparticle-mediated uptake, and receptor-mediated endocytosis, as well as additional non-endocytic modes of delivery, such as microinjection, permeabilization (e.g., streptolysin-O permeabilization, anionic peptide permeabilization), electroporation, and various non-invasive non-endocytic methods of delivery that are known in the art (refer to Dokka and Rojanasakul, Advanced Drug Delivery Reviews 44, 35-49, incorporated by reference in its entirety).

The antisense oligomer may also be combined with other pharmaceutically acceptable carriers or diluents to produce a pharmaceutical composition. Suitable carriers and diluents include isotonic saline solutions, for example phosphate-buffered saline. The composition may be formulated for parenteral, intramuscular, intravenous, subcutaneous, intraocular, oral, or transdermal administration.

The routes of administration described are intended only as a guide since a skilled practitioner will be able to readily determine the optimum route of administration and any dosage for any particular animal and condition.

Multiple approaches for introducing functional new genetic material into cells, both in vitro and in vivo have been attempted (Friedmann (1989) Science, 244:1275-1280). These approaches include integration of the gene to be expressed into modified retroviruses (Friedmann (1989) supra; Rosenberg (1991) Cancer Research 51(18), suppl.: 5074S-5079S); integration into non-retrovirus vectors (Rosenfeld, et al. (1992) Cell, 68:143-155; Rosenfeld, et al. (1991) Science, 252:431-434); or delivery of a transgene linked to a heterologous promoter-enhancer element via liposomes (Friedmann (1989), supra; Brigham, et al. (1989) Am. J. Med. Sci., 298:278-281; Nabel, et al. (1990) Science, 249:1285-1288; Hazinski, et al. (1991) Am. J. Resp. Cell Molec. Biol., 4:206-209; and Wang and Huang (1987) Proc. Natl. Acad. Sci. (USA), 84:7851-7855); coupled to ligand-specific, cation-based transport systems (Wu and Wu (1988) J. Biol. Chem., 263:14621-14624) or the use of naked DNA expression vectors (Nabel et al. (1990), supra); Wolff et al. (1990) Science, 247:1465-1468). Direct injection of transgenes into tissue produces only localized expression (Rosenfeld (1992) supra); Rosenfeld et al. (1991) supra; Brigham et al. (1989) supra; Nabel (1990) supra; and Hazinski et al. (1991) supra). The Brigham et al. group (Am. J. Med. Sci. (1989) 298:278-281 and Clinical Research (1991) 39 (abstract)) have reported in vivo transfection only of lungs of mice following either intravenous or intratracheal administration of a DNA liposome complex. An example of a review article of human gene therapy procedures is: Anderson, Science (1992) 256:808-813; Barteau et al. (2008), Curr Gene Ther; 8(5):313-23; Mueller et al. (2008). Clin Rev Allergy Immunol; 35(3):164-78; Li et al. (2006) Gene Ther., 13(18):1313-9; Simoes et al. (2005) Expert Opin Drug Deliv; 2(2):237-54.

The antisense oligomers of the invention encompass any pharmaceutically acceptable salts, esters, or salts of such esters, or any other compound which, upon administration to an animal including a human, is capable of providing (directly or indirectly) the biologically active metabolite or residue thereof. Accordingly, as an example, the disclosure is also drawn to prodrugs and pharmaceutically acceptable salts of the compounds of the invention, pharmaceutically acceptable salts of such pro-drugs, and other bioequivalents.

The term "pharmaceutically acceptable salts" refers to physiologically and pharmaceutically acceptable salts of the compounds of the invention: i.e. salts that retain the desired biological activity of the parent compound and do not impart undesired toxicological effects thereto. For oligomers, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine. The pharmaceutical compositions of the present invention may be administered in a number of ways depending upon whether local or systemic treatment is desired and upon the area to be treated. Administration may be topical (including ophthalmic and mucous membranes, as well as rectal delivery), pulmonary, e.g., by inhalation or insufflation of powders or aerosols (including by nebulizer, intratracheal, intranasal, epidermal and transdermal), oral or parenteral. Parenteral administration includes intravenous, intra-arterial, subcutaneous, intraperitoneal or intramuscular injection or infusion; or intracranial, e.g., intrathecal or intraventricular, administration. Oligomers with at least one 2'-O-methoxyethyl modification are believed to be particularly useful for oral administration. Preferably, the antisense oligomer is delivered via the subcutaneous or intravenous route.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipienT1(s). In general the formulations are prepared by uniformly and intimately bringing into association the active ingredients with liquid carriers or finely divided solid carriers or both, and then, if necessary, shaping the product.

Administration

In one embodiment, the antisense oligomer is administered in an amount and manner effective to result in a peak blood concentration of at least 200-400 nM antisense oligomer. Typically, one or more doses of antisense oligomer are administered, generally at regular intervals, for a period of about one to two weeks. Preferred doses for oral administration are from about 1 mg to 1000 mg oligomer per 70 kg. In some cases, doses of greater than 1000 mg oligomer/ subject may be necessary. For intra venous administration, preferred doses are from about 0.5 mg to 1000 mg oligomer per 70 kg. For intra venous or sub cutaneous administration, the antisense oligomer may be administered at a dosage of about 120 mg/kg daily or weekly.

The antisense oligomer may be administered at regular intervals for a short time period, e.g., daily for two weeks or less. However, in some cases the oligomer is administered intermittently over a longer period of time. Administration may be followed by, or concurrent with, administration of an antibiotic or other therapeutic treatment. The treatment regimen may be adjusted (dose, frequency, route, etc.) as indicated, based on the results of immunoassays, other biochemical tests and physiological examination of the subject under treatment.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the subject. Persons of ordinary skill can easily determine optimum dosages, dosing methodologies and repetition rates. Optimum dosages may vary depending on the relative potency of individual oligomers, and can generally be estimated based on EC50s found to be effective in in vitro and in vivo animal models. In general, dosage is from 0.01 µg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the subject undergo maintenance therapy to prevent the recurrence of the disease state, wherein the oligomer is administered in maintenance doses, ranging from 0.01 µg to 100 g per kg of body weight, once or more daily, to once every 20 years.

An effective in vivo treatment regimen using the antisense oligomers of the invention may vary according to the duration, dose, frequency and route of administration, as well as the condition of the subject under treatment (i.e., prophylactic administration versus administration in response to localized or systemic infection). Accordingly, such in vivo therapy will often require monitoring by tests appropriate to the particular type of disorder under treatment, and corresponding adjustments in the dose or treatment regimen, in order to achieve an optimal therapeutic outcome.

Treatment may be monitored, e.g., by general indicators of disease known in the art. As used herein, "treatment" of a subject (e.g. a mammal, such as a human) or a cell is any type of intervention used in an attempt to alter the natural course of the individual or cell. Treatment includes, but is not limited to, administration of a pharmaceutical composition, and may be performed either prophylactically or subsequent to the initiation of a pathologic event or contact with an etiologic agent. Treatment includes any desirable effect on the symptoms or pathology of a disease or condition associated with NEAT1, and may include, for example, minimal changes or improvements in one or more measurable markers of the disease or condition being treated. Also included are "prophylactic" treatments, which can be directed to reducing the rate of progression of the disease or condition being treated, delaying the onset of that disease or condition, or reducing the severity of its onset. "Treatment" or "prophylaxis" does not necessarily indicate complete eradication, cure, or prevention of the disease or condition, or associated symptoms thereof.

A "subject," as used herein, includes any animal that exhibits a symptom, or is at risk for exhibiting a symptom, which can be treated with an antisense compound of the invention, or any of the symptoms associated with these conditions (e.g., overproduction of cholesterol). Suitable subjects include laboratory animals (such as mouse, rat, rabbit, or guinea pig), farm animals, and domestic animals or pets (such as a cat or dog). Non-human primates and, preferably, human subjects, are included.

The efficacy of an in vivo administered antisense oligomers of the invention may be determined from biological samples (tissue, blood, urine etc.) taken from a subject prior to, during and subsequent to administration of the antisense oligomer. Assays of such samples include (1) monitoring the presence or absence of heteroduplex formation with target and non-target sequences, using procedures known to those skilled in the art, e.g., an electrophoretic gel mobility assay; (2) monitoring the amount of a mutant RNA in relation to a reference normal RNA or protein as determined by standard techniques such as RT-PCR, Northern blotting, ELISA or Western blotting.

Intranuclear oligomer delivery is a major challenge for antisense oligomers. Different cell-penetrating peptides (CPP) localize PMOs to varying degrees in different conditions and cell lines, and novel CPPs have been evaluated by the inventors for their ability to deliver PMOs to the target cells. The terms CPP or "a peptide moiety which enhances cellular uptake" are used interchangeably and refer to cationic cell penetrating peptides, also called "transport peptides", "carrier peptides", or "peptide transduction domains". The peptides, as shown herein, have the capability of inducing cell penetration within about or at least about 30%, 40%, 50%, 60%, 70%, 80%, 90%, or 100% of cells of a given cell culture population and allow macromolecular translocation within multiple tissues in vivo upon systemic administration. CPPs are well-known in the art and are disclosed, for example in U.S. Application No. 2010/0016215, which is incorporated by reference in its entirety.

The present invention therefore provides antisense oligomers of the present invention in combination with cell-penetrating peptides for manufacturing therapeutic pharmaceutical compositions.

According to a still further aspect of the invention, there is provided one or more antisense oligomers as described herein for use in an antisense oligomer-based therapy. Preferably, the therapy is for a disease associated with over-expression of NEAT1_1 and/or under-expression of NEAT1_2.

Preferably, the disease associated with over-expression of NEAT1_1 and/or under-expression of NEAT1_2 is:
- a cancer associated with over-expression of NEAT1_1, which is indicated by the expression of NEAT11 promoting the survival of cancer cells;
- a cancer associated with the under-expression of NEAT1_2, which is indicated by the over-expression of NEAT1_1, or alternatively by observations that when NEAT1_2 expression is increased, the cancer's growth is reduced or inhibited;
- a cancer associated with paraspeckle insufficiency or low numbers of paraspeckles;
- a cancer associated with over-expression of NEAT1_1 and/or under-expression of NEAT1_2 chosen from the list comprising: neuroblastoma, lung cancer including non-small cell lung cancer, oesophageal squamous cell carcinoma, laryngeal squamous cell carcinoma, colorectal cancer, breast cancer, prostate cancer, endometrial endometrioid adenocarcinoma, gastric cancer, glioma, thyroid carcinoma, bladder cancer, osteosarcoma, ovarian cancer;

a cancer chosen from the list comprising: neuroblastoma, lung cancer including non-small cell lung cancer, breast cancer, bladder cancer, colorectal cancer, osteosarcoma, liver cancer, ovarian cancer;

a cancer dependent on high activity of the cholesterol synthesis pathway; and/or a cancer associated with over-expression of NEAT1_1 and/or under-expression of NEAT1_2 that is also dependent on high activity of the cholesterol synthesis pathway chosen from the list comprising: neuroblastoma, osteosarcoma, or colorectal or non-small cell lung cancer.

More specifically, the antisense oligomer may be selected from the group consisting of any one or more of SEQ ID NOs: 1-55, and combinations or cocktails thereof. This includes sequences which can hybridise to such sequences under stringent hybridisation conditions, sequences complementary thereto, sequences containing modified bases, modified backbones, and functional truncations or extensions thereof which possess or modulate pre-RNA processing activity in a NEAT1 gene transcript. More preferably, the ASO used in the present invention is chosen from the list comprising: SEQ ID NO: 22 or 32 to 55; more preferably, the ASO used in the present invention is SEQ ID NO: 22, 32 or 55.

The invention extends also to a combination of two or more antisense oligomers capable of binding to a selected target to modify cleavage of a NEAT1 gene transcript. The combination may be a cocktail of two or more antisense oligomers, a construct comprising two or more or two or more antisense oligomers joined together for use in an antisense oligomer-based therapy.

The invention provides a method to treat, prevent or ameliorate the effects of a disease associated with over-expression of NEAT1_1 and/or under-expression of NEAT1_2, comprising the step of:

a) administering to the subject an effective amount of one or more antisense oligomers or pharmaceutical composition comprising one or more antisense oligomers as described herein.

Furthermore, the invention provides a method to treat, prevent or ameliorate a disease associated with over-expression of NEAT1_1 and/or under-expression of NEAT1_2, comprising the step of:

a) administering to the subject an effective amount of one or more antisense oligomers or pharmaceutical composition comprising one or more antisense oligomers as described herein wherein the disease associated with over-expression of NEAT1_1 and/or under-expression of NEAT1_2 is:

a cancer associated with over-expression of NEAT1_1, which is indicated by the expression of NEAT11 promoting the survival of cancer cells;

a cancer associated with the under-expression of NEAT1_2, which is indicated by the over-expression of NEAT1_1, or alternatively by observations that when NEAT1_2 expression is increased, the cancer's growth is reduced or inhibited;

a cancer associated with paraspeckle insufficiency or low numbers of paraspeckles;

a cancer associated with over-expression of NEAT1_1 and/or under-expression of NEAT1_2 chosen from the list comprising: neuroblastoma, lung cancer including non-small cell lung cancer, oesophageal squamous cell carcinoma, laryngeal squamous cell carcinoma, colorectal cancer, breast cancer, prostate cancer, endometrial endometrioid adenocarcinoma, gastric cancer, glioma, thyroid carcinoma, bladder cancer, osteosarcoma, ovarian cancer;

a cancer chosen from the list comprising: neuroblastoma, lung cancer including non-small cell lung cancer, breast cancer, bladder cancer, colorectal cancer, osteosarcoma, liver cancer, ovarian cancer;

a cancer dependent on high activity of the cholesterol synthesis pathway; and/or a cancer associated with over-expression of NEAT1_1 and/or under-expression of NEAT1_2 that is also dependent on high activity of the cholesterol synthesis pathway chosen from the list comprising: neuroblastoma, osteosarcoma, or colorectal or non-small cell lung cancer.

Preferably, the therapy is used to change the ratio of NEAT1_1:NEAT1_2, preferably to up-regulate the NEAT1_2 RNA isoform of NEAT1 RNA. The increase in levels of NEAT12 is preferably achieved by increasing the full length transcript level through modifying pre-mRNA cleavage factor binding in the NEAT1 gene transcript or part thereof.

The reduction in short isoform NEAT1_1 will preferably lead to a reduction in the quantity, duration or severity of the symptoms of a disease associated with over-expression of NEAT1_1 and/or under-expression of NEAT12, such as various solid cancers.

According to another aspect of the invention there is provided the use of one or more antisense oligomers as described herein in the manufacture of a medicament for the modulation or control of a disease associated with over-expression of NEAT1_1 and/or under-expression of NEAT1_2.

The invention also provides for the use of purified and isolated antisense oligomers as described herein, for the manufacture of a medicament for treatment of a disease associated with over-expression of NEAT1_1 and/or under-expression of NEAT1_2.

There is provided the use of purified and isolated antisense oligomers as described herein for the manufacture of a medicament to treat, prevent or ameliorate the effects of a disease associated with over-expression of NEAT1_1 and/or under-expression of NEAT1_2.

Preferably, the ASO used in the present invention is chosen from the list comprising:
Table 1;
SEQ ID NO: 13 to 42 and 55;
SEQ ID NO: 13, 22, 24, 26, 28, 30, 32, 34, 36, 38, 40, 42 or 55; or
SEQ ID NO: 22, 32 or 55.

The invention extends, according to a still further aspect thereof, to cDNA or cloned copies of the antisense oligomer sequences of the invention, as well as to vectors containing the antisense oligomer sequences of the invention. The invention extends further also to cells containing such sequences and/or vectors.

The invention also provides kits to treat, prevent or ameliorate diseases associated with over-expression of NEAT1_1 and/or under-expression of NEAT1_2 in a subject, which kit comprises at least an isolated or purified antisense oligomer for modifying pre-mRNA cleavage factor binding in a NEAT1 gene transcript or part thereof, packaged in a suitable container, together with instructions for its use.

In a preferred embodiment, the kits will contain at least one antisense oligomer as described herein or as shown in Table 1, or a cocktail of antisense oligomers, as described herein. The kits may also contain peripheral reagents such as buffers, stabilizers, etc.

There is therefore provided a kit to treat, prevent or ameliorate a disease associated with over-expression of NEAT1_1 and/or under-expression of NEAT1_2 in a subject, which kit comprises at least an antisense oligomer described herein or as shown in Table 1 and combinations or cocktails thereof, packaged in a suitable container, together with instructions for its use.

There is also provided a kit to treat, prevent or ameliorate a disease associated with over-expression of NEAT1_1 and/or under-expression of NEAT1_2 in a subject which kit comprises at least an antisense oligomer selected from the group consisting of any one or more of SEQ ID NOs: 1-55, and combinations or cocktails thereof, packaged in a suitable container, together with instructions for its use.

Preferably, the disease associated with over-expression of NEAT1_1 and/or under-expression of NEAT1_2 is:
- a cancer associated with over-expression of NEAT1_1, which is indicated by the expression of NEAT11 promoting of the survival of cancer cells;
- a cancer associated with the under-expression of NEAT1_2, which is indicated by the over-expression of NEAT1_1, or alternatively by observations that when NEAT1_2 expression is increased, the cancer's growth is reduced or inhibited;
- a cancer associated with paraspeckle insufficiency or low numbers of paraspeckles;
- a cancer associated with over-expression of NEAT1_1 and/or under-expression of NEAT1_2 chosen from the list comprising: neuroblastoma, lung cancer including non-small cell lung cancer, oesophageal squamous cell carcinoma, laryngeal squamous cell carcinoma, colorectal cancer, breast cancer, prostate cancer, endometrial endometrioid adenocarcinoma, gastric cancer, glioma, thyroid carcinoma, bladder cancer, osteosarcoma, ovarian cancer;
- a cancer chosen from the list comprising: neuroblastoma, lung cancer including non-small cell lung cancer, breast cancer, bladder cancer, colorectal cancer, osteosarcoma, liver cancer, ovarian cancer;
- a cancer dependent on high activity of the cholesterol synthesis pathway; and/or
- a cancer associated with over-expression of NEAT1_1 and/or under-expression of NEAT1_2 that is also dependent on high activity of the cholesterol synthesis pathway chosen from the list comprising: neuroblastoma, osteosarcoma, or colorectal or non-small cell lung cancer.

The contents of the kit can be lyophilized and the kit can additionally contain a suitable solvent for reconstitution of the lyophilized components. Individual components of the kit would be packaged in separate containers and, associated with such containers, can be a notice in the form prescribed by a governmental agency regulating the manufacture, use or sale of pharmaceuticals or biological products, which notice reflects approval by the agency of manufacture, use or sale for human administration.

When the components of the kit are provided in one or more liquid solutions, the liquid solution can be an aqueous solution, for example a sterile aqueous solution. For in vivo use, the expression construct may be formulated into a pharmaceutically acceptable syringeable composition. In this case the container means may itself be an inhalant, syringe, pipette, eye dropper, or other such like apparatus, from which the formulation may be applied to an affected area of the animal, such as the lungs, injected into an animal, or even applied to and mixed with the other components of the kit.

The components of the kit may also be provided in dried or lyophilized forms. When reagents or components are provided as a dried form, reconstitution generally is by the addition of a suitable solvent. It is envisioned that the solvent also may be provided in another container means. Irrespective of the number or type of containers, the kits of the invention also may comprise, or be packaged with, an instrument for assisting with the injection/administration or placement of the ultimate complex composition within the body of an animal. Such an instrument may be an inhalant, syringe, pipette, forceps, measured spoon, eye dropper or any such medically approved delivery vehicle.

Those of ordinary skill in the field should appreciate that applications of the above method has wide application for identifying antisense oligomers suitable for use in the treatment of many other diseases.

The antisense oligomers of the present invention may also be used in conjunction with alternative therapies, such as drug therapies.

The present invention therefore provides a method of treating, preventing or ameliorating the effects of a disease associated with over-expression of NEAT1_1 and/or under-expression of NEAT1_2, wherein the antisense oligomers of the present invention and administered sequentially or concurrently with another alternative therapy associated with treating, preventing or ameliorating the effects of the disease associated with over-expression of NEAT1_1 and/or under-expression of NEAT1_2.

The alternative therapy may be chosen from the list comprising chemotherapy, radiation therapy, surgery, targeted therapy (including immunotherapy such as monoclonal antibody therapy), synthetic lethality and hormone therapy.

General

Throughout this specification, unless the context requires otherwise, the word "comprise" or variations such as "comprises" or "comprising", will be understood to imply the inclusion of a stated integer or group of integers but not the exclusion of any other integer or group of integers.

Throughout this specification, unless the context requires otherwise, the word "comprise" or variations such as "comprises" or "comprising", will be understood to imply the inclusion of a stated integer or group of integers but not the exclusion of any other integer or group of integers.

Other definitions for selected terms used herein may be found within the detailed description of the invention and apply throughout. Unless otherwise defined, all other scientific and technical terms used herein have the same meaning as commonly understood to one of ordinary skill in the art to which the invention belongs.

Those skilled in the art will appreciate that the invention described herein is susceptible to variations and modifications other than those specifically described. The invention includes all such variation and modifications. The invention also includes all of the steps, features, formulations and compounds referred to or indicated in the specification, individually or collectively and any and all combinations or any two or more of the steps or features.

Each document, reference, patent application or patent cited in this text is expressly incorporated herein in their entirety by reference, which means that it should be read and considered by the reader as part of this text. That the document, reference, patent application or patent cited in this text is not repeated in this text is merely for reasons of conciseness.

Any manufacturer's instructions, descriptions, product specifications, and product sheets for any products mentioned herein or in any document incorporated by reference herein, are hereby incorporated herein by reference, and may be employed in the practice of the invention.

The invention described herein may include one or more range of values (e.g. concentration). A range of values will be understood to include all values within the range, including the values defining the range, and values adjacent to the range which lead to the same or substantially the same outcome as the values immediately adjacent to that value which defines the boundary to the range.

The following Examples are to be construed as merely illustrative and not limitative of the remainder of the disclosure in any way whatsoever. These Examples are included solely for the purposes of exemplifying the present invention. They should not be understood as a restriction on the broad summary, disclosure or description of the invention as set out above. Without further elaboration, it is believed that one skilled in the art can, using the preceding description, utilize the present invention to its fullest extent. In the foregoing and in the following examples, all temperatures are set forth uncorrected in degrees Celsius; and, unless otherwise indicated, all parts and percentages are by weight.

EXAMPLES

Further features of the present invention are more fully described in the following description of several non-limiting embodiments thereof. This description is included solely for the purposes of exemplifying the present invention. It should not be understood as a restriction on the broad summary, disclosure or description of the invention as set out above.

Example 1

The paraspeckle protein NONO (a DBHS protein) is an oncogene in neuroblastoma, with high NONO levels being associated with poor outcome. The NONO binds extensively and preferentially to oncogenic pre-mRNA transcripts, causing oncogenic activity.

The present invention sought to establish if affecting the sequestering of NONO into paraspeckles using increased amounts of NEAT1_2 could affect the oncogenic activity of NONO.

General Methods
Cell Culture

KELLY cells were grown in RPMI media containing 10% FBS and 1% Penicillin streptomycin. U2OS osteosarcoma cell line, SH-SY5Y and SKNAS neuroblastoma cell lines were all grown in DMEM medium containing 10% FBS and 1% Penicillin streptomycin. All cells were cultured in a 37° C. incubator supplied with 5% $CO_2$. Cells were trypsinized using TrypLE™ Express (Life Technologies) and passaged 1:10 when reaching 90% confluency.

Transfections of ASOs or Plasmids into Cells

For U2OS cell transfections, cells were counted and plated at $4\times10^4$ cells per well of a 24-well plate. For PMO oligomer transfections, PMO oligomers were first duplexed with DNA oligomers of reverse complemented sequences at equal molar ratio in phosphate buffered saline (PBS). To anneal the duplex, the oligomers were mixed in PBS to reach 100 μM, and then incubated at 98° C. for 5 minutes before allowing to cool down to room temperature on the bench. This was prepared fresh before all transfections. One day after the cell plating, Lipofectamine 3000® (Invitrogen) and Opti-MEM® (Life Technologies) was used to conduct the transfection following the instruction provided by the manufacturer. For 2'OME ASO transfection, the same transfection reagents were used, but without the duplexing step and the usage of P3000 component in the Lipofectamine 3000® reagent. Transfected cells were harvested 48 hours post-transfection for RT-qPCR analysis of the level of NEAT1 isoforms.

For KELLY cell transfection, cells were counted and plated at either $6\times10^3$ cells per well of a 96-well plate or $1\times10^5$ per well of 6-well plate. To transfect NEAT1_1 expression plasmid, the media on the cells was first changed to RPMI 1640 media containing 4% FBS without antibiotics in the following day prior transfection, and either 100 ng (for 96-well) or 1 μg of plasmid (for 6-well) was transfected to each well using Lipofectamine 3000® and Opti-MEM® following the instruction provided by the manufacturer. For PMO and 2'OME oligomer transfections, PMO oligomers were duplexed with DNA oligomers as described above. The media on the cells was changed to RPMI 1640 media containing 4% FBS prior the transfection prior to the transfection in the following day. Lipofectamine RNAiMAX® (Invitrogen) and Opti-MEM® were used for both duplexed PMO oligomers and 2'OME ASO and at a final concentration of 25 nM. SKNAS transfections were performed as for Kelly, with the exception that $3\times10^3$ cells were placed in each well of a 96 well plate.

For all types of transfections, cells were either harvested for RNA analysis at 48 hours post-transfection (for 6-well plate), or the transfection media was replaced to normal culture media at 48 hours post-transfection for cell viability measurement seven days after the transfection (for 96-well plate).

Cell Titre Glo Cell Viability Assay

To assess cell viability following the transfection, Cell-Titer-Glo® Luminescent Cell Viability Assay (Promega) was performed as an end-point assay following the instruction provided by the manufacturer. Luminescence reading was obtained using Fluostar Optima (BMG) at 550 nm wavelength.

RTqPCR

Cells were lysed using Nucleozol Reagent and RNA extractions carried out according to the manufacturer's instructions (Machery Nagel). cDNA synthesis was performed using 125-150 ng of RNA per sample using the Qiagen Quantitect Reverse Transcription Kit according to the manufacturer's instructions. Using SYBR No-Rox mix (Bioline), qPCR experiments were conducted using customised primers to amplify reference genes B2M, and U6, as well as primers to amplify total NEAT1 (i.e., an amplicon that is in common between NEAT1_1 and NEAT1_2) as well as primers unique to NEAT1_2. Fluorescence was detected at a temperature three Celsius degrees lower than the Tm of the specific product to increase the specificity of detection. Cycle threshold (Ct) values of each product was determined under a constant normalised fluorescence threshold of 0.075. qPCRs were performed using a rotogene thermal cycler (Qiagen). Relative RNA levels were calculated with the $2^{-\Delta\Delta CT}$ method. Relative expression of genes was calculated using the $2^{-\Delta\Delta Ct}$ method against two house-keeping genes (Livak and Schmittgen 2001, Analysis of Relative Gene Expression Data Using Real-Time Quantitative PCR and the 2-ΔΔCT Method. *Methods* 25(4): 402-408). RT-qPCR primers are listed as follows:

```
NEAT1_total_F:
                                           (SEQ ID NO: 56)
5'-GTGGCTGTTGGAGTCGGTAT-3'

NEAT1_total_R:
                                           (SEQ ID NO: 57)
5'-TAACAAACCACGGTCCATGA-3'

NEAT1_2_F:
                                           (SEQ ID NO: 58)
5'-GTCTTTCCATCCACTCACGTCTATTT-3'

NEAT1_2_R:
                                           (SEQ ID NO: 59)
5'-GTACTCTGTGATGGGGTAGTCAGTCAG-3'

B2M_F:
                                           (SEQ ID NO: 60)
5'-GAGGCTATCCAGCGTACTCCA-3'

B2M_R:
                                           (SEQ ID NO: 61)
5'-CGGCAGGCATACTCATCTTTT-3'

U6_F:
                                           (SEQ ID NO: 62)
CTCGCTTCGGCAGCACA

U6_R:
                                           (SEQ ID NO: 63)
AACGCTTCACGAATTTGCGT
``` qPCRs were performed using a Rotogene Thermal Cycler (Qiagen). Relative RNA levels were calculated with the $2^{-\Delta\Delta CT}$ method.

Fluorescent In Situ Hybridization (FISH) and Paraspeckle Quantitation

Transfected cells grown on coverslips were fixed using 4% paraformaldehyde, and permeabilized by 70% ethanol overnight. Stellaris human NEAT1 RNA-FISH probes (Biosearch Technologies) were used and the procedure was carried out according to the instruction provided. In brief, permeabilized cells were incubated with probes in hybridization buffer overnight at 37° C., and washed with buffer for 30 minutes afterwards. For immunofluorescence staining, cells were then incubated with primary NONO antibody in PBST (phosphate buffered saline containing 0.05% tween-20) for 1 hour at 37° C., and then washed with PBST for 3 times of 5 minutes each. Cells were then incubated with anti-mouse FITC conjugated secondary antibodies in PBST for 1 hour and 37° C., and then washed 3 times again. Finally, cells were incubated with 1:15000 4',6-diamidino-2-phenylindole (DAPI) in PBS for 2 minutes at room temperature, and then mounted onto slides with VectaShield (Vector Laboratories) mounting media. Fluorescence signals were imaged using the DeltaVision Elite Imaging System and Softworx software (GE Healthcare). Images were Z-stacks of 0.2 μm sections, subject to deconvolution and projected with maximum intensity. Identical exposure settings and post-processing parameters were used within each set of experiments. For counting paraspeckles, images were taken using 60× objective lens using the same exposure settings. Paraspeckles were defined as NEAT1_2 RNA-FISH signal that are co-localising with NONO and are larger than 6 pixels (at 1024×1024 resolution). Paraspeckle counting was achieved by applying the same thresholding parameters for the red fluorescence channel to each image. Thresholded objects were then counted.

---

The invention claimed is:

1. An isolated or purified antisense oligomer targeted to a nucleic acid molecule encoding the NEAT1 pre-mRNA or part thereof, wherein the antisense oligomer has a nucleobase sequence selected from the group consisting of:

(a) the nucleobase sequence of any one of SEQ ID NOs: 1-55; and (b) a nucleobase sequence comprising at least 97% sequence identity to any one of SEQ ID NOs: 1-55, wherein the antisense oligomer has a modified backbone structure, and wherein the antisense oligomer reduces cleavage in the NEAT1 gene transcript or part thereof to change the ratio of short form NEAT1_1:long form NEAT1_2 by increasing the amount of long form NEAT1_2 and/or decreasing the amount of short form NEAT1_1.

2. The antisense oligomer of claim 1 that increases the amount of long form NEAT1_2.

3. The antisense oligomer of claim 1 that decreases the amount of short form NEAT1_1.

4. The antisense oligomer of claim 1 comprising a targeting sequence complementary to a region near or within the polyadenylation site of NEAT1_1.

5. The antisense oligomer of claim 1 that is a phosphorodiamidate morpholino oligomer.

6. The antisense oligomer of claim 1 that has a nucleobase sequence selected from the group consisting of: SEQ ID NOs: 13 to 42 and 55.

7. The antisense oligomer of claim 1 comprising: SEQ ID NO: 13, 22, 24, 26, 28, 30, 32, 34, 36, 38, 40, 42 or 55.

8. The antisense oligomer of claim 1 comprising: SEQ ID NO: 22, 32 or 55.

9. The antisense oligomer of claim 1 wherein the antisense oligomer:

i) contains one or more nucleotide positions subject to an alternative chemistry or modification selected from the group consisting of: (i) modified sugar moieties; (ii) resistance to RNase H; (iii) oligomeric mimetic chemistry; and (iv) combinations thereof; and/or ii) is further modified by: (i) chemical conjugation to a moiety; and/or (ii) tagging with a cell penetrating peptide.

10. The antisense oligomer of claim 1 wherein, if a uracil (U) is present in the antisense oligomer, the uracil (U) of the antisense oligomer is replaced by a thymine (T).

11. A pharmaceutical composition comprising:
one or more antisense oligomers according to claim 1; and
one or more pharmaceutically acceptable carriers and/or diluents.

12. A kit to treat or ameliorate the effects of a cancer associated with over-expression of NEAT1_1 and/or under-expression of NEAT1_2 in a subject, which kit comprises at least an antisense oligomer according to claim 1, packaged in a suitable container, together with instructions for its use.

13. A method for manipulating cleavage factor binding in a NEAT1 gene transcript, the method including the step of:
providing one or more of the antisense oligomers according to claim 1 and allowing the oligomer(s) to bind to a target nucleic acid site.

14. A method to treat or ameliorate the effects of a cancer associated with over-expression of NEAT1_1 and/or under-expression of NEAT1_2 in a subject, the method comprising the step of:
administering to the subject an effective amount of one or more antisense oligomers or pharmaceutical composition comprising one or more antisense oligomers according to claim 1.

15. The method of claim 14 wherein the cancer is:
i) associated with over-expression of NEAT1_1;
ii) associated with an under-expression of NEAT1_2;
iii) associated with paraspeckle insufficiency or low numbers of paraspeckles
iv) a neuroblastoma, lung cancer including non-small cell lung cancer, oesophageal squamous cell carcinoma, laryngeal squamous cell carcinoma, colorectal cancer, breast cancer, prostate cancer, endometrial endometrioid adenocarcinoma, gastric cancer, glioma, thyroid carcinoma, bladder cancer, osteosarcoma, or ovarian cancer;
v) chosen from the list comprising: neuroblastoma, lung cancer including non-small cell lung cancer, breast cancer, bladder cancer, colorectal cancer, osteosarcoma, liver cancer, and ovarian cancer;
vi) chosen from the list comprising: neuroblastoma, osteosarcoma, colorectal cancer, and non-small cell lung cancer;
vii) dependent on high activity of the cholesterol synthesis pathway; and/or
viii) associated with over-expression of NEAT1_1 and/or under-expression of NEAT1_2 that is also dependent on high activity of the cholesterol synthesis pathway chosen from the list comprising: neuroblastoma, osteosarcoma, or colorectal or non-small cell lung cancer.

16. A method to ameliorate the effects of a cancer associated with over-expression of NEAT1_1 and/or under-expression of NEAT1_2 in a subject, the method comprising a step of: administering to the subject an effective amount of a composition according to claim 11.

17. An isolated or purified antisense oligomer targeted to a nucleic acid molecule encoding the NEAT1 pre-mRNA or part thereof, wherein the antisense oligomer has a nucleobase sequence selected from the group consisting of:
(a) SEQ ID NO: 55, and
(b) a sequence comprising at least 97% sequence identity to SEQ ID NO: 55,
wherein the antisense oligomer has a modified backbone structure, and
wherein the antisense oligomer reduces cleavage in the NEAT1 gene transcript or part thereof to change the ratio of short form NEAT1_1:long form NEAT1_2 by increasing the amount of long form NEAT1_2 and/or decreasing the amount of short form NEAT1_1.

18. The antisense oligomer of claim 17 wherein the antisense oligomer:
i) contains one or more nucleotide positions subject to an alternative chemistry or modification selected from the group consisting of: (i) modified sugar moieties; (ii) resistance to RNase H; (iii) oligomeric mimetic chemistry; and (iv) combinations thereof; and/or
ii) is further modified by: (i) chemical conjugation to a moiety; and/or (ii) tagging with a cell penetrating peptide.

* * * * *

SEQUENCE LISTING

```
<160> NUMBER OF SEQ ID NOS: 64

<210> SEQ ID NO 1
<211> LENGTH: 25
<212> TYPE: DNA
<213> ORGANISM: Homo sapiens

<400> SEQUENCE: 1
acaacaattc taatgagttt agaac                                           25

<210> SEQ ID NO 2
<211> LENGTH: 25
<212> TYPE: DNA
<213> ORGANISM: Homo sapiens

<400> SEQUENCE: 2
caacaattct aatgagttta gaact                                           25

<210> SEQ ID NO 3
<211> LENGTH: 25
<212> TYPE: DNA
<213> ORGANISM: Homo sapiens

<400> SEQUENCE: 3
aacaattcta atgagtttag aactc                                           25

<210> SEQ ID NO 4
<211> LENGTH: 25
<212> TYPE: DNA
<213> ORGANISM: Homo sapiens

<400> SEQUENCE: 4
```
acaattctaa tgagtttaga actca                                              25

<210> SEQ ID NO 5
<211> LENGTH: 25
<212> TYPE: DNA
<213> ORGANISM: Homo sapiens

<400> SEQUENCE: 5
caattctaat gagtttagaa ctcaa                                              25

<210> SEQ ID NO 6
<211> LENGTH: 25
<212> TYPE: DNA
<213> ORGANISM: Homo sapiens

<400> SEQUENCE: 6
aattctaatg agtttagaac tcaaa                                              25

<210> SEQ ID NO 7
<211> LENGTH: 25
<212> TYPE: DNA
<213> ORGANISM: Homo sapiens

<400> SEQUENCE: 7
attctaatga gtttagaact caaac                                              25

<210> SEQ ID NO 8
<211> LENGTH: 25
<212> TYPE: DNA
<213> ORGANISM: Homo sapiens

<400> SEQUENCE: 8
ttctaatgag tttagaactc aaact                                              25

<210> SEQ ID NO 9
<211> LENGTH: 25
<212> TYPE: DNA
<213> ORGANISM: Homo sapiens

<400> SEQUENCE: 9
tctaatgagt ttagaactca aactt                                              25

<210> SEQ ID NO 10
<211> LENGTH: 25
<212> TYPE: DNA
<213> ORGANISM: Homo sapiens

<400> SEQUENCE: 10
ctaatgagtt tagaactcaa acttt                                              25

<210> SEQ ID NO 11
<211> LENGTH: 25
<212> TYPE: DNA
<213> ORGANISM: Homo sapiens

<400> SEQUENCE: 11
taatgagttt agaactcaaa cttta                                              25

<210> SEQ ID NO 12
<211> LENGTH: 25
<212> TYPE: DNA
<213> ORGANISM: Homo sapiens

```
<400> SEQUENCE: 12
aatgagttta gaactcaaac tttat                                          25

<210> SEQ ID NO 13
<211> LENGTH: 25
<212> TYPE: DNA
<213> ORGANISM: Homo sapiens

<400> SEQUENCE: 13
atgagtttag aactcaaact ttatt                                          25

<210> SEQ ID NO 14
<211> LENGTH: 25
<212> TYPE: DNA
<213> ORGANISM: Homo sapiens

<400> SEQUENCE: 14
tgagtttaga actcaaactt tattt                                          25

<210> SEQ ID NO 15
<211> LENGTH: 25
<212> TYPE: DNA
<213> ORGANISM: Homo sapiens

<400> SEQUENCE: 15
gagtttagaa ctcaaacttt atttg                                          25

<210> SEQ ID NO 16
<211> LENGTH: 25
<212> TYPE: DNA
<213> ORGANISM: Homo sapiens

<400> SEQUENCE: 16
agtttagaac tcaaacttta tttgt                                          25

<210> SEQ ID NO 17
<211> LENGTH: 25
<212> TYPE: DNA
<213> ORGANISM: Homo sapiens

<400> SEQUENCE: 17
gtttagaact caaactttat ttgtg                                          25

<210> SEQ ID NO 18
<211> LENGTH: 25
<212> TYPE: DNA
<213> ORGANISM: Homo sapiens

<400> SEQUENCE: 18
tttagaactc aaactttatt tgtgc                                          25

<210> SEQ ID NO 19
<211> LENGTH: 25
<212> TYPE: DNA
<213> ORGANISM: Homo sapiens

<400> SEQUENCE: 19
ttagaactca aactttattt gtgct                                          25

<210> SEQ ID NO 20
<211> LENGTH: 25
<212> TYPE: DNA
<213> ORGANISM: Homo sapiens
```

```
<400> SEQUENCE: 20
tagaactcaa actttatttg tgctg                                          25

<210> SEQ ID NO 21
<211> LENGTH: 25
<212> TYPE: DNA
<213> ORGANISM: Homo sapiens

<400> SEQUENCE: 21
agaactcaaa ctttatttgt gctgt                                          25

<210> SEQ ID NO 22
<211> LENGTH: 25
<212> TYPE: DNA
<213> ORGANISM: Homo sapiens

<400> SEQUENCE: 22
gaactcaaac tttatttgtg ctgta                                          25

<210> SEQ ID NO 23
<211> LENGTH: 25
<212> TYPE: DNA
<213> ORGANISM: Homo sapiens

<400> SEQUENCE: 23
aactcaaact ttatttgtgc tgtaa                                          25

<210> SEQ ID NO 24
<211> LENGTH: 25
<212> TYPE: DNA
<213> ORGANISM: Homo sapiens

<400> SEQUENCE: 24
actcaaactt tatttgtgct gtaaa                                          25

<210> SEQ ID NO 25
<211> LENGTH: 25
<212> TYPE: DNA
<213> ORGANISM: Homo sapiens

<400> SEQUENCE: 25
ctcaaacttt atttgtgctg taaag                                          25

<210> SEQ ID NO 26
<211> LENGTH: 25
<212> TYPE: DNA
<213> ORGANISM: Homo sapiens

<400> SEQUENCE: 26
tcaaacttta tttgtgctgt aaagg                                          25

<210> SEQ ID NO 27
<211> LENGTH: 25
<212> TYPE: DNA
<213> ORGANISM: Homo sapiens

<400> SEQUENCE: 27
caaactttat ttgtgctgta aaggg                                          25

<210> SEQ ID NO 28
<211> LENGTH: 25
<212> TYPE: DNA
```

<213> ORGANISM: Homo sapiens

<400> SEQUENCE: 28
aaactttatt tgtgctgtaa agggg    25

<210> SEQ ID NO 29
<211> LENGTH: 25
<212> TYPE: DNA
<213> ORGANISM: Homo sapiens

<400> SEQUENCE: 29
aactttattt gtgctgtaaa gggga    25

<210> SEQ ID NO 30
<211> LENGTH: 25
<212> TYPE: DNA
<213> ORGANISM: Homo sapiens

<400> SEQUENCE: 30
actttatttg tgctgtaaag gggaa    25

<210> SEQ ID NO 31
<211> LENGTH: 25
<212> TYPE: DNA
<213> ORGANISM: Homo sapiens

<400> SEQUENCE: 31
ctttatttgt gctgtaaagg ggaag    25

<210> SEQ ID NO 32
<211> LENGTH: 25
<212> TYPE: DNA
<213> ORGANISM: Homo sapiens

<400> SEQUENCE: 32
tttatttgtg ctgtaaaggg gaaga    25

<210> SEQ ID NO 33
<211> LENGTH: 25
<212> TYPE: DNA
<213> ORGANISM: Homo sapiens

<400> SEQUENCE: 33
ttatttgtgc tgtaaagggg aagaa    25

<210> SEQ ID NO 34
<211> LENGTH: 25
<212> TYPE: DNA
<213> ORGANISM: Homo sapiens

<400> SEQUENCE: 34
tatttgtgct gtaaagggga agaaa    25

<210> SEQ ID NO 35
<211> LENGTH: 25
<212> TYPE: DNA
<213> ORGANISM: Homo sapiens

<400> SEQUENCE: 35
atttgtgctg taaaggggaa gaaaa    25

<210> SEQ ID NO 36
<211> LENGTH: 25

<212> TYPE: DNA
<213> ORGANISM: Homo sapiens

<400> SEQUENCE: 36
tttgtgctgt aaagggaaag aaaag                                          25

<210> SEQ ID NO 37
<211> LENGTH: 25
<212> TYPE: DNA
<213> ORGANISM: Homo sapiens

<400> SEQUENCE: 37
ttgtgctgta aaggggaaga aaagt                                          25

<210> SEQ ID NO 38
<211> LENGTH: 25
<212> TYPE: DNA
<213> ORGANISM: Homo sapiens

<400> SEQUENCE: 38
tgtgctgtaa agggaagaa aagtg                                           25

<210> SEQ ID NO 39
<211> LENGTH: 25
<212> TYPE: DNA
<213> ORGANISM: Homo sapiens

<400> SEQUENCE: 39
gtgctgtaaa ggggaagaaa agtga                                          25

<210> SEQ ID NO 40
<211> LENGTH: 25
<212> TYPE: DNA
<213> ORGANISM: Homo sapiens

<400> SEQUENCE: 40
tgctgtaaag gggaagaaaa gtgat                                          25

<210> SEQ ID NO 41
<211> LENGTH: 25
<212> TYPE: DNA
<213> ORGANISM: Homo sapiens

<400> SEQUENCE: 41
gctgtaaagg ggaagaaaag tgatt                                          25

<210> SEQ ID NO 42
<211> LENGTH: 25
<212> TYPE: DNA
<213> ORGANISM: Homo sapiens

<400> SEQUENCE: 42
ctgtaaaggg gaagaaaagt gatta                                          25

<210> SEQ ID NO 43
<211> LENGTH: 25
<212> TYPE: DNA
<213> ORGANISM: Homo sapiens

<400> SEQUENCE: 43
tgtaaagggg aagaaaagtg attag                                          25

<210> SEQ ID NO 44

```
<211> LENGTH: 25
<212> TYPE: DNA
<213> ORGANISM: Homo sapiens

<400> SEQUENCE: 44
gtaaagggga agaaaagtga ttagt                                              25

<210> SEQ ID NO 45
<211> LENGTH: 25
<212> TYPE: DNA
<213> ORGANISM: Homo sapiens

<400> SEQUENCE: 45
agcaacatac cagtactttc aacca                                              25

<210> SEQ ID NO 46
<211> LENGTH: 25
<212> TYPE: DNA
<213> ORGANISM: Homo sapiens

<400> SEQUENCE: 46
catacagagc aacataccag tactt                                              25

<210> SEQ ID NO 47
<211> LENGTH: 25
<212> TYPE: DNA
<213> ORGANISM: Homo sapiens

<400> SEQUENCE: 47
gtaacagaat tagttcttac catac                                              25

<210> SEQ ID NO 48
<211> LENGTH: 25
<212> TYPE: DNA
<213> ORGANISM: Homo sapiens

<400> SEQUENCE: 48
ttagtaatta tgtacatgac gtaac                                              25

<210> SEQ ID NO 49
<211> LENGTH: 25
<212> TYPE: DNA
<213> ORGANISM: Homo sapiens

<400> SEQUENCE: 49
gagaaatgta acatagcaat acaac                                              25

<210> SEQ ID NO 50
<211> LENGTH: 25
<212> TYPE: DNA
<213> ORGANISM: Homo sapiens

<400> SEQUENCE: 50
aaggcaatgt datagggtc gagaa                                               25

<210> SEQ ID NO 51
<211> LENGTH: 25
<212> TYPE: DNA
<213> ORGANISM: Homo sapiens

<400> SEQUENCE: 51
atacatccaa agtcgttatg aaggc                                              25
```

```
<210> SEQ ID NO 52
<211> LENGTH: 25
<212> TYPE: DNA
<213> ORGANISM: Homo sapiens

<400> SEQUENCE: 52
atgaagtatc atccaaagtc gaatt                                          25

<210> SEQ ID NO 53
<211> LENGTH: 24
<212> TYPE: DNA
<213> ORGANISM: Homo sapiens

<400> SEQUENCE: 53
tttatttgtg ctgtaaaggg aaga                                           24

<210> SEQ ID NO 54
<211> LENGTH: 25
<212> TYPE: DNA
<213> ORGANISM: Homo sapiens

<400> SEQUENCE: 54
tttatttgtg ctgtaaaggt gaaga                                          25

<210> SEQ ID NO 55
<211> LENGTH: 20
<212> TYPE: DNA
<213> ORGANISM: Homo sapiens

<400> SEQUENCE: 55
tttatttgtg ctgtaaaggg                                                20

<210> SEQ ID NO 56
<211> LENGTH: 20
<212> TYPE: DNA
<213> ORGANISM: Homo Sapiens

<400> SEQUENCE: 56
gtggctgttg gagtcggtat                                                20

<210> SEQ ID NO 57
<211> LENGTH: 20
<212> TYPE: DNA
<213> ORGANISM: Homo Sapiens

<400> SEQUENCE: 57
taacaaacca cggtccatga                                                20

<210> SEQ ID NO 58
<211> LENGTH: 26
<212> TYPE: DNA
<213> ORGANISM: Homo Sapiens

<400> SEQUENCE: 58
gtctttccat ccactcacgt ctattt                                         26

<210> SEQ ID NO 59
<211> LENGTH: 27
<212> TYPE: DNA
<213> ORGANISM: Homo Sapiens

<400> SEQUENCE: 59
gtactctgtg atggggtagt cagtcag                                        27
```

```
<210> SEQ ID NO 60
<211> LENGTH: 21
<212> TYPE: DNA
<213> ORGANISM: Homo Sapiens

<400> SEQUENCE: 60
gaggctatcc agcgtactcc a                                              21

<210> SEQ ID NO 61
<211> LENGTH: 21
<212> TYPE: DNA
<213> ORGANISM: Homo Sapiens

<400> SEQUENCE: 61
cggcaggcat actcatcttt t                                              21

<210> SEQ ID NO 62
<211> LENGTH: 17
<212> TYPE: DNA
<213> ORGANISM: Homo Sapiens

<400> SEQUENCE: 62
ctcgcttcgg cagcaca                                                   17

<210> SEQ ID NO 63
<211> LENGTH: 20
<212> TYPE: DNA
<213> ORGANISM: Homo Sapiens

<400> SEQUENCE: 63
aacgcttcac gaatttgcgt                                                20

<210> SEQ ID NO 64
<211> LENGTH: 97
<212> TYPE: DNA
<213> ORGANISM: Homo Sapiens

<400> SEQUENCE: 64
tacgtcatgt acataattac taatcacttt tcttcccctt tacagcacaa ataaagtttg    60
agttctaaac tcattagaat tgttgtattg ctatgtt                             97
```